United States Patent
Koplitz et al.

(10) Patent No.: US 10,961,224 B2
(45) Date of Patent: Mar. 30, 2021

(54) TRIAZINIUM CATION FORMS AND METHODS OF MAKING THEREOF

(71) Applicant: Loyola University New Orleans, New Orleans, LA (US)

(72) Inventors: Lynn Vogel Koplitz, New Orleans, LA (US); Clifton J. Stephenson, New Orleans, LA (US)

(73) Assignee: Loyola University New Orleans, New Orleans, LA (US)

( * ) Notice: Subject to any disclaimer, the term of this patent is extended or adjusted under 35 U.S.C. 154(b) by 88 days.

(21) Appl. No.: 16/497,793

(22) PCT Filed: Mar. 29, 2018

(86) PCT No.: PCT/US2018/025253
§ 371 (c)(1),
(2) Date: Sep. 26, 2019

(87) PCT Pub. No.: WO2018/183749
PCT Pub. Date: Oct. 4, 2018

(65) Prior Publication Data
US 2020/0024258 A1    Jan. 23, 2020

Related U.S. Application Data

(60) Provisional application No. 62/478,930, filed on Mar. 30, 2017.

(51) Int. Cl.
| | |
|---|---|
| *C07D 401/14* | (2006.01) |
| *H01L 51/50* | (2006.01) |
| *H01L 51/00* | (2006.01) |
| *H01L 51/05* | (2006.01) |

(52) U.S. Cl.
CPC ........ *C07D 401/14* (2013.01); *H01L 51/0067* (2013.01); *C07B 2200/13* (2013.01); *H01L 51/05* (2013.01); *H01L 51/50* (2013.01)

(58) Field of Classification Search
CPC ....... C07D 401/14; C09K 11/06; H01L 51/50; H01L 51/0067
USPC ...................................................... 544/198
See application file for complete search history.

(56) References Cited

U.S. PATENT DOCUMENTS 3,855,220 A * 12/1974 Fischer ................ C07D 213/78
544/180

OTHER PUBLICATIONS

Nguyen, V. D. et. al., Two red salts derived from yellow 4-cyano-1-methylpyridinium iodide: 1,1',1"-trimethyl-4,4',4"—(1,3,5-triazin-2,4,6-triyl)tripyridinium trisiodide and 4-cyano-1-methylpyridinium trilodide, Polyhedron, 114: 428-434 (2016).
PubChem Compound Identification No. 110191404, Create Date: Jan. 18, 2016.
He. J. et. al., Highly Polarizable Triiodide Anions (I3-) as Cross-Linkers for Coordination Polymers: Closing the Semiconductive Band Gap, Inorganic Chemistry, 54(13), 6087-6089 (2015).
Kammer, M., 4-Cyano-1-methyl-pyridinium iodide, Acta crystallographica, Section E, 68, o2514 (2012).
Nguyen, V. D. et. al., 4-Cyano-1-methyl-pyridinium perchlorate, Acta crystallographica, Section E, 70, o756-o757.
McCormick, C., et. al., 4-Cyano-1-methylpyridinium nitrate, Acta crystallographica, Section E, 69, o981-o982 (2013).
Nguyen, V. D. et al., Cyclotrimerization of 4-cyano-1-methylpyridinium Abs, 247th ACS National Meeting, Dallas, TX; Mar. 2014 (2014).
PubChem Compound Identification No. 494189, Create Date: Aug. 1, 2005.
PubChem Compound Identification No. 317666, Create Date; Mar. 26, 2005.
PubChem Compound Identification No. 110191405, Create Date: Jan. 18, 2016.
PubChem Compound Identification No. 11472427, Create Date: Oct. 26, 2006.
PubChem Compound Identification No. 54601749, Create Date: Dec. 19, 2011.
PubChem Compound Identification No. 429234, Create Date: Mar. 26, 2005.
PubChem Compound Identification No. 77258, Create Date: Mar. 26, 2005.
PubChem Compound Identification No. 54607178, Create Date: Dec. 19, 2011.
International Search Report for PCT/US2018/026253, dated Sep. 4, 2018, 4 pages.
Written Opinion of PCT/US2018/025253, dated Sep. 4, 2018, 17 pages.

* cited by examiner

*Primary Examiner* — Venkataraman Balasubramanian

(57) ABSTRACT

The present disclosure provides, among other things, compounds and crystalline forms of compounds thereof and methods of making and using such compounds and crystalline forms of compounds. Disclosed compounds and crystalline forms are useful in electronic materials, semiconductor materials, and optoelectronic materials and devices incorporating these materials and which exhibit desirable characteristics for the same.

20 Claims, 39 Drawing Sheets

(a)

(b)

(c)

(a)

(b)

TRIAZINIUM CATION FORMS AND METHODS OF MAKING THEREOF

CROSS-REFERENCE TO RELATED APPLICATIONS

This application is a National Stage Entry of International Patent Application No. PCT/US2018/025253, filed on Mar. 29, 2018, which claims the benefit of priority of U.S. Provisional Application Ser. No. 62/478,930 filed on Mar. 30, 2017, entitled "TRIAZINIUM IODIDE FORMS AND METHODS OF MAKING THEREOF" the entire contents of each of which are hereby incorporated by reference herein.

BACKGROUND

Optoelectronic materials, devices and systems source, detect, and control electromagnetic radiation. Typical optoelectronic materials are made of metals and/or metalloids. Examples of these materials include aluminum, arsenic gallium, indium among others. The properties of such optoelectronic materials are tuned by varying the proportions of the elements present. In most cases these materials are toxic and heavy. Organic conductors and semiconductors are less toxic, lighter and more flexible.

SUMMARY

Among other things, the present disclosure provides an insight that some compounds, crystalline forms of compounds, compositions, and devices are particularly useful as optoelectronic semiconductor materials and devices with surprising and beneficial attributes. The present disclosure also provides methods of making and using such compounds, crystalline forms of compounds, compositions, and devices.

In some embodiments, compounds and crystalline forms of compounds are characterized by their electronic and/or optoelectronic properties.

Implementations of compounds and crystalline forms of compounds of the present disclosure are useful as materials and in a wide range of devices, including, for example: electronic materials and devices including, for example, doubling crystals, field effect transistors, lasers, LEDs, liquid crystal devices, liquid crystal displays, OFETs, OLEDs (organic light-emitting diodes) for vividly colorful displays, piezoelectrics, photonic modulators, photovoltaic cells, photovoltaics, sensors, semiconductor devices, specialized solar panels, and/or thermoelectrics.

The present disclosure provides compounds and crystalline forms of compounds. In some embodiments, compounds and crystalline forms of compounds are characterized in that they are substantially free of their starting materials. In some embodiments, crystalline forms of compounds are characterized in that they are substantially free of their amorphous form.

In some embodiments, provided compounds and crystalline forms of compounds include crystals of 4-cyano-1-methylpyridinium triiodide, Compound I.

In some embodiments, provided compounds and crystalline forms of compounds include:

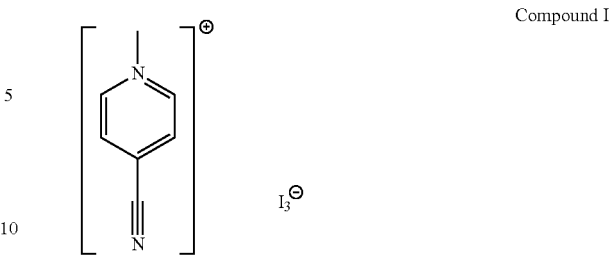

Compound I

In some embodiments, provided compounds and crystalline forms of compounds include crystals of 1,1',1"-trimethyl-4,4',4"-(1,3,5-triazin-2,4,6-triyl)tripyridinium trisiodide, Compound II.

In some embodiments, provided compounds and crystalline forms of compounds include:

Compound II

In some embodiments, provided compounds and crystalline forms of compounds are characterized by one or more peaks in its powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

In some embodiments, provided compounds and crystalline forms of compounds are characterized by one or more peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

In some embodiments, provided compounds and crystalline forms of compounds are characterized by a monoclinic unit cell.

In some embodiments, provided compounds and crystalline forms of compounds are characterized by a trigonal unit cell.

In some embodiments, provided compounds and crystalline forms of compounds include crystals of 1,1',1"-triethyl-3,3',3"-(1,3,5-triazin-2,4,6-triyl)tripyridinium trisiodide.

In some embodiments, provided compounds and crystalline forms of compounds include crystals of 1,1',1"-trimethyl-2,2',2"-(1,3,5-triazin-2,4,6-triyl)tripyridinium trisiodide In some embodiments, provided compounds and crystalline forms of compounds include crystals of 1,1',1"-triethyl-4,4',4"-(1,3,5-triazin-2,4,6-triyl)tripyridinium trisiodide.

In some embodiments, provided compounds and crystalline forms of compounds include crystals of 1,1',1"-trimethyl-3,3',3"-(1,3,5-triazin-2,4,6-triyl)tripyridinium trisiodide.

In some embodiments, provided compounds and crystalline forms of compounds include crystals of 1,1',1''-triethyl-2,2',2''-(1,3,5-triazin-2,4,6-triyl)tripyridinium trisiodide.

In some embodiments, provided compounds and crystalline forms of compounds include crystals of 1,1',1''-triethyl-4,4',4''-(1,3,5-triazin-2,4,6-triyl)tripyridinium trisbromide.

In some embodiments, provided compounds and crystalline forms of compounds include crystals of 1,1',1''-triethyl-3,3',3''-(1,3,5-triazin-2,4,6-triyl)tripyridinium trisbromide.

In some embodiments, compounds and/or crystalline forms of organic salts disclosed herein possess measurable properties, for example, including band gap, charge mobility, conductivity, dielectric constant, HOMO-LUMO gap, magnetic characteristics, octapole moments, and/or resistivity. In some embodiments, such compound, forms, and/or salts are characterized by measurable properties.

In some embodiments, provided compounds and crystalline forms of compounds are characterized by a band gap in a range of about 0.5 eV and 4 eV.

In some embodiments, compounds and crystalline forms of compounds disclosed herein exhibit an emission wavelength of about 200 nm to about 3000 nm.

In some embodiments, provided compounds and crystalline forms of compounds are characterized by a resistivity in a range of about $10^2$ Ωm to about $10^{-4}$ Ωm measured at about room temperature.

In some embodiments, compounds and crystalline forms of compounds disclosed herein exhibit an electron mobility in a range of about 50-50,000 $\mu_e$ cm$^2$/Vs. In some embodiments, compounds and crystalline forms of compounds disclosed herein exhibit a hole mobility in a range of about 1-5,000 $\mu_e$ cm$^2$/Vs.

In some embodiments, provided compounds and crystalline forms of compounds are useful as materials in electronic, optoelectronic, or semiconductor devices.

In some embodiments, provided compounds and crystalline forms of compounds are characterized in that they exhibit diamagnetism. In some embodiments, provided compounds and crystalline forms of compounds are characterized by their magnetic moment.

In some embodiments, provided compounds and crystalline forms of compounds are characterized by a Piedfort Unit having face to face π-π stacking. In some embodiments, provided compounds and crystalline forms of compounds include two cations and six anions so that the crystal has a non-zero octupolar moment.

In some embodiments, provided compounds and crystalline forms of compounds are or are used in devices, such as electronic, optical, and/or optoelectronic devices, including doubling crystals, field effect transistors, lasers, LEDs, liquid crystal devices, liquid crystal displays, OFETs, OLEDs (organic light-emitting diodes) for vividly colorful displays, piezoelectrics, photonic modulators, photovoltaic cells, photovoltaics, sensors, semiconductor devices, specialized solar panels, and/or thermoelectrics.

In some embodiments, the present disclosure provides methods of making compounds and/or crystalline forms of compounds and using compounds and/or crystalline forms of compounds.

In some embodiments, methods of providing, preparing, and/or manufacturing compounds and/or crystalline forms of compounds of the present disclosure include providing or preparing 4-cyano-1-methylpyridinium triiodide, Compound I.

In some embodiments, methods of providing, preparing, and/or manufacturing compounds and/or crystalline forms of compounds of the present disclosure include synthesizing 4-cyano-1-methylpyridinium triiodide, Compound I by reacting CH$_3$I and a s-triazine (1,3,5-triazine) to form 4-cyano-1-methylpyridinium iodide. In some embodiments, methods of providing, preparing, and/or manufacturing compounds and/or crystalline forms of compounds of the present disclosure include synthesizing Compound I by reacting a previously synthesized 4-cyano-1-methylpyridinium iodide in water or methanol with mercury(I) chloride and/or lead(II) chloride.

In some embodiments, methods of providing, preparing, and/or manufacturing compounds and/or crystalline forms of compounds of the present disclosure include providing or preparing 1,1',1''-trimethyl-4,4',4''-(1,3,5-triazin-2,4,6-triyl)tripyridinium trisiodide, Compound II.

In some embodiments, methods of providing, preparing, and/or manufacturing compounds and/or crystalline forms of compounds of the present disclosure include synthesizing 1,1',1''-trimethyl-4,4',4''-(1,3,5-triazin-2,4,6-triyl)tripyridinium trisiodide, Compound II, by a cyclotrimerization of a previously synthesized 4-cyano-1-methylpyridinium iodide.

In some embodiments, methods of providing, preparing, and/or manufacturing compounds and/or crystalline forms of compounds of the present disclosure include synthesizing 1,1',1''-trimethyl-4,4',4''-(1,3,5-triazin-2,4,6-triyl)tripyridinium trisiodide, Compound II by reacting 4-cyano-1-methylpyridinium iodide with methanol or water. In some embodiments, methods include reacting a previously synthesized 4-cyano-1-methylpyridinium iodide in water or methanol with Hg$_2$Cl$_2$ and/or PbCl$_2$ and/or AgCl to form 1,1',1''-trimethyl-4,4',4''-(1,3,5-triazin-2,4,6-triyl)tripyridinium trisiodide, Compound II.

In some embodiments, methods of providing, preparing, and/or manufacturing compounds and/or crystalline forms of compounds of the present disclosure include synthesizing 1,1',1''-trimethyl-4,4',4''-(1,3,5-triazin-2,4,6-triyl)tripyridinium trisiodide, Compound II, by mixing 2,4,6-tris-(4-pyridyl)-1,3,5-triazine with dimethylformamide and then reacting with methyl iodide to form 1,1',1''-trimethyl-4,4',4''-(1,3,5-triazin-2,4,6-triyl)tripyridinium trisiodide, Compound II.

All publications, patent applications, patents, and other references mentioned herein are incorporated by reference herein in their entirety.

BRIEF DESCRIPTION OF THE DRAWING

FIG. 3 at panel (a) shows 1 mm×7 mm shiny black rods. FIG. 3 at panel (b) shows needles smaller than those depicted in panel (a). FIG. 3 at panel (c) shows one smaller, long needle exhibiting how it is dark red in appearance under transmitted light.

FIG. 14 at panel (a) shows a top view of the structure of Compound II. FIG. 14 at panel (b) shows a bottom view of the structure of Compound II.

FIG. 16 shows at panel (a) shows UV-Vis absorption spectra over time of reaction mixture using an equimolar amount of Lewis acid $Hg_2Cl_2$. FIG. 16 at panel (b) shows UV-Vis absorption spectra over time of reaction mixture using catalytic amount of Lewis acid $Hg_2Cl_2$

FIG. 19 at panel (a) shows magnetic moment vs. temperature at a field of 30 Oe. FIG. 19 at panel (b) shows magnetic moment vs. temperature at a field of 1000 Oe. FIG. 19 at panel (c) shows magnetic moment v. magnetic field at 2K and 300K.

DETAILED DESCRIPTION OF CERTAIN EMBODIMENTS

Figure 1:
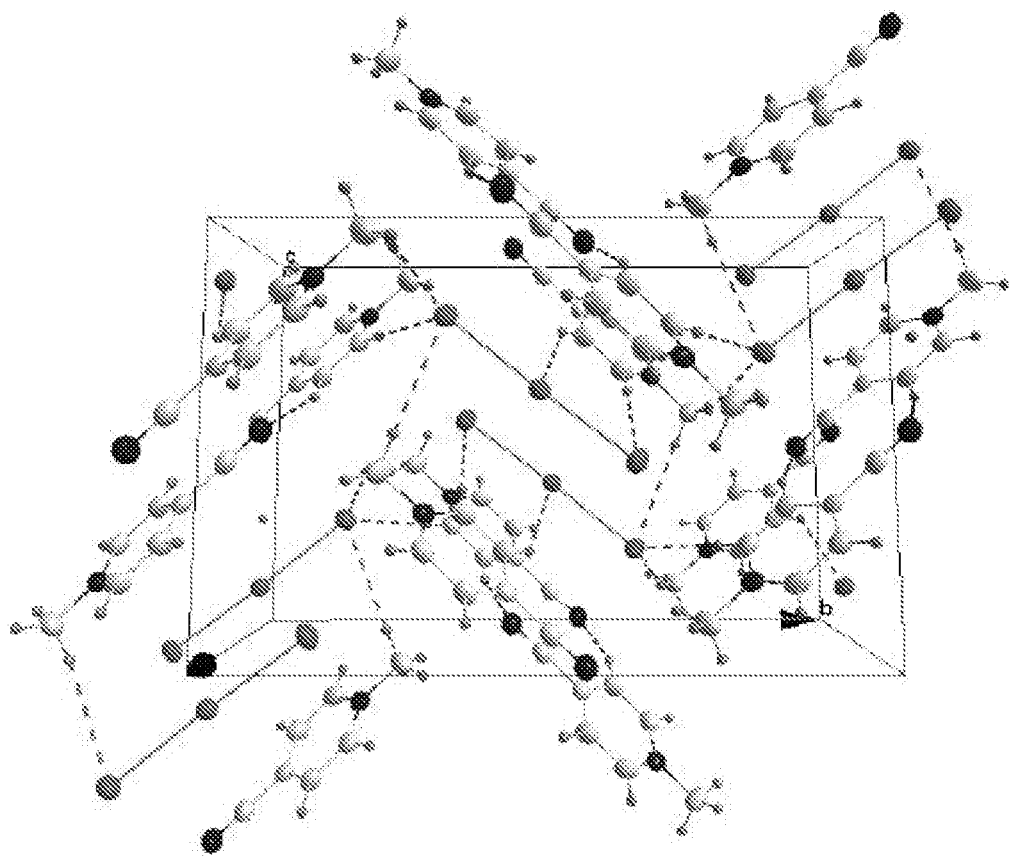
FIG. 1 illustrates a unit cell structure of 4-cyano-1-methylpyridinium triiodide, Compound I.

Various embodiments according to the present disclosure are described in detail herein. In particular, the present disclosure describes compounds and crystalline forms of compounds and methods of manufacturing and using such compounds and crystalline forms of compounds. Provided compounds and crystalline forms of compounds are particularly useful as electronic, optoelectronic, and/or semiconductor materials or devices including such materials, for example, for use as electronic materials and devices including, for example, doubling crystals, field effect transistors, lasers, liquid crystal devices, liquid crystal displays, LEDs, OFETs, OLEDs (organic light-emitting diodes) for vividly colorful displays, piezoelectrics, photonic modulators, photovoltaic cells, photovoltaics, sensors, semiconductor devices, specialized solar panels, and/or thermoelectrics. Compound I In some embodiments, provided compounds and/or crystalline forms of compounds. Such compounds include 4-cyano-1-methylpyridinium triiodide:

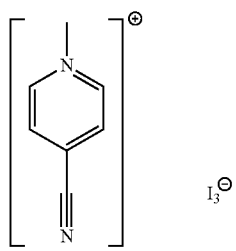

Compound I

Structure of Compound I

In some embodiments, Compound I is or includes 4-cyano-1-methylpyridinium triiodide.

In some embodiments, Compound I is present in amorphous form. In some embodiments, Compound I is present in crystalline form.

In some embodiments, Compound I is substantially free of its amorphous form. In some embodiments, Compound I is substantially free of a presence of any starting materials used in its synthesis. In some embodiments, Compound I is a crystalline solid that is substantially free of impurities.

As used herein, "substantially free" of amorphous form means that the compound contains no significant amount of its amorphous form. In some embodiments, at least about 95% by weight of crystalline Compound I is present. In some embodiments, at least about 99% by weight of crystalline Compound I is present.

In some embodiments, Compound I has a melting point of about 118° C.

In some embodiments, crystals of Compound I are flat plates.

In some embodiments, Compound I is or includes crystals that appear red. In some embodiments, crystals of Compound I appear red in transmitted light and look shiny black in reflected light.

Such optical observations have been noted for other triiodide crystals (see Johnson, J Chem Soc, 249-253 (1877); see also Chattaway, et al., J Chem Soc, Trans 654-662 (1923); see also Faust, Zeitschrift für Chemie 47-50 (1961)), so this property of Compound I is attributable to the anion.

In some embodiments, crystallographic data of Compound I are given in Table 1.

TABLE 1

| Crystallographic data Compound I | |
|---|---|
| Empirical Formula | $C_7H_7N_2I_3$ |
| CCDC number | 1430107 |
| Formula weight (g/mol) | 499.85 |
| Color, crystal shape | red, plate |
| Crystal size (mm3) | 0.178 × 0.125 × 0.060 |
| T (K) | 150(2) |
| Wavelength (Å) | 0.71073 |
| Crystal system | Monoclinic |
| Space group | P 21/n |
| a (Å) | 7.5649(6) |
| b (Å) | 15.7184(13) |
| c (Å) | 10.4723(8) |
| α (°) | 90 |
| b (°) | 98.638(1) |
| g (°) | 90 |
| V (Å3) | 1231.12(17) |
| Z | 4 |
| D (Mg/m3) | 2.697 |
| Absorption Correction | multi-scan |
| Reflections collected | 35721 |
| Unique reflections | 3235 ($R_{int}$ = 0.0407) |
| Data/restraints/parameters | 3235/0/111 |
| Final R indices | 2822 data; I > 2 ((ii)) |
| | R1 = 0.0222, wR2 = 0.0519 |
| All data | R1 = 0.0276, wR2 = 0.0540 |
| Weighting scheme | w = $1/[^2(F_o^2) + (0.0262P)^2 + 0.7229P]$ |
| where P = $(F_o^2 + 2F_c^2)/3$ | |

In some embodiments, Compound I's crystal system is monoclinic.

In some embodiments, crystal packing of Compound I is based on intersecting layers in which cations and anions alternate across a layer. In some embodiments, an axis of a triiodide anion makes an angle of 4.7° with a plane of a cation. In some embodiments, interlayer separation is 276 pm and an angle of intersection is 70°.

In some embodiments, for Compound I, selected geometries, for example, hydrogen bonds, including distances and angles are shown in Table 2.

TABLE 2

| Selected geometries in Compound I Triiodide anion bond distances and angle (pm, °) | | | | |
|---|---|---|---|---|
| I1-I2 293.86(3) | I2-I3 291.34(3) | I1-I2-I3 177.084(9) | | |
| Hydrogen-bonding interactions (pm, °) | | | | |
| D - - - H . . . A | D - - - H | H . . . A | D . . . A | D - - - H . . . A |
| C1-H1A I3[i] | 98 | 310 | 400.9(4) | 155 |
| C1-H1C I3[ii] | 98 | 317 | 400.9(4) | 160 |
| C2-H2 I3[iii] | 95 | 300 | 395.3(3) | 178 |
| C3-H3 N2[iv] | 95 | 255 | 345.1(4) | 159 |
| C5-H5 I2[v] | 95 | 315 | 388.2(3) | 135 |
| C6-H6 I1[v] | 95 | 311 | 406.2(3) | 176 |
| $r_{vdw}$ H 120 pm, N 155 pm, I 202 pm | | | | |

TABLE 2-continued

Selected geometries in Compound I
Triiodide anion bond distances and angle (pm, °)

Symmetry
operations:

i: −x, 1 − y, 1 − z;
ii: 0.5 − x, −0.5 + y,
1.5 − z;
iii: 1 − x, 1 − y, 1 − z;
iv: 1 − x, −y, 1 − z;
v: −0.5 + x, 0.5 − y,
0.5 + z.

FIG. 1 shows a unit cell of Compound I.

In some embodiments, an anion is nearly linear (177.084 (9) □) and slightly asymmetric (I—I distances 293.86(3) and 291.34(3) pm). Such geometry is well within typical range. (See Svensson, et al., 103 Chem Rev, 1649-1684 (2003); providing a review of bonding in polyiodides).

In some embodiments, each anion exhibits seven close contacts to five different cations (two are C—C contacts of 359.9(4) and 364.4(4) pm, which is less than a sum of van der Waals radii (372 pm)) while pairs of cations form hydrogen-bonded inversion dimers between a nitrile N and ring hydrogens H3/H5. In some embodiments, nitrile N also has close contacts with methyl groups on other cations. In some embodiments, both 4-cyano-1-methylpyridinium iodide and bromide salts contain similarly hydrogen-bonded cation networks as well as close contacts between ring hydrogens and anions. (See Kammer, et al., E68 Acta Cryst, 2514 (2012); see also McCormick, E69 Acta Cryst, 981 (2013); see also Nguyen, E70 Acta Cryst, 756 (2014); a substructure search of the Cambridge Crystallographic Database found a total of 13 crystal structures containing 4-cyano-1-methylpyridinium cation, no other compounds were found that show supramolecular features or crystal packing strongly resembling that of Compound I).

Figure 2:
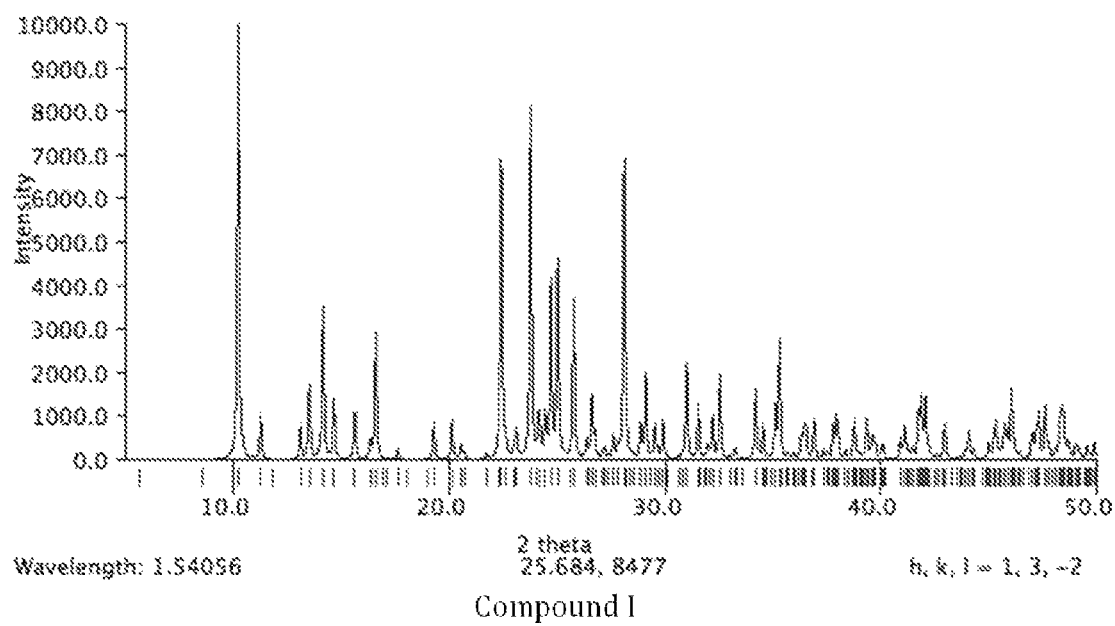
FIG. 2 shows a powder X-ray diffraction pattern of or substantially similar to that of 4-cyano-1-methylpyridinium triiodide, Compound I.

In some embodiments, a crystalline form of Compound I is characterized by a powder X-ray diffraction pattern substantially similar to that to depicted in FIG. 2.

In some embodiments, a crystalline form of Compound I is characterized by one or more peaks in its powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

In some embodiments, a crystalline form of Compound I is characterized by at least two peaks in its Powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

In some embodiments, a crystalline form of Compound I is characterized by at least three peaks in its Powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

In some embodiments, a crystalline form of Compound I is characterized by at least four peaks in its Powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

In some embodiments, a crystalline form of Compound I is characterized by at least five peaks in its Powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

In some embodiments, a crystalline form of Compound I is characterized by at least six peaks in its Powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

In some embodiments, a crystalline form of Compound I is characterized by at least seven peaks in its Powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

In some embodiments, a crystalline form of Compound I is characterized by at least eight peaks in its Powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

In some embodiments, a crystalline form of Compound I is characterized by at least nine peaks in its Powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

In some embodiments, a crystalline form of Compound I is characterized by at least ten peaks in its Powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

In some embodiments, a crystalline form of Compound I is characterized by the following eleven peaks in its Powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

Methods of forming Compound I

Salts of 4-cyano-1-methylpyridinium cation have been produced by salt metathesis (double displacement) between the 4-cyano-1-methylpyridinium iodide and more soluble silver salts containing desired anions. (See Kammer, et al., E68 Acta Cryst, 2409 (2012); see also McCormick, E69 Acta Cryst, 981 (2013); see also Nguyen, E70 Acta Cryst, 756 (2014)). However, generating 4-cyano-1-methylpyridinium chloride by this method proved difficult.

Triiodide production in aqueous reactions where air and iodide are present but molecular iodine was absent are worth noting. For example, Kosower reported visual detection of minor amounts of triiodide or iodine by the interaction of air with wet 1-methylpyridinium iodide. (See Kosower, 77 J Am Chem Soc, 3883-3885 (1955)).

Hydrothermal syntheses also generated characterizable crystalline triiodides. For example, a phase related to effective operation of certain dye-sensitized solar cells, 4-tert-butylpyridinium triiodide-4-tert-butylpyridine (1/1). (See He, et al., E67 Acta Cryst 434 (2011); see also Nazeeruddin, 115 J Am Chem Soc, 6382 (1993); see also Wang, 127 J Am Chem Soc, 6394-6401 (2005)). Additionally, a 2D coordination network of Cu(TMBP)I3 (TMBP=3,3',5,5'-tetramethyl-4,4'-bipyrazole) where triiodide acts as a cross-linking unit between Cu centers, was synthesized. (See He, et al., 54 Inorg Chem, 6087-6089 (2015)). In these synthesis, the presence of air accounts for oxidation of iodide to produce cross-linking triiodides.

Triiodide anion is typically synthesized by dissolving neutral iodine molecules in a solution containing iodide anions, such as an alkali metal salt. (See Fukui, 90 Solar Energy Materials & Solar Cells, 649-658 (2006); see also Baratz, et al, 461 Chem Phys Lett 211-217 (2008).

In some embodiments, methods of providing, preparing, and/or manufacturing compounds and/or crystalline forms of compounds of the present disclosure include synthesizing 4-cyano-1-methylpyridinium triiodide, Compound I.

The triiodide anion was generated in sufficient amounts to form Compound I in methathesis reactions between solid heavy metal chloride salts and 4-cyano-1-methylpyridinium iodide in acidified aqueous solution. Parent compound, 4-cyano-1-methylpyridinium iodide, appears yellow in color.

In some embodiments, HCl(aq) is added to inhibit hydrolysis of the nitrile group. (See Kosower, 22 Tetrahedron, 2081-2093 (1966)). In some embodiments, synthesis procedures were performed under ambient conditions, with agitation by stirring, and filtering. No molecular iodine was added. Without wishing to be bound to a particular theory, it is believed that dissolved oxygen acts as an oxidizing agent. In some embodiments, an electrochemical potential for reduction of dissolved aqueous oxygen in acidic solution is 1.23 V. In some embodiments, an oxidation of iodide to triiodide is −0.536 V. (See, for example Boschloo, 42 Acc Chem Res 1819-1826 (2009)). In some embodiments, an overall redox potential for Reaction I is favorable at about +0.7 V.

$$\tfrac{1}{2}O_2 + 2H^+ + 3I^- \rightarrow I_3^- + H_2O \qquad \text{Reaction I}$$

In addition, small particles of insoluble salts might provide catalytic surface sites.

In some embodiments, Compound I is synthesized from a reaction of $CH_3I$ and a s-triazine (a.k.a 1,3,5-triazine).

In some embodiments, Compound I is synthesized from a multistep reaction.

In some embodiments, first $CH_3I$ and 4-cyano-pyridine react to form 4-cyano-1-methylpyridinium iodide. In some embodiments, Compound I is synthesized from a reaction of 4-cyano-1-methylpyridinium iodide in water or methanol with mercury(I) chloride and/or lead(II) chloride. In some embodiments, crystals of a triiodide salt, Compound I, were obtained when reacted in an acidic aqueous solution. In some embodiments, red salts were obtained unexpectedly from yellow 4-cyano-1-methylpyridinium iodide in either water or methanol solution in contact with insoluble heavy metal chlorides under ambient conditions.

In some embodiments, such a synthesis was substantially free of 4-cyano-1-methylpyridinium chloride.

In some embodiments, red salts were obtained from yellow 4-cyano-1-methylpyridinium iodide in either water or methanol solution in contact with insoluble heavy metal chlorides under ambient conditions. In some embodiments, slow evaporation of the yellow filtrate from these reactions eventually yields flakes that appear black with reflected light and appear red when examined with transmitted light under an optical microscope.

Compound II

Numerous reports of host/guest compounds, metalloprisms or cages incorporate 2,4,6-tris(4-pyridyl)-1,3,5-triazine (usually abbreviated tpt or 4-tpt) as panels in large hexavalent (see Hafezi, et al., 54 Angew Chem Int Ed, 456-461 (2015); see also Fujita, et al., 400 Nature, 52-55 (1999); see also Gupta, E. et al., 787 J Organomet Chem, 44-50 (2015); see also Garci, 34 Organometallics, 4138-4146 (2015); see also Han et al 31 Organometallics, 995-1000 (2012)) or dodecavalent (see Kusukawa, et al., 124 J Am Chem Soc, 13576-13582 (2002)) cations (see Therrien et al., 696 J Organomet Chem, 637-651 (2011)) reviewed the coordination chemistry of 2,4,6-tri(pyridyl)-1,3,5-triazine ligands (see Mooibroek, et al., 360 Inorg Chim Acta, 381-404 (2007)) discussed in detail all the numerous possible s-triazine supramolecular interactions.

In some embodiments, triazinium iodide forms include compounds and/or crystalline forms of compounds. Such compounds include 1,1',1"-trimethyl-4,4',4"-(1,3,5-triazin-2,4,6-triyl)tripyridinium trisiodide:

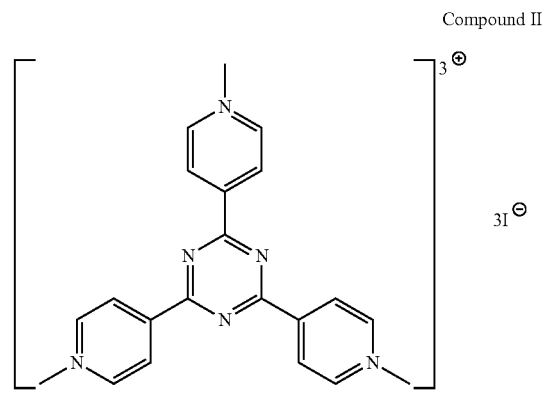

Compound II

Structure of Compound II

In some embodiments, Compound II is or includes 1,1',1"-trimethyl-4,4',4"-(1,3,5-triazin-2,4,6-triyl)tripyridinium trisiodide.

In some embodiments, Compound II is present in amorphous form.

In some embodiments, Compound II is a powder having a reddish tint.

In some embodiments, Compound II is substantially free of its amorphous form. In some embodiments, Compound II is substantially free of a presence of any starting materials used in its synthesis. In some embodiments, Compound II is a crystalline solid that is substantially free of impurities. In some embodiments, Compound II is substantially free of metals.

In some embodiments, Compound II is substantially free of Compound I.

As used herein, "substantially free" of amorphous form means that the compound contains no significant amount of its amorphous form. In some embodiments, at least about 95% by weight of crystalline Compound II is present. In some embodiments, at least about 99% by weight of crystalline Compound II is present.

In some embodiments, Compound II has a decomposition temperature of about 383° C.

In some embodiments, Compound II is air stable.

In some embodiments, Compound II is present in crystalline form. In some embodiments, crystals of Compound II have a needle shape.

In some embodiments, Compound II is or includes crystals that appear red with transmitted light. The hexafluorophosphate salt of the triazinium ion is colorless. Without wishing to be bound by a particular theory, it is believed that crystals of Compound II appear red in transmitted light is almost certainly attributable to an electronic charge-transfer transition from iodide to the trivalent cation. (See Gries, et al., Ann Chem 1021-1028 (1991)).

In some embodiments, crystals of Compound II is or includes crystals that appear shiny black with reflected light. In some embodiments, replacing I— with (PF$_6$)— results in a white compound. While not wishing to be bound, it is believed that its shiny black appearance comes from charge-transfer transitions from I— to the cation, not from electronic transitions within the pi system of the cation.

Figure 3:
FIG. 3 shows 1,1',1''-trimethyl-4,4',4''-(1,3,5-triazin-2,4,6-triyl)tripyridinium trisiodide, Compound II under reflected light.
Figure 3:
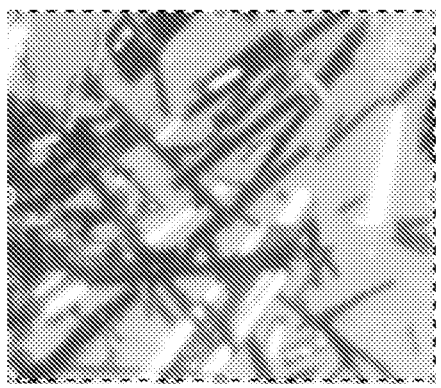
Figure 3:
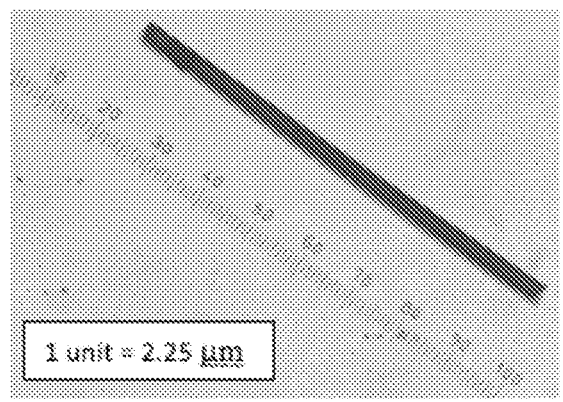

FIG. 3 shows images of 1,1',1"-trimethyl-4,4',4"-(1,3,5-triazin-2,4,6-triyl)tripyridinium trisiodide, Compound II crystals having a needle-like appearance.

In some embodiments, Compound II's crystal system is trigonal.

In some embodiments, crystallographic data of Compound II are given in Table 3.

TABLE 3

Crystallographic data Compound II

| | |
|---|---|
| Empirical Formula | $C_{21}H_{21}N_6I_3$ |
| CCDC number | 1430162, 1430163 |
| Formula weight (g/mol) | 738.14 |
| Color, crystal shape | red, needle |
| Crystal size (mm3) | 0.118 × 0.052 × 0.036 |
| T (K) | 150(2) |
| Wavelength (Å) | 0.71073 |
| Crystal system | trigonal |
| Space group | R −3 |
| a (Å) | 23.865(3) |
| b (Å) | 23.865(3) |
| c (Å) | 7.2660(9) |
| α (°) | 90 |
| b (°) | 90 |
| g (°) | 120 |
| V (Å3) | 3583.8(10) |
| Z | 6 |
| D (Mg/m3) | 2.052 |
| Absorption Correction | multi-scan |
| Reflections collected | 10708 |
| Unique reflections | 1964 (R(int) = 0.0373) |
| Data/restraints/parameters | 1964/0/92 |
| Final R indices | 1736 data; I > 2 ((II)) |
| | R1 = 0.0276, wR2 = 0.0521 |
| All data | R1 = 0.0355, wR2 = 0.0557 |
| Weighting scheme | w= $1/[^2(F_o^2) + (0.0167P)^2 + 11.5294P]$ |
| where P = $(F_o^2 + 2F_c^2)/3$ | |

In some embodiments, for Compound II, selected geometries, for example, hydrogen bonds, including distances and angles are shown in Table 4.

TABLE 4

Selected geometries in Compound II
Triazine ring distances (pm)

| | | | |
|---|---|---|---|
| Convex pair Pyridine nitrogens closest iodide (pm) | 348 | Concave pair | 379 |
| N1-I1 (convex cation, same pair) | 363 | N1-I1 (concave overhang) | 367 |
| Relative pyridine ring tilt and torsion about C4-C7(°) | | | |
| triazine centroid-C7-C4 | 176.5 | C7-C4-pyridine centroid | 176.4 |
| C3-C4-C7-N2 dihedral | 3.1, 179.6 | C5-C4-C7-N2 dihedral | 2.7, −173.8 |
| Hydrogen-bonding interactions (pm, °) | | | |

| D - - - H . . . A | D - - - H | H . . . A | D . . . A | D - - - H . . . A |
|---|---|---|---|---|
| C1-H1B I1$^i$ | 98 | 330 | 422.8(4) | 159 |
| C2-H2 I1$^i$ | 95 | 319 | 404.3(3) | 150 |
| C3-H3 I1$^{ii}$ | 95 | 317 | 405.6(3) | 156 |
| C5-H5 I1$^{iii}$ | 95 | 304 | 386.4(4) | 146 |
| C6-H6 I1$^{iv}$ | 95 | 318 | 410.2(3) | 163 |

$r_{vdw}$ H 120 pm, N 155 pm, I 202 pm
Symmetry operations:

i: −x, 1 − y, 1 − z;
ii 0.3333 + y, 0.6667 − x − y, 0.6667 − z;
iii: 0.3333 + x − y,

TABLE 4-continued

Selected geometries in Compound II
Triazine ring distances (pm)

0.3333 + x, 0.6667 − z;
iv: 0.3333 + y, 0.6667 − x − y, 0.6667 − z;

In some embodiments, Compound II has or includes a columnar structure. In some embodiments, Compound II has its cations arranged in columns with I— around the edges and between concave pairs. In some embodiments, Compound II's columnar structure, appears similar to organic conductors, for example, charge-transfer salts, such as TCNQ TTF.

Figure 4:
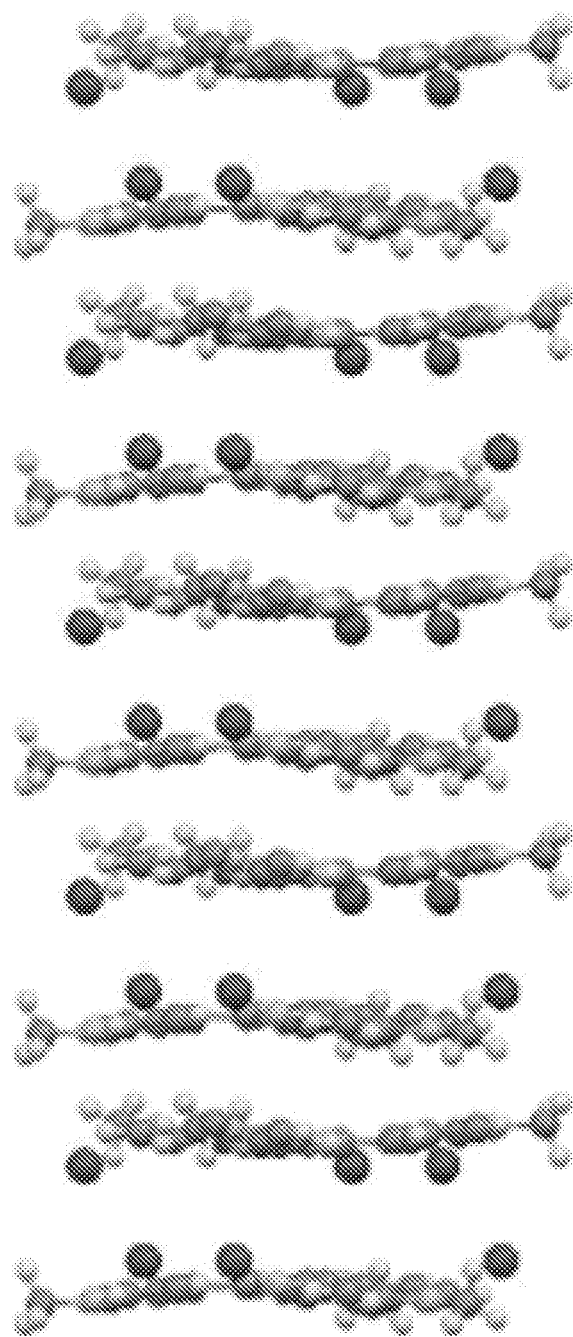
FIG. 4 shows side view pi stacking of the trivalent cations, three anions associated with each one for 1,1',1''-trimethyl-4,4',4''-(1,3,5-triazin-2,4,6-triyl)tripyridinium trisiodide, Compound II.

FIG. 4 shows 1,1',1"-trimethyl-4,4',4"-(1,3,5-triazin-2,4,6-triyl)tripyridinium trisiodide, Compound II. In particular, FIG. 4 shows a side view of pi stacking of trivalent cations, three anions associated with each one of Compound II. As portrayed in FIG. 4, Compound II shows a closest distance between ring centroids of about 3.48 Å.

Figure 5:
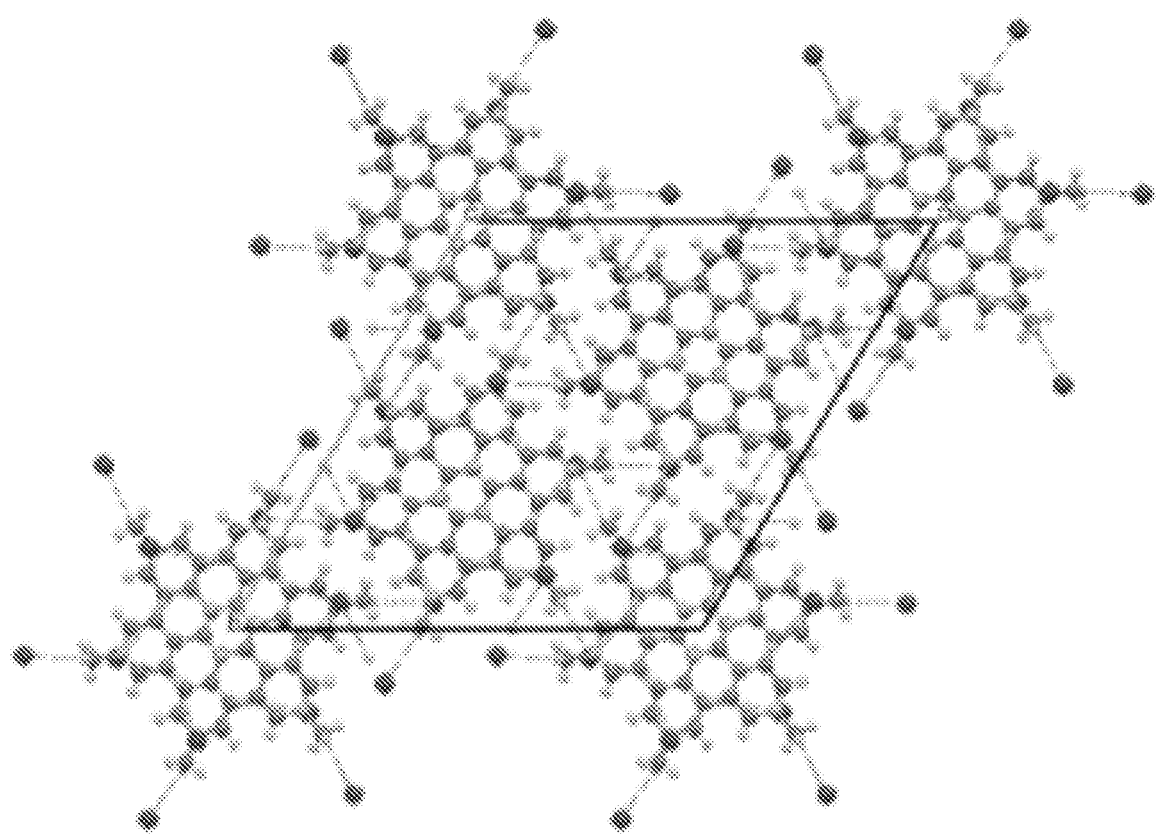
FIG. 5 shows a unit cell of 1,1',1''-trimethyl-4,4',4''-(1,3,5-triazin-2,4,6-triyl)tripyridinium trisiodide, Compound II from a perspective along it c axis, a and b axes plane.

FIG. 5 shows a view along a c axis of a unit cell of 1,1',1"-trimethyl-4,4',4"-(1,3,5-triazin-2,4,6-triyl)tripyridinium trisiodide, Compound II. An a and b axes in plane, cross section of columns. Dotted lines shown in FIG. 5 depict C—H . . . I hydrogen bonds. As shown in FIG. 5, gray spheres are carbon, blue spheres are nitrogen, white spheres are hydrogen, and purple spheres are iodide.

In some embodiments, trivalent triazinium cation [CAS 135973-20-5] of Compound II [CAS 42517-85-1] display four different oxidation states, including a diradical, all with half-wave potentials between −0.28 and −1.46 V vs. Ag/AgCl in 0.1 M n-butylammonium tetrafluoroborate acetonitrile solution. (See Ann Chem 1021-1028 (1991)). The iodide salt is also named as a herbicide (see German Patent Publication DE 2262188 A1) and more recently as a reagent for the manufacture of nitrogen-containing carbon alloys (see International Patent Publication WO 2014208740 A1) but little other mention of this cation can be found in the literature. (See Bauer, et al., 18 Int J Hydrogen Energy, 205-210 (1993)).

In some embodiments, crystal structures of Compound II feature staggered pi stacking of shallow cation bowls in columns of alternating prone and supine orientations with perfectly aligned centroids.

Figure 6:
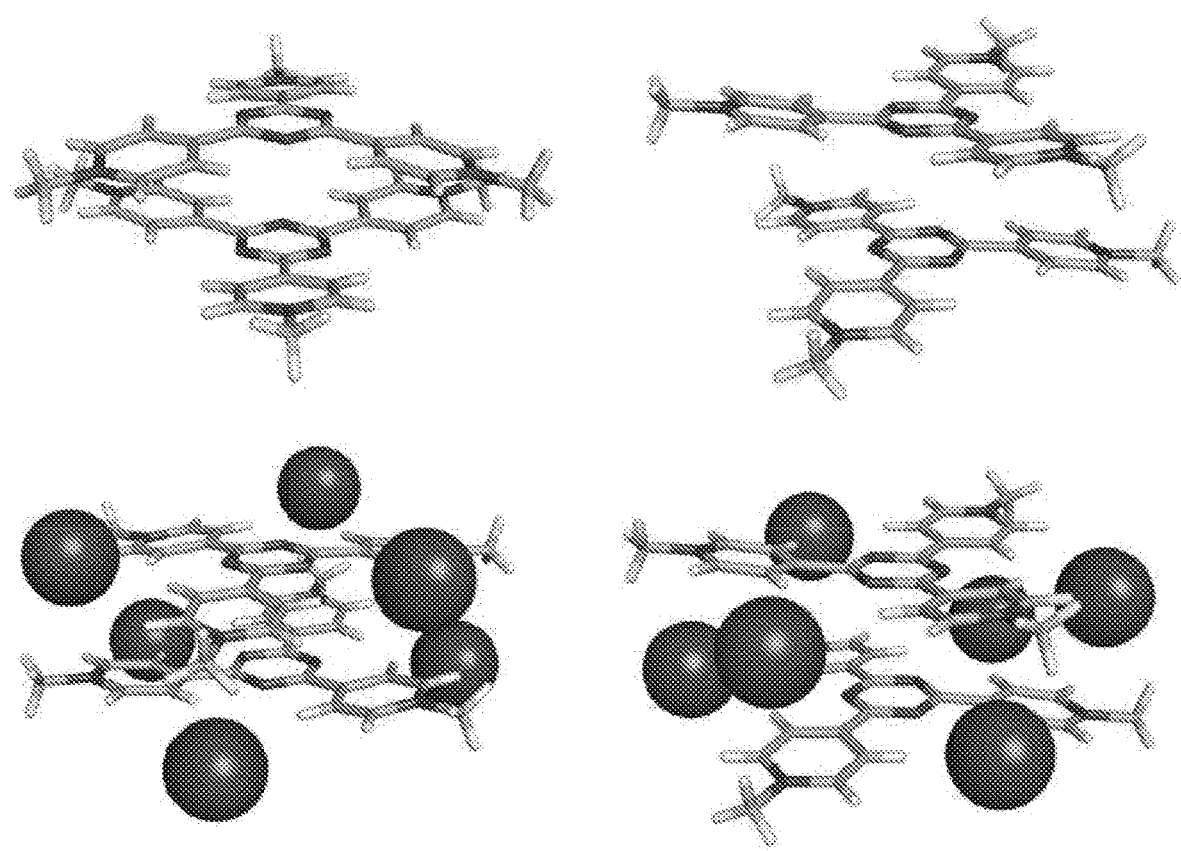
FIG. 6 shows cation pairs of 1,1',1"-trimethyl-4,4',4"-(1,3,5-triazin-2,4,6-triyl)tripyridinium trisiodide, Compound II with and without anions.
Figure 7:
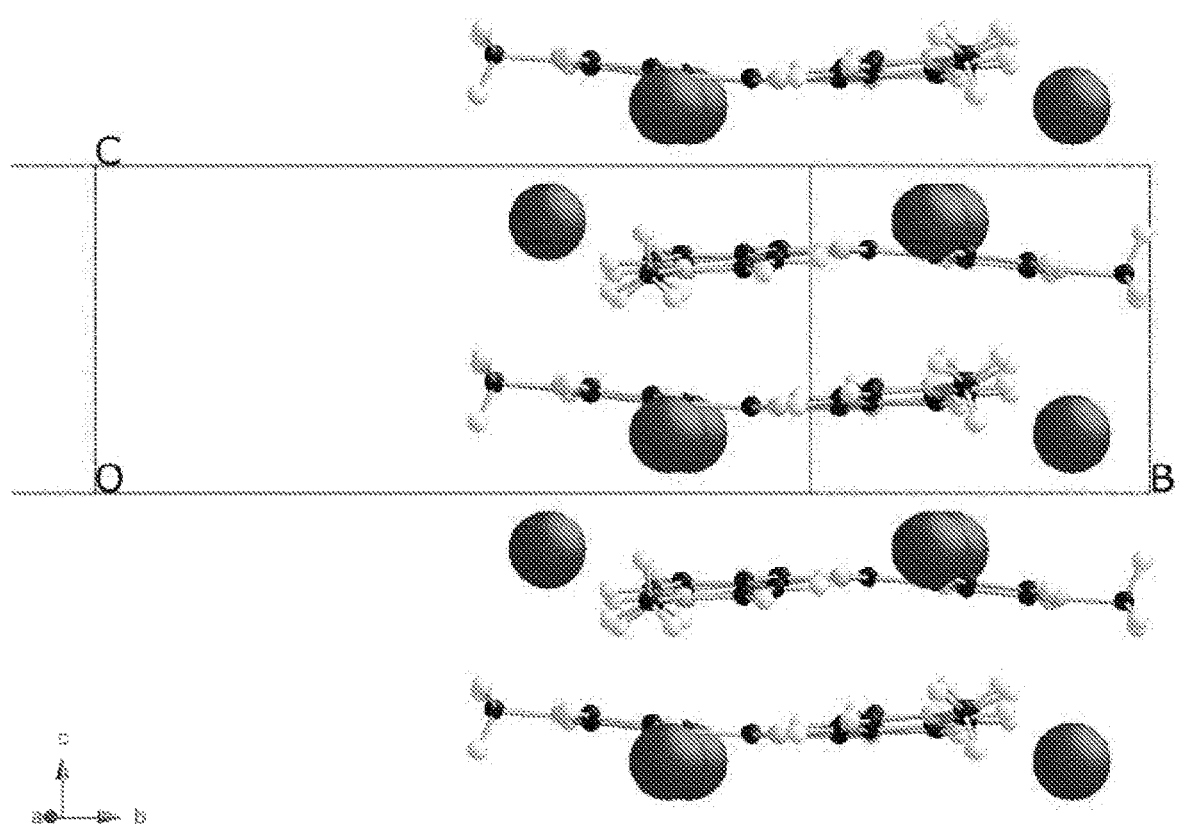
FIG. 7 shows a side view of a column of alternating convex and concave cation pairs in 1,1',1"-trimethyl-4,4',4"-(1,3,5-triazin-2,4,6-triyl)tripyridinium trisiodide, Compound II with iodide anions between concave pairs.
Figure 8:
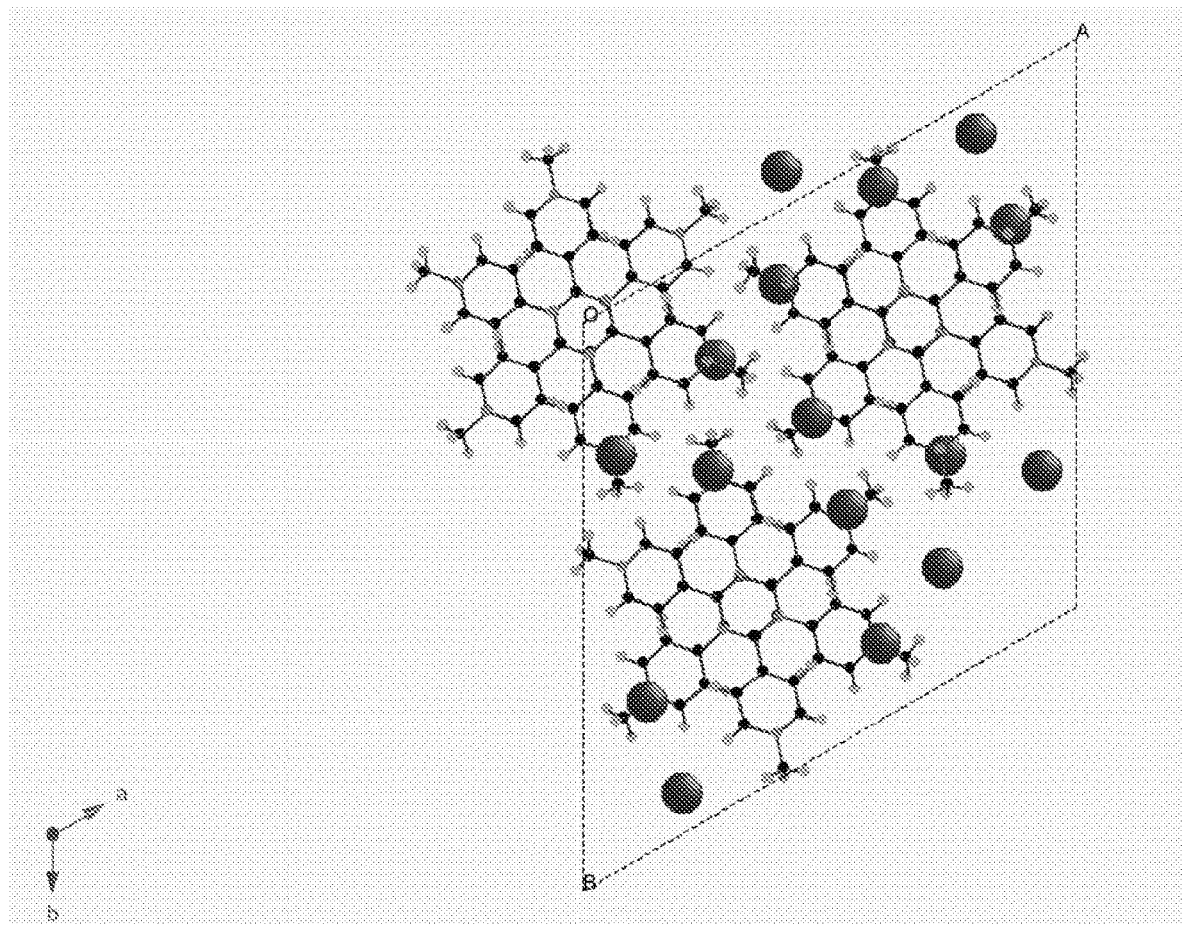
FIG. 8 shows a perspective of a top view of columns of 1,1',1"-trimethyl-4,4',4"-(1,3,5-triazin-2,4,6-triyl)tripyridinium trisiodide, Compound II.

FIGS. 6-8 show cation pairs with and without anions, a side view of a column of alternating cation pairs with anions, and a view down the crystallographic c axis.

FIG. 6 shows cation pairs with and without anions. A side view of a column of alternating cation pairs with anions, and a view down the crystallographic c axis. Convex (left) and concave (right) cation pairs and octamers (cation pair plus six anions) of 1,1',1"-trimethyl-4,4',4"-(1,3,5-triazin-2,4,6-triyl)tripyridinium trisiodide, Compound II are shown.

FIG. 7 shows a side view of a column of alternating convex and concave cation pairs in 1,1',1"-trimethyl-4,4',4"-(1,3,5-triazin-2,4,6-triyl)tripyridinium trisiodide, Compound II with iodide anions between concave pairs. The crystal structure of Compound II features staggered pi stacking of shallow cation bowls in columns of alternating prone and supine orientations with perfectly aligned centroids.

In some embodiments, columns in Compound II can be viewed as consisting of stacks of pairs of cations with the insides of the bowls facing toward each other (convex, bowed outward from the empty center) alternating with pairs facing away from each other (concave with bowl bottoms closer than bowl edges, iodides between the outer parts of the bowls) as shown in FIG. 7. In some embodiments, distances between the triazine ring centroids is 348 pm for convex pairs and 379 pm for concave pairs. (See Table 3).

FIG. 8 shows a perspective of a top view of columns of 1,1',1"-trimethyl-4,4',4"-(1,3,5-triazin-2,4,6-triyl)tripyridinium trisiodide, Compound II shown in FIG. 7. Columns are rotated 90 degrees forward to show an arrangement of iodides around cation edges. A crystallographic c axis points out of a plane of the page. Cation pairs are aligned like beads on strings through ring centroids parallel to a crystallographic c axis.

In some embodiments, cation bowls are closer for pairs where the empty insides of the bowls face each other. In some embodiments, a sum of these two ring centroid distances, 727 pm, is almost exactly twice the distance between rings in 1,3,5-triazine, 364 pm. (See Wheatley, 8 Acta Cryst, 224 (1955)). In some embodiments, as shown in FIG. 8, when viewed down a c axis of its unit cell, each adjacent pair together resembles a snowflake.

In some embodiments, pendant pyridine rings are bent up toward the central triazine ring. In some embodiments, pendant rings are also rotated very slightly about the C4-C7 bond such that C3 is down while C5 is up or vice versa. In some embodiments, a propeller conformation such as this imposes C3 point group symmetry upon the cations making them chiral. In some embodiments, cation handedness alternates along with prone and supine orientations along each column. In some embodiments, every cation is rotated by 60 degrees relative to the ones directly below and above it such that all triazine nitrogen atoms are sandwiched between triazine carbon atoms on the two closest cations, and vice versa.

In some embodiments, triazine cores of cations exhibit face-to-face [σ-σ]2 stacking where the ring offset, r, is 0, the torsion angle around the ring centroid, β is 60° and the relative triazine ring plane tilt angle, α, is 0°. (See Mooibroek, et al., 360 Inorg Chim Acta, 381-404 (2007)). In some embodiments, this configuration is stable with respect to pi interactions of two s-triazine rings. (See Mooibroek, et al., 360 Inorg Chim Acta, 381-404 (2007)). In some embodiments, face-to-face stacking is observed in white crystalline 1,3,5-triazine, n.m.pt. 80° C. (see Wheatley, 8 Acta Cryst, 224 (1955)) where the crystal structure is similar to that of Compound II.

In some embodiments, all cation pairs are perfectly aligned like beads on strings through the ring centroids parallel to the crystallographic c axis. In contrast, almost all of the hexavalent cage cations (see Fujita, et al., 400 Nature, 52-55 (1999); see also Gupta, E. et al., 787 J Organomet Chem, 44-50 (2015); see also Garci, 34 Organometallics, 4138-4146 (2015); see also Han et al 31 Organometallics, 995-1000 (2012)) hold two 4-tpt panels tethered to each other in an eclipsed formation (r and β both close to 0) where the panels bow inward toward the cage center. BlueCage$^{6+}$ (see Hafezi, et al., 54 Angew Chem Int Ed, 456-461 (2015)) is one example where tethered panels bow outward. In both BlueCage$^{6+}$ and an interlocked cage complex (see Fujita, et al., 400 Nature, 52-55 (1999)), bottom-facing bowls of adjacent cages or interlocked panels exhibit the favored β=60° rotation.

In some embodiments, every cation pair in Compound II has six closely associated iodide anions. In some embodiments, they are located just outside the bowl edges with most of the anion body between bottom-facing concave pairs. In some embodiments, iodides are in the notches between pyridine rings with close contacts to two ring hydrogens (I—H5 304 pm, I—H3 317 pm). In some embodiments, all iodides are equivalent in this structure and each has five hydrogen-bonding interactions. In some embodiments, an additional close contact to a methyl group from an adjacent column (H1A-I 315 pm, C—H—I 121°) is probably important in stabilizing the overall structure. In some embodiments, iodide anions are also close to presumably electron-poor quaternized pyridine nitrogens in the overhanging groups of adjacent convex (I—N 363 pm) and concave (I—N 367 pm) cations. (See Table 4). In some embodiments, hexafluorophosphate anions in coronene BlueCage.6PF6 crystals are in essentially the same positions relative to the pyridine nitrogens and the packing along the crystallographic c axis resembles the columns found in Compound II. As BlueCage.6PF6 has one anion inside the cage rather than a coronene guest molecule, only four of the six anions are close to pyridine nitrogens, leading to very different crystal packing. (See Hafezi, et al., 54 Angew Chem Int Ed, 456-461 (2015)).

In some embodiments, compounds and crystalline forms of compounds as disclosed herein possess liquid crystalline character. In some embodiments, compounds and crystalline forms of compounds as disclosed herein that possess such liquid crystalline character are useful in forming devices and displays. (See for example Jiao et al., "Synthesis and mesophases of $C_{3h}$-symmetric 2,4,6-tris(2-hydroxyphenyl)-1,3,5-triazine derivatives with intramolecular hydrogen bonding networks", 56 Tetrahedron Letters, 5185-5189 (2015); see also for example, Chen et al, "Ionic Discotic Liquid Crystals", 52 Israel J. Chemistry, 830-843 (2012)).

Figure 9:
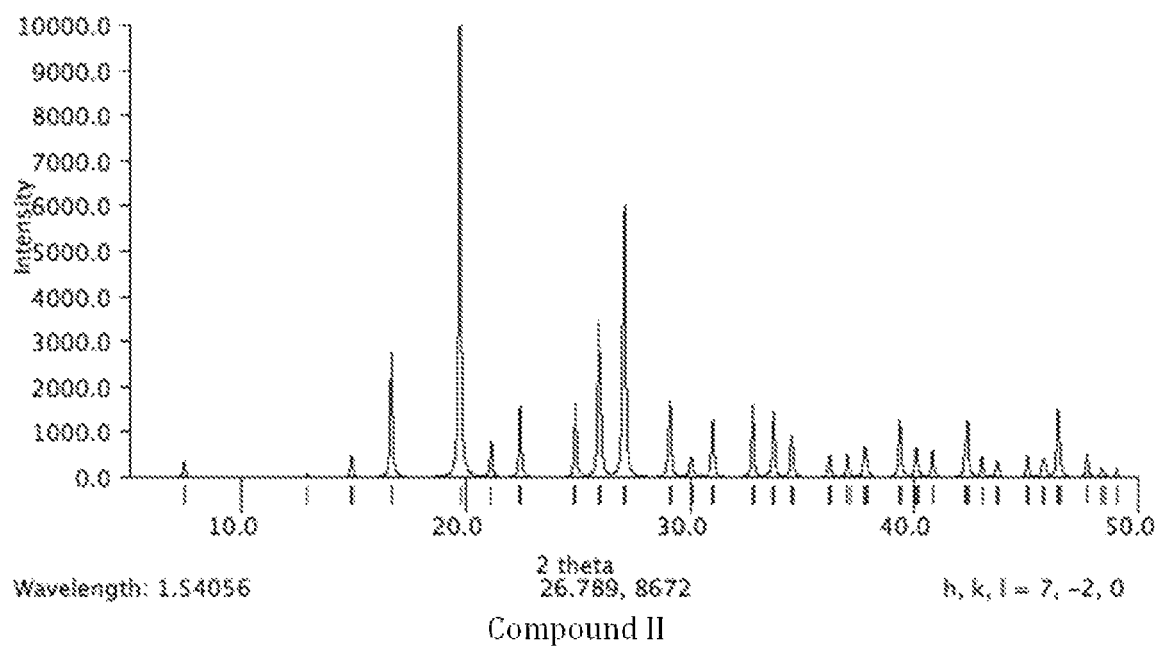
FIG. 9 shows a powder X-ray diffraction pattern of or substantially similar to that of 1,1',1"-trimethyl-4,4',4"-(1,3,5-triazin-2,4,6-triyl)tripyridinium trisiodide, Compound II.

In some embodiments, a crystalline form of Compound II is characterized by a powder X-ray diffraction pattern substantially similar to that to depicted in FIG. 9.

In some embodiments, a crystalline form of Compound II is characterized by one or more peaks in its powder X-ray diffraction pattern selected from those at about 10.22, about 14.14, about 16.6, about 22.4, about 23.78, about 24.7, about 25.02, about 25.78, about 28.1, about 31, or about 35.3 degrees 2-theta.

In some embodiments, a crystalline form of Compound II is characterized by one or more peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

In some embodiments, a crystalline form of Compound II is characterized by at least two peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

In some embodiments, a crystalline form of Compound II is characterized by at least three peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

In some embodiments, a crystalline form of Compound II is characterized by at least four peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

In some embodiments, a crystalline form of Compound II is characterized by at least five peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

In some embodiments, a crystalline form of Compound II is characterized by at least six peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

In some embodiments, a crystalline form of Compound II is characterized by at least seven peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

In some embodiments, a crystalline form of Compound II is characterized by at least eight peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

In some embodiments, a crystalline form of Compound II is characterized by at least nine peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

In some embodiments, a crystalline form of Compound II is characterized by the following ten peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

Methods of Forming Compound II

In some embodiments, methods of providing, preparing, and/or manufacturing compounds and/or crystalline forms of compounds of the present disclosure include synthesizing 1,1',1"-trimethyl-4,4',4"-(1,3,5-triazin-2,4,6-triyl)tripyridinium trisiodide, Compound II.

In some embodiments, Compound II is or includes a crystalline form of a trivalent triazinium salt. In some embodiments, such crystalline forms are synthesized by a cyclotrimerization of 4-cyano-1-methylpyridinium iodide.

In some embodiments, a cyclotrimerization of 4-cyano-1-methylpyridinium form a trivalent triazine cation. In some embodiments, synthesis of a trivalent triazine cation via cyclotrimerization occurs under mild conditions including Lewis acid catalysts and alcohol solvent.

In some embodiments, crystals of halide salts were obtained by slow evaporation.

In some embodiments, crystals are characterized by single crystal X-ray diffraction, 1H-NMR spectroscopy along with a computational study of the gas-phase cation, and interaction energies for cation pairs and associated anions for triazinium compound.

In some embodiments, red salts were unexpectedly obtained from yellow 4-cyano-1-methylpyridinium iodide in either water or methanol solution in contact with insoluble heavy metal chlorides under ambient conditions.

In some embodiments, methods of providing, preparing, and/or manufacturing compounds and/or crystalline forms of compounds of the present disclosure include synthesizing 1,1',1''-trimethyl-4,4',4''-(1,3,5-triazin-2,4,6-triyl)tripyridinium trisiodide, Compound II under ambient conditions, by contacting an acidic aqueous solutions of 4-cyano-1-methylpyridinium iodide with insoluble heavy metal chloride solids.

In some embodiments, without wishing to be bound to a specific theory, it is believed that an electron transfer reaction takes place to form red 4-cyano-1-methylpyridinium triiodide, containing the linear triatomic anion (Compound I).

In some embodiments, while attempting to use anion exchange to generate crystals of 4-cyano-1-methylpyridinium chloride, a same experiment was repeated using methanol as the solvent. In some embodiments, a red product is obtained.

In some embodiments, upon examination with an optical microscope, a red product is shown to be composed of red needles. In some embodiments, red needles were shown as grown in clumps attached to clear plates. In some embodiments, clear plates were determined by single crystal X-ray diffraction analysis to be 4-carbamido-1-methylpyridinium iodide. 4-carbamido-1-methylpyridinium iodide is the undesired hydrolysis product. (See Kosower, 22 Tetrahedron, 2081-2093 (1966)).

Surprisingly, the red needles were found to be 1,1',1''-trimethyl-4,4',4''-(1,3,5-triazin-2,4,6-triyl)tripyridinium trisiodide, Compound II.

In some embodiments, when 4-cyano-1-methylpyridinium triiodide, Compound I is contacted with methanol, cyclotrimerization yields 1,1',1''-trimethyl-4,4',4''-(1,3,5-triazin-2,4,6-triyl)tripyridinium trisiodide with three monatomic anions per trivalent cation (Compound II).

In some embodiments, Compound II is formed from a cyclotrimerization of 4-cyano-1-methylpyridinium iodide. In some embodiments, Compound II is formed from a methanol solution under ambient conditions.

In some embodiments, cyclotrimerization of 4-cyano-1-methylpyridinium iodide using $Hg_2Cl_2$ as catalyst in methanol provides a route to create s-triazine molecules.

In some embodiments, a ratio of $Hg_2Cl_2$ catalyst to 4-cyano-1-methylpyridinium iodide affects a cyclotrimerization reaction rate. In some embodiments, for example, using an equimolar amount of catalyst significantly speeds up a cyclotrimerization process when compared to using a catalytic amount of catalyst. In some embodiments, a cyclotrimerization reaction occurs in a step-wise manner.

In some embodiments, methods of providing, preparing, and/or manufacturing compounds and/or crystalline forms of compounds of the present disclosure include synthesizing 1,1',1''-trimethyl-4,4',4''-(1,3,5-triazin-2,4,6-triyl)tripyridinium trisiodide, Compound II, by dissolving 2,4,6-tris-(4-pyridyl)-1,3,5-triazine in dimethylformamide and then adding methyl iodide.

Trivalent 1,3,5-triazinium Cation Based Compounds

In some embodiments, other compounds and crystalline forms of compounds containing trivalent 1,3,5-triazinium cations are disclosed.

Compound III

In some embodiments, triazinium iodide forms include compounds and/or crystalline forms of compounds. Such compounds include 1,1',1''-triethyl-3,3',3''-(1,3,5-triazin-2,4,6-triyl)tripyridinium trisiodide, 3-teptI, Compound III.

In some embodiments, an I— of 1,1',1''-triethyl-3,3',3''-(1,3,5-triazin-2,4,6-triyl)tripyridinium trisiodide, 3-teptI, Compound III, is in a similar position to that of Compound II. In some embodiments, an ethyl group is attached to N in position 3 of 1,1',1''-triethyl-3,3',3''-(1,3,5-triazin-2,4,6-triyl)tripyridinium trisiodide, 3-teptI, Compound III.

In some embodiments, 1,1',1''-triethyl-3,3',3''-(1,3,5-triazin-2,4,6-triyl)tripyridinium trisiodide, 3-teptI, Compound III has a Piedfort unit motif. In some embodiments, 1,1',1''-triethyl-3,3',3''-(1,3,5-triazin-2,4,6-triyl)tripyridinium trisiodide, 3-teptI, Compound III has two cations face-to-face rotated 60 degrees. In some embodiments, 1,1',1''-triethyl-3,3',3''-(1,3,5-triazin-2,4,6-triyl)tripyridinium trisiodide, 3-teptI, Compound III shows similar pairs of cations but does not stack in columns.

Figure 10:
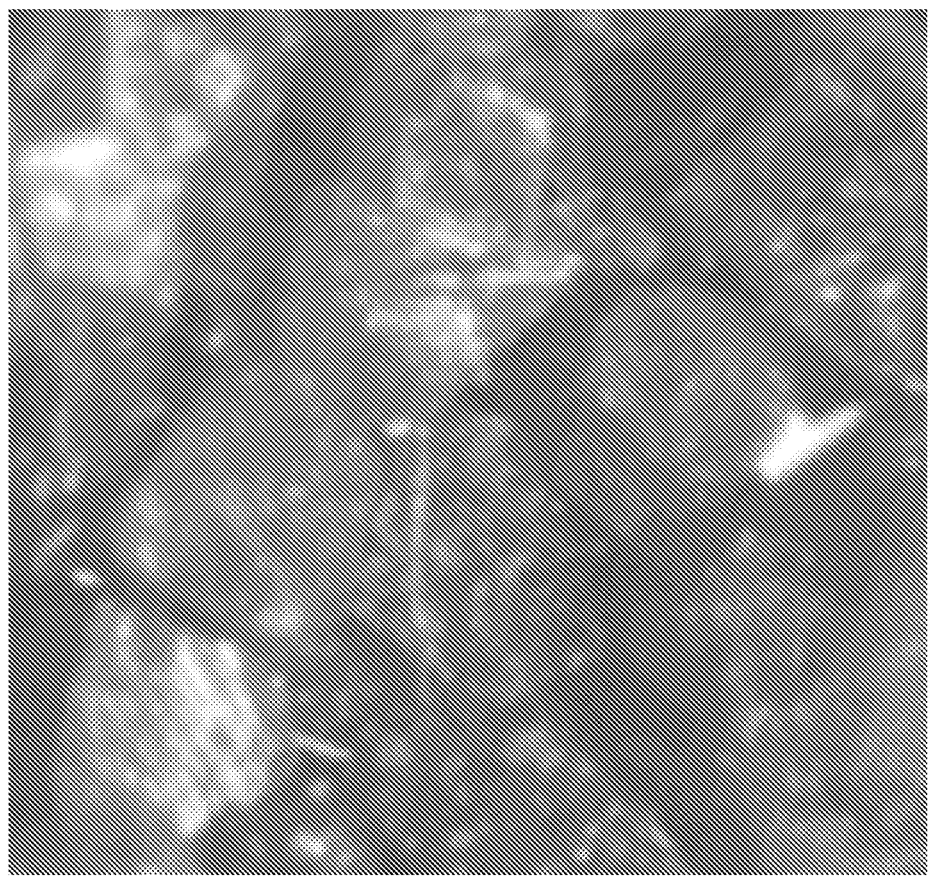
FIG. 10 shows blocky orange-red crystals of 1,1',1"-triethyl-3,3',3"-(1,3,5-triazin-2,4,6-triyl)tripyridinium trisiodide, 3-teptI, Compound III.

In some embodiments, 1,1',1''-triethyl-3,3',3''-(1,3,5-triazin-2,4,6-triyl)tripyridinium trisiodide, 3-teptI, Compound III is colored a shade of dark red to bright orange. FIG. 10 shows a 1,1',1''-triethyl-3,3',3''-(1,3,5-triazin-2,4,6-triyl) tripyridinium trisiodide, 3-teptI, Compound III. 1,1',1''-triethyl-3,3',3''-(1,3,5-triazin-2,4,6-triyl)tripyridinium trisiodide, 3-teptI, Compound III is depicted in FIG. 10 as having blocky orange-red crystals in reflected light.

Figure 11:
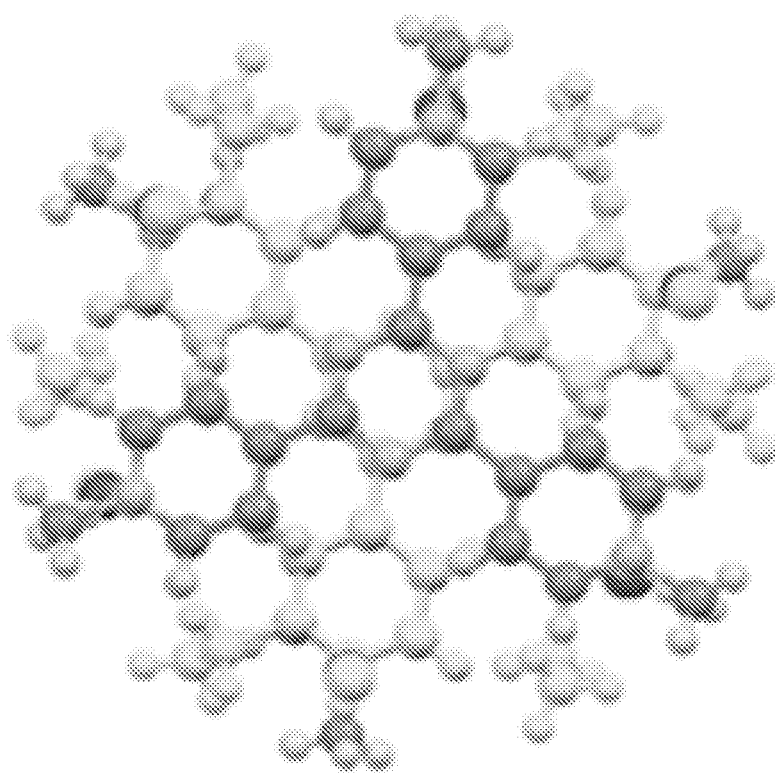
FIG. 11 shows 1,1',1"-triethyl-3,3',3"-(1,3,5-triazin-2,4,6-triyl)tripyridinium trisiodide, 3-teptI, Compound III overlaid with 1,1',1"-trimethyl-4,4',4"-(1,3,5-triazin-2,4,6-triyl)tripyridinium trisiodide, Compound II.

FIG. 11 shows 1,1',1''-triethyl-3,3',3''-(1,3,5-triazin-2,4,6-triyl)tripyridinium trisiodide, 3-teptI, Compound III (shown in yellow) overlaid with 1,1',1''-trimethyl-4,4',4''-(1,3,5-triazin-2,4,6-triyl)tripyridinium trisiodide, Compound II (gray, blue, white, purple) showing correspondence along crystallographic c axis, ethyl group in 3 position.

Figure 12:
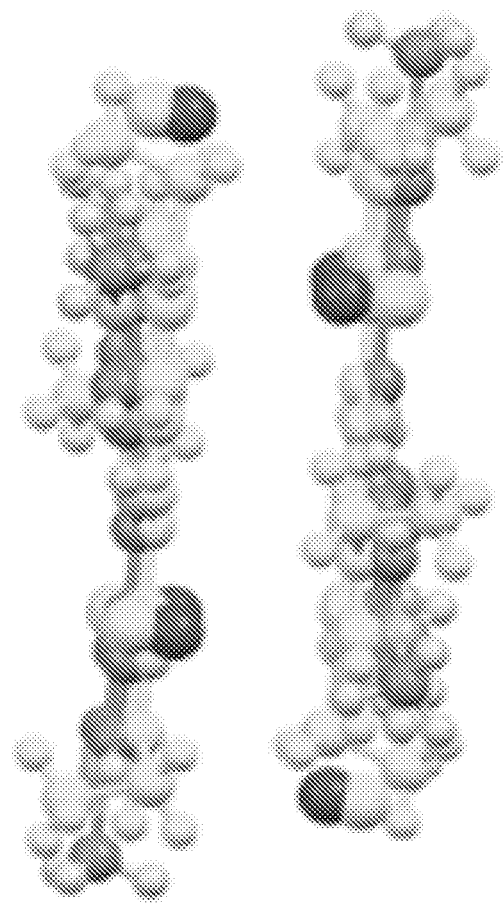
FIG. 12 shows 1,1',1"-triethyl-3,3',3"-(1,3,5-triazin-2,4,6-triyl)tripyridinium trisiodide, 3-teptI, Compound III compared alongside 1,1',1"-trimethyl-4,4',4"-(1,3,5-triazin-2,4,6-triyl)tripyridinium trisiodide, Compound II.

FIG. 12 shows a comparison along b axis showing one Piedfort unit. Note coincidence of iodide positions except that they are in plane with 3-tept3+ cations of 1,1',1''-triethyl-3,3',3''-(1,3,5-triazin-2,4,6-triyl)tripyridinium trisiodide, 3-teptI, Compound III while they are between the 4-tmpt3+ ions of 1,1',1''-trimethyl-4,4',4''-(1,3,5-triazin-2,4,6-triyl)tripyridinium trisiodide, Compound II.

Figure 13:
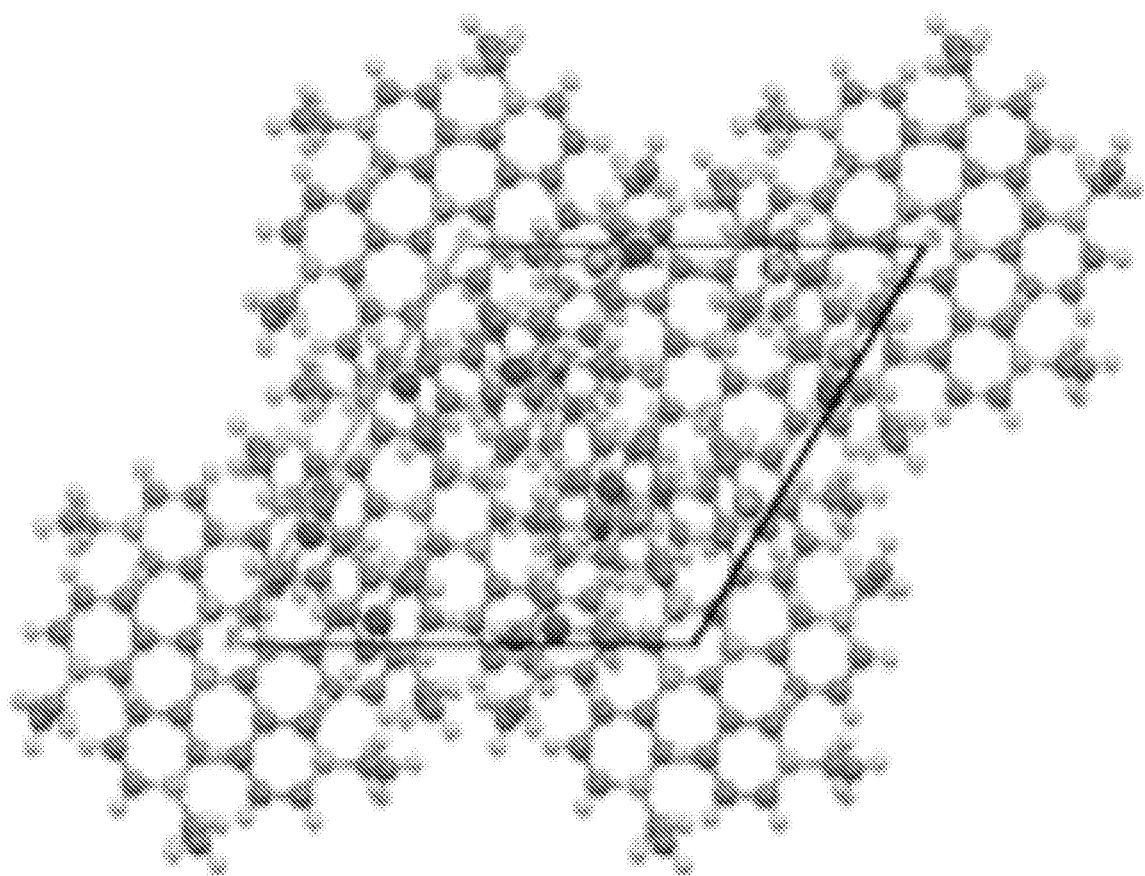
FIG. 13 shows 1,1',1"-triethyl-3,3',3"-(1,3,5-triazin-2,4,6-triyl)tripyridinium trisiodide, 3-teptI, Compound III along a c axis of its unit cell.

FIG. 13 shows a comparison of 1,1',1''-triethyl-3,3',3''-(1,3,5-triazin-2,4,6-triyl)tripyridinium trisiodide, 3-teptI, Compound III and 1,1',1''-trimethyl-4,4',4''-(1,3,5-triazin-2,4,6-triyl)tripyridinium trisiodide, Compound II, along a c axis of a unit cell.

Compound IV

In some embodiments, triazinium iodide forms include compounds and/or crystalline forms of compounds. Such compounds include: 1,1',1''-trimethyl-2,2',2''-(1,3,5-triazin-2,4,6-triyl)tripyridinium trisiodide, 2-tmptI, Compound IV. In some embodiments, 1,1',1''-trimethyl-2,2',2''-(1,3,5-triazin-2,4,6-triyl)tripyridinium trisiodide, 2-tmptI, Compound IV is a positional isomer.

In some embodiments, a methyl group attached to N of 2-tmptI. In some embodiments, a methyl group attached to N of 2-tmptI is rotated such that it's in the 2 rather than 4 position relative to attachment to central ring. In some embodiments, pyridine rings are twisted/canted relative to central triazine ring of 2-tmptI.

In some embodiments, 2-tmptI is colored a shade of dark red to bright orange.

Figure 24:
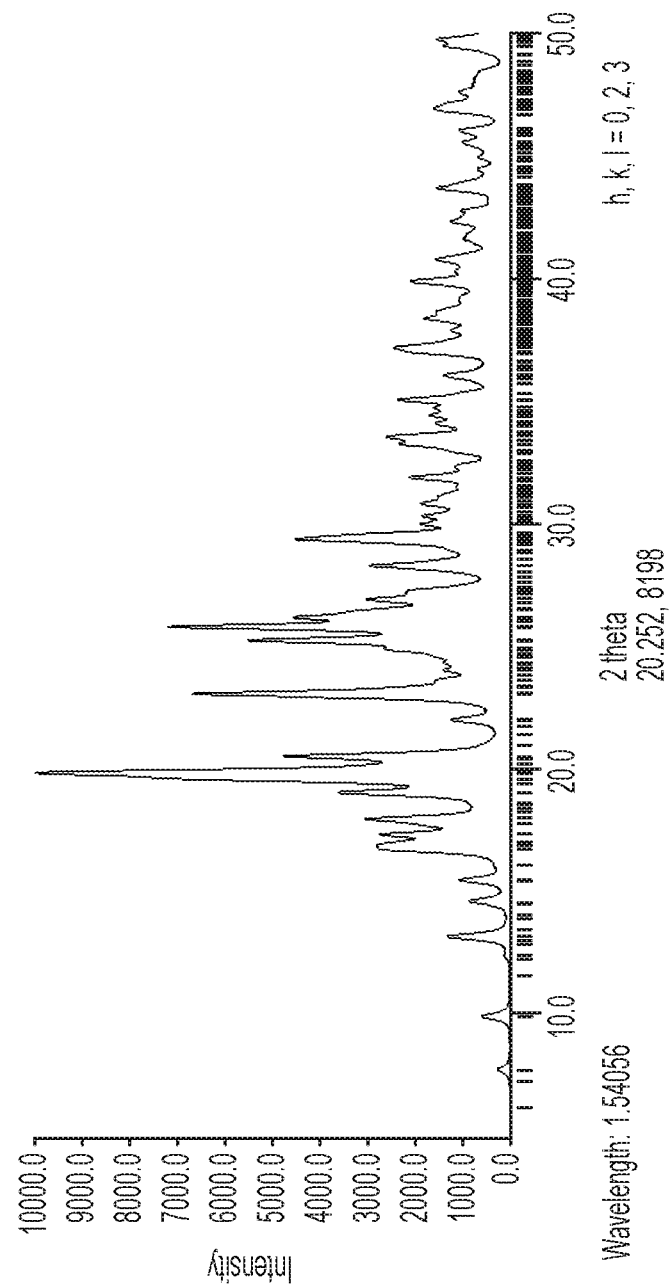
FIG. 24 shows a powder X-ray diffraction pattern of or substantially similar to that of 1,1',1"-trimethyl-2,2',2"-(1,3,5-triazin-2,4,6-triyl)tripyridinium trisiodide, 2-tmptI, Compound IV.

In some embodiments, a crystalline form of 1,1',1''-trimethyl-2,2',2''-(1,3,5-triazin-2,4,6-triyl)tripyridinium trisiodide, 2-tmptI, Compound IV is characterized by a powder X-ray diffraction pattern substantially similar to that to depicted in FIG. 24.

In some embodiments, a crystalline form of Compound IV is characterized by one or more peaks in its powder X-ray diffraction pattern selected from those at about 17.96, about 19.04, about 19.60, about 19.86, about 20.52, about 23.06, about 25.26, about 25.8, about 28.28, or about 29.37 degrees 2-theta.

In some embodiments, a crystalline form of Compound IV is characterized by one or more peaks in its Powder X-ray diffraction pattern selected from those at about 17.96, about 19.04, about 19.60, about 19.86, about 20.52, about 23.06, about 25.26, about 25.8, about 28.28, or about 29.37 degrees 2-theta.

In some embodiments, a crystalline form of Compound IV is characterized by at least two peaks in its Powder X-ray diffraction pattern selected from those at about 17.96, about 19.04, about 19.60, about 19.86, about 20.52, about 23.06, about 25.26, about 25.8, about 28.28, or about 29.37 degrees 2-theta.

In some embodiments, a crystalline form of Compound IV is characterized by at least three peaks in its Powder X-ray diffraction pattern selected from those at about 17.96, about 19.04, about 19.60, about 19.86, about 20.52, about 23.06, about 25.26, about 25.8, about 28.28, or about 29.37 degrees 2-theta.

In some embodiments, a crystalline form of Compound IV is characterized by at least four peaks in its Powder X-ray diffraction pattern selected from those at about 17.96, about 19.04, about 19.60, about 19.86, about 20.52, about 23.06, about 25.26, about 25.8, about 28.28, or about 29.37 degrees 2-theta.

In some embodiments, a crystalline form of Compound IV is characterized by at least five peaks in its Powder X-ray diffraction pattern selected from those at about 17.96, about 19.04, about 19.60, about 19.86, about 20.52, about 23.06, about 25.26, about 25.8, about 28.28, or about 29.37 degrees 2-theta.

In some embodiments, a crystalline form of Compound IV is characterized by at least six peaks in its Powder X-ray diffraction pattern from those at about 17.96, about 19.04, about 19.60, about 19.86, about 20.52, about 23.06, about 25.26, about 25.8, about 28.28, or about 29.37 degrees 2-theta.

In some embodiments, a crystalline form of Compound IV is characterized by at least seven peaks in its Powder X-ray diffraction pattern selected from those at about 17.96, about 19.04, about 19.60, about 19.86, about 20.52, about 23.06, about 25.26, about 25.8, about 28.28, or about 29.37 degrees 2-theta.

In some embodiments, a crystalline form of Compound IV is characterized by at least eight peaks in its Powder X-ray diffraction pattern selected from those at about 17.96, about 19.04, about 19.60, about 19.86, about 20.52, about 23.06, about 25.26, about 25.8, about 28.28, or about 29.37 degrees 2-theta.

In some embodiments, a crystalline form of Compound IV is characterized by at least nine peaks in its Powder X-ray diffraction pattern selected from those at about 17.96, about 19.04, about 19.60, about 19.86, about 20.52, about 23.06, about 25.26, about 25.8, about 28.28, or about 29.37 degrees 2-theta.

In some embodiments, a crystalline form of Compound IV is characterized by the following ten peaks in its Powder X-ray diffraction pattern selected from those at about 17.96, about 19.04, about 19.60, about 19.86, about 20.52, about 23.06, about 25.26, about 25.8, about 28.28, or about 29.37 degrees 2-theta.

Compound V

In some embodiments, triazinium iodide forms include compounds and/or crystalline forms of compounds. Such compounds include. 1,1',1"-triethyl-4,4',4"-(1,3,5-triazin-2,4,6-triyl)tripyridinium trisiodide, 4-teptI, dihydrate, Compound V.

In some embodiments, 4-teptI, dihydrate, Compound V has offset almost-Piedfort units.

Figure 25:
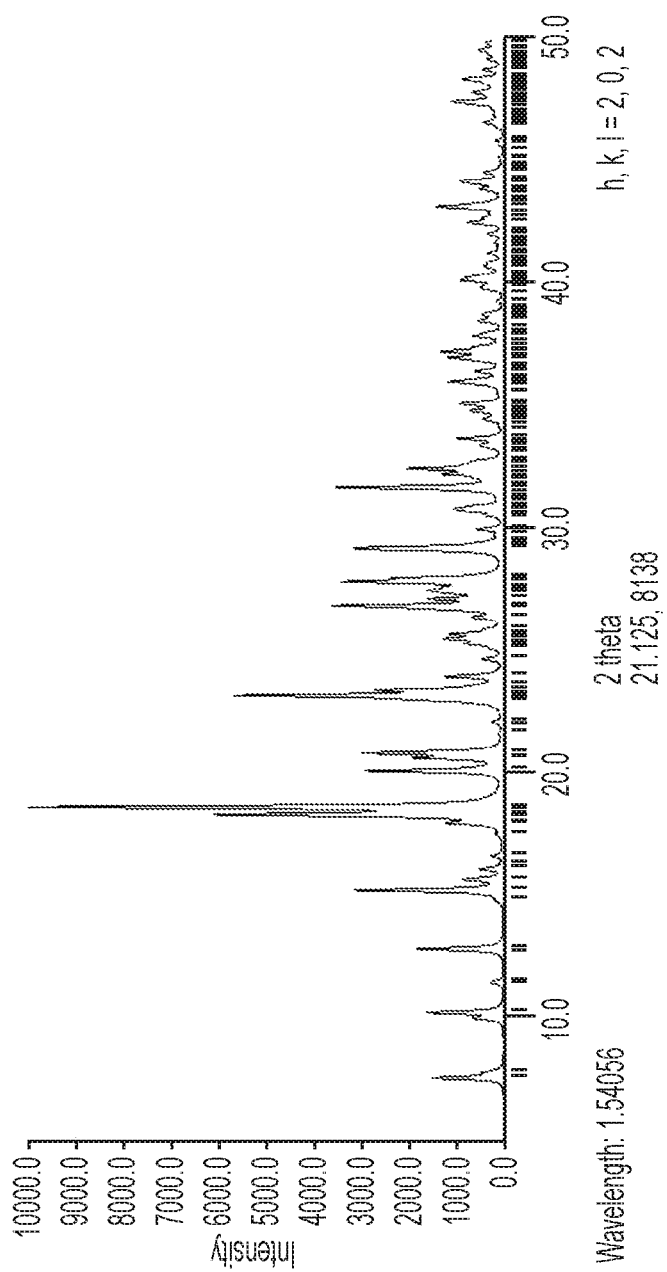
FIG. 25 shows a powder X-ray diffraction pattern of or substantially similar to that of 1,1',1"-triethyl-4,4',4"-(1,3,5-triazin-2,4,6-triyl)tripyridinium trisiodide, 4-teptI 2$H_2O$, Compound V.

In some embodiments, a crystalline form of 1,1',1"-triethyl-4,4',4"-(1,3,5-triazin-2,4,6-triyl)tripyridinium trisiodide, 4-teptI, .2H$_2$O, Compound V is characterized by a powder X-ray diffraction pattern substantially similar to that to depicted in FIG. 25.

In some embodiments, a crystalline form of Compound V is characterized by one or more peaks in its powder X-ray diffraction pattern selected from those at about 15.28, about 18.38, about 18.74, about 20.18, about 20.9, about 23.46, about 26.9, about 27.9, about 29.28, or about 31.74 degrees 2-theta.

In some embodiments, a crystalline form of Compound V is characterized by one or more peaks in its Powder X-ray diffraction pattern selected from those at about 15.28, about 18.38, about 18.74, about 20.18, about 20.9, about 23.46, about 26.9, about 27.9, about 29.28, or about 31.74 degrees 2-theta.

In some embodiments, a crystalline form of Compound V is characterized by at least two peaks in its Powder X-ray diffraction pattern selected from those at about 15.28, about 18.38, about 18.74, about 20.18, about 20.9, about 23.46, about 26.9, about 27.9, about 29.28, or about 31.74 degrees 2-theta.

In some embodiments, a crystalline form of Compound V is characterized by at least three peaks in its Powder X-ray diffraction pattern selected from those at about 15.28, about 18.38, about 18.74, about 20.18, about 20.9, about 23.46, about 26.9, about 27.9, about 29.28, or about 31.74 degrees 2-theta.

In some embodiments, a crystalline form of Compound V is characterized by at least four peaks in its Powder X-ray diffraction pattern selected from those at about 15.28, about 18.38, about 18.74, about 20.18, about 20.9, about 23.46, about 26.9, about 27.9, about 29.28, or about 31.74 degrees 2-theta.

In some embodiments, a crystalline form of Compound V is characterized by at least five peaks in its Powder X-ray diffraction pattern selected from those at about 15.28, about 18.38, about 18.74, about 20.18, about 20.9, about 23.46, about 26.9, about 27.9, about 29.28, or about 31.74 degrees 2-theta.

In some embodiments, a crystalline form of Compound V is characterized by at least six peaks in its Powder X-ray diffraction pattern from those at about 15.28, about 18.38, about 18.74, about 20.18, about 20.9, about 23.46, about 26.9, about 27.9, about 29.28, or about 31.74 degrees 2-theta.

In some embodiments, a crystalline form of Compound V is characterized by at least seven peaks in its Powder X-ray diffraction pattern selected from those at about 15.28, about 18.38, about 18.74, about 20.18, about 20.9, about 23.46, about 26.9, about 27.9, about 29.28, or about 31.74 degrees 2-theta.

In some embodiments, a crystalline form of Compound V is characterized by at least eight peaks in its Powder X-ray diffraction pattern selected from those at about 15.28, about 18.38, about 18.74, about 20.18, about 20.9, about 23.46, about 26.9, about 27.9, about 29.28, or about 31.74 degrees 2-theta.

In some embodiments, a crystalline form of Compound V is characterized by at least nine peaks in its Powder X-ray diffraction pattern selected from those at about 15.28, about 18.38, about 18.74, about 20.18, about 20.9, about 23.46, about 26.9, about 27.9, about 29.28, or about 31.74 degrees 2-theta.

In some embodiments, a crystalline form of Compound V is characterized by the following ten peaks in its Powder X-ray diffraction pattern selected from those at about 15.28, about 18.38, about 18.74, about 20.18, about 20.9, about 23.46, about 26.9, about 27.9, about 29.28, or about 31.74 degrees 2-theta.

In some embodiments, 4-teptI dihydrate is colored a shade of dark red to black.

Compound VI

In some embodiments, triazinium iodide forms include compounds and/or crystalline forms of compounds. Such compounds include. 1,1',1"-trimethyl-3,3',3"-(1,3,5-triazin-2,4,6-triyl)tripyridinium trisiodide, 3-tmptI, Compound VI. In some embodiments, 1,1',1"-trimethyl-3,3',3"-(1,3,5-triazin-2,4,6-triyl)tripyridinium trisiodide, 3-tmptI, Compound VI is a positional isomer. In some embodiments, 1,1',1"-trimethyl-3,3',3"-(1,3,5-triazin-2,4,6-triyl)tripyridinium trisiodide, 3-tmptI, Compound VI is colored a shade of dark red to bright orange.

Figure 26:
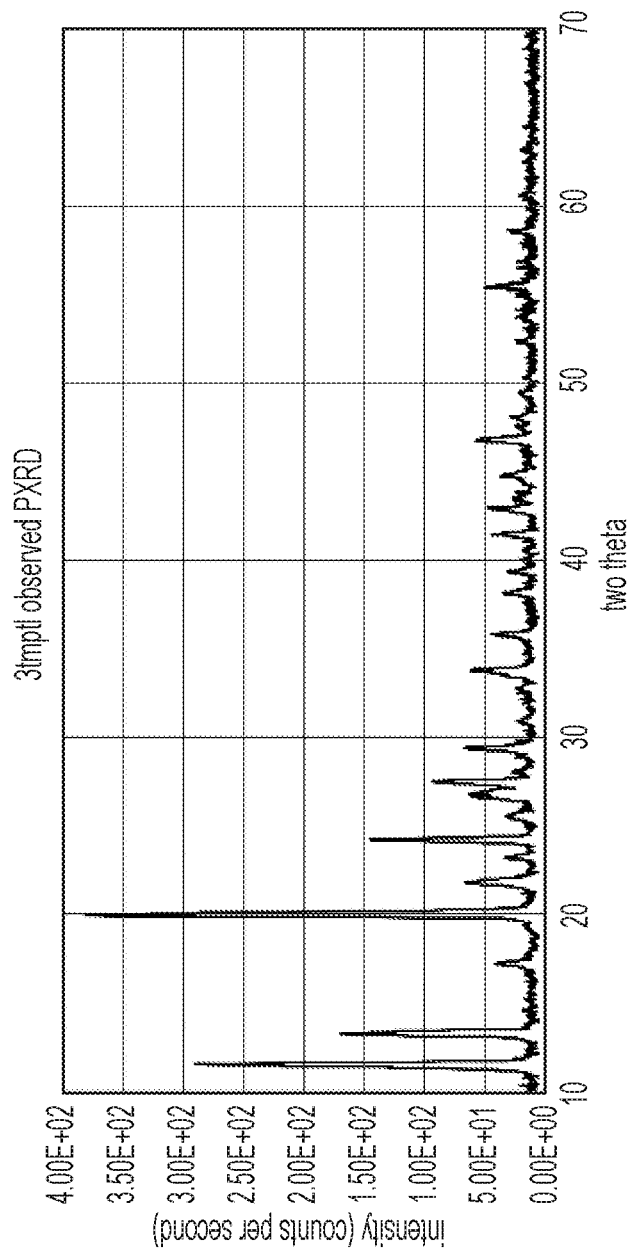
FIG. 26 shows a powder X-ray diffraction pattern of or substantially similar to that of 1,1',1"-trimethyl-3,3',3"-(1,3,5-triazin-2,4,6-triyl)tripyridinium trisiodide, 3-tmptI, Compound VI.

In some embodiments, a crystalline form of Compound VI is characterized by a powder X-ray diffraction pattern substantially similar to that to depicted in FIG. 26.

In some embodiments, a crystalline form of Compound VI is characterized by one or more peaks in its powder X-ray diffraction pattern selected from those at about 11.54, about 13.24, about 19.94, about 21.78, about 24.22, about 26.74, about 27.48, about 29.40, about 33.76, or about 46.72 degrees 2-theta.

In some embodiments, a crystalline form of Compound VI is characterized by one or more peaks in its Powder X-ray diffraction pattern selected from those at about 11.54, about 13.24, about 19.94, about 21.78, about 24.22, about 26.74, about 27.48, about 29.40, about 33.76, or about 46.72 degrees 2-theta.

In some embodiments, a crystalline form of Compound VI is characterized by at least two peaks in its Powder X-ray diffraction pattern selected from those at about 11.54, about 13.24, about 19.94, about 21.78, about 24.22, about 26.74, about 27.48, about 29.40, about 33.76, or about 46.72 degrees 2-theta.

In some embodiments, a crystalline form of Compound VI is characterized by at least three peaks in its Powder X-ray diffraction pattern selected from those at about 11.54, about 13.24, about 19.94, about 21.78, about 24.22, about 26.74, about 27.48, about 29.40, about 33.76, or about 46.72 degrees 2-theta.

In some embodiments, a crystalline form of Compound VI is characterized by at least four peaks in its Powder X-ray diffraction pattern selected from those at about 11.54, about 13.24, about 19.94, about 21.78, about 24.22, about 26.74, about 27.48, about 29.40, about 33.76, or about 46.72 degrees 2-theta.

In some embodiments, a crystalline form of Compound VI is characterized by at least five peaks in its Powder X-ray diffraction pattern selected from those at about 11.54, about 13.24, about 19.94, about 21.78, about 24.22, about 26.74, about 27.48, about 29.40, about 33.76, or about 46.72 degrees 2-theta.

In some embodiments, a crystalline form of Compound VI is characterized by at least six peaks in its Powder X-ray diffraction pattern selected from those at about 11.54, about 13.24, about 19.94, about 21.78, about 24.22, about 26.74, about 27.48, about 29.40, about 33.76, or about 46.72 degrees 2-theta.

In some embodiments, a crystalline form of Compound VI is characterized by at least seven peaks in its Powder X-ray diffraction pattern selected from those at about 11.54, about 13.24, about 19.94, about 21.78, about 24.22, about 26.74, about 27.48, about 29.40, about 33.76, or about 46.72 degrees 2-theta.

In some embodiments, a crystalline form of Compound VI is characterized by at least eight peaks in its Powder X-ray diffraction pattern selected from those at about 11.54, about 13.24, about 19.94, about 21.78, about 24.22, about 26.74, about 27.48, about 29.40, about 33.76, or about 46.72 degrees 2-theta.

In some embodiments, a crystalline form of Compound VI is characterized by at least nine peaks in its Powder X-ray diffraction pattern selected from those at about 11.54, about 13.24, about 19.94, about 21.78, about 24.22, about 26.74, about 27.48, about 29.40, about 33.76, or about 46.72 degrees 2-theta.

In some embodiments, a crystalline form of Compound VI is characterized by the following ten peaks in its Powder X-ray diffraction pattern selected from those at about 11.54, about 13.24, about 19.94, about 21.78, about 24.22, about 26.74, about 27.48, about 29.40, about 33.76, or about 46.72 degrees 2-theta.

Compound VII

In some embodiments, triazinium iodide forms include compounds and/or crystalline forms of compounds. Such compounds include. 1,1',1"-triethyl-2,2',2"-(1,3,5-triazin-2,4,6-triyl)tripyridinium trisiodide, 2-teptI, Compound VII.

In some embodiments, 1,1',1"-triethyl-2,2',2"-(1,3,5-triazin-2,4,6-triyl)tripyridinium trisiodide, 2-teptI, Compound VII is colored a shade of dark red to bright orange.

In some embodiments, compounds and/or crystalline forms of compounds include, for example, ethyl and isopropyl analogs; salts of related cations; and with varied anions ($Br^-$, $I_3^-$...).

In some embodiments, synthesis with a different derivatives of cyanopyridinium starting materials, for example 2-C-1-MP+ and 3-C-1-MP+ is performed.

In some embodiments, synthesis with a different derivatives of cyanopyridinium using other Lewis acid and alcohol solvent to optimize the conditions for the formation of triazine molecules.

In some embodiments, methods of forming related compounds include varying alkyl constituent and/or position on its ring.

In some embodiments, organic cations can be modified by varying types and ring positions of attached groups.

In some embodiments, methods of forming related compounds include varying its anion. In some embodiments, anionic substitutions can be made, for example salts of related cations with varied anions ($Br^-$, $I_3^-$...).

S-triazine (1,3,5, Triazine)

1,3,5-Triazine (a.k.a. s-triazine) and its derivatives have many applications in industrial, pharmaceuticals and supramolecular structures. Some of these applications include acting as herbicides and insecticides, being an integral core structure in chemotherapeutic agents—such as anticancer, anti-angiogenesis, and anti-HIV—and providing an important subunit in the formation of supramolecular structures. (See Naseer, M., "Synthons for supramolecular assemblies:

Synthesis of new triazine-core polyhydroxylated and multi-N-donor compounds" 4.2 Chem. Eur. J., 149-152 (2013)).

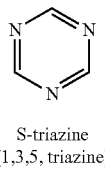

S-triazine
(1,3,5, triazine)

Previously reported syntheses of s-triazine often require extreme or vigorous conditions, such as extreme pressure (5000-8000×10$^5$ Pa), high temperatures, treatment with high concentrations of strong acids or bases, and/or long reaction times. (See Cairns, T. L, "The trimerization of nitriles at high pressures", 74 J. Am. Chem. Soc., 5633-5636 (1952); see also Therrien et al., 696 J Organomet Chem, 637-651 (2011); see also Diaz-Ortiz, et al., 4 Green Chem, 339-343 (2002); see also Janczak, 659 J Molec Struct, 71-79 (2003)).

Figure 14:
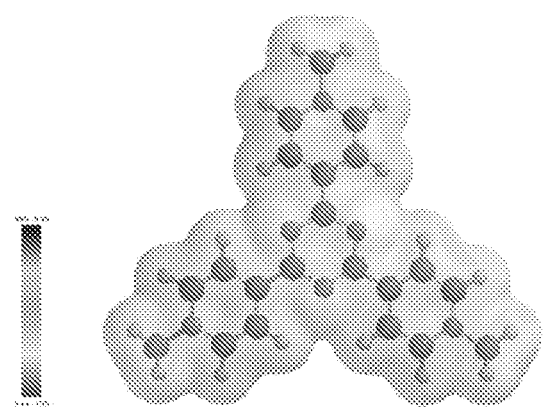
FIG. 14 shows an electrostatic potential map representation for the trivalent s-triazine cation, Compound II.
Figure 14:
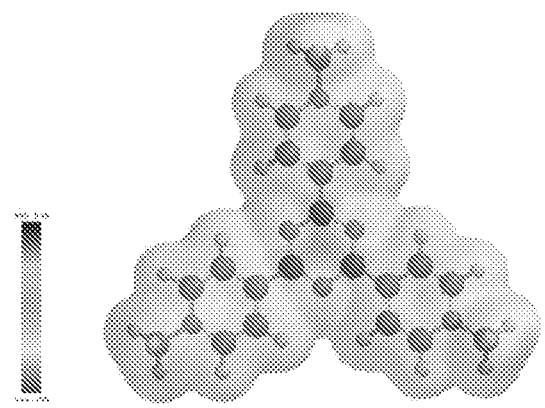

Trivalent 1,1',1"-trimethyl-4,4',4"-(1,3,5-triazin-2,4,6-triyl)tripyridinium Cation FIG. 14 shows an electrostatic potential map representation for trivalent 1,1',1"-trimethyl-4,4',4"-(1,3,5-triazin-2,4,6-triyl)tripyridinium cation.

The electrostatic potential map of FIG. 14 at panel (a) and FIG. 14 at panel (b) shows that 1,1',1"-trimethyl-4,4',4"-(1,3,5-triazin-2,4,6-triyl)tripyridinium cation's structure has a shape that is somewhat similar to that of a bowl. FIG. 14 at panel (a) shows a viewpoint looking up at a 1,1',1"-trimethyl-4,4',4"-(1,3,5-triazin-2,4,6-triyl)tripyridinium cation's structure from a bottom of its bowl. FIG. 14 at panel (b) shows a viewpoint looking down into a 1,1',1"-trimethyl-4,4',4"-(1,3,5-triazin-2,4,6-triyl)tripyridinium cation's structure from a top view of its bowl, that is, looking inside. The scale for FIG. 14 goes from +891 kJ/mol (blue) to +644 kJ/mol (red) in spectral order.

FIG. 14 at panels (a) and (b) show red regions that represent areas of least positive potential. FIG. 14 at panels (a) and (b) show blue regions that represent areas of most positive potential. Red areas are still positively charged as this 1,1',1"-trimethyl-4,4',4"-(1,3,5-triazin-2,4,6-triyl)tripyridinium cation molecule is overall a 3+ cation.

Trivalent 1,3,5-triazinium Cation Based Compounds—Trisbromides

Figure 27:
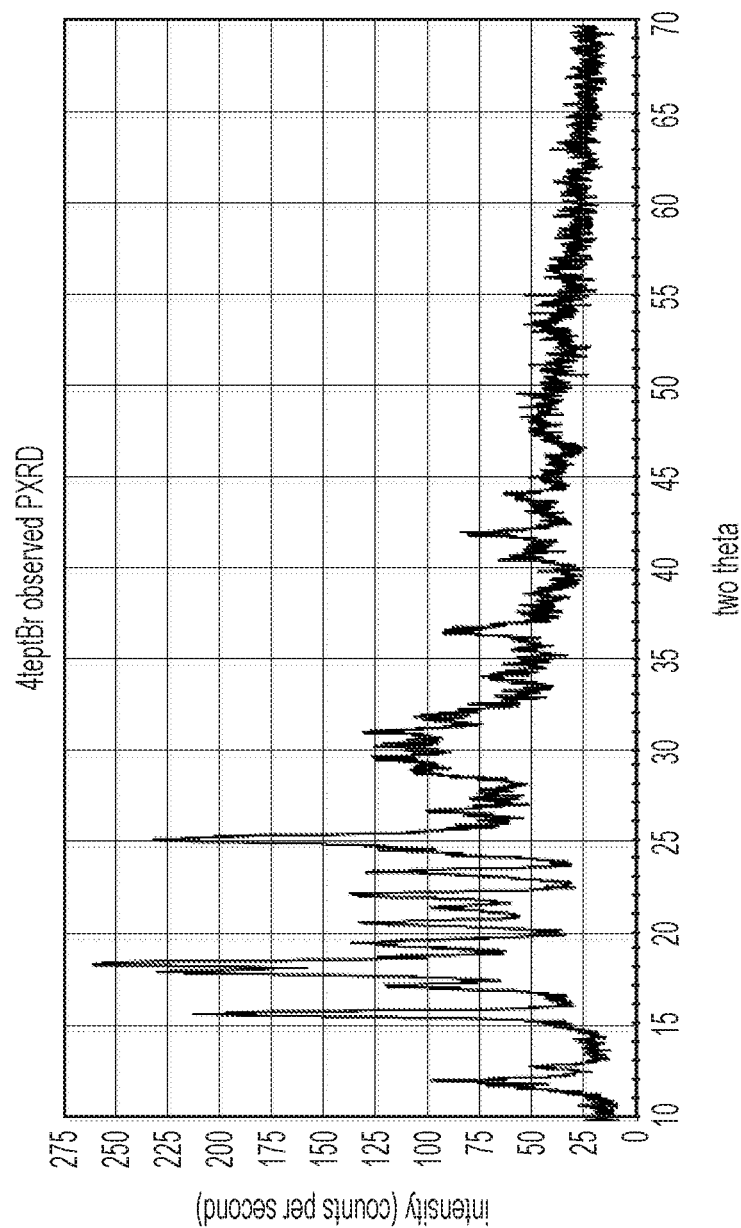
FIG. 27 shows a powder X-ray diffraction pattern of or substantially similar to that of 1,1',1"-triethyl-4,4',4"-(1,3,5-triazin-2,4,6-triyl)tripyridinium trisbromide, 4teptBr, Compound VIII.
Figure 28:
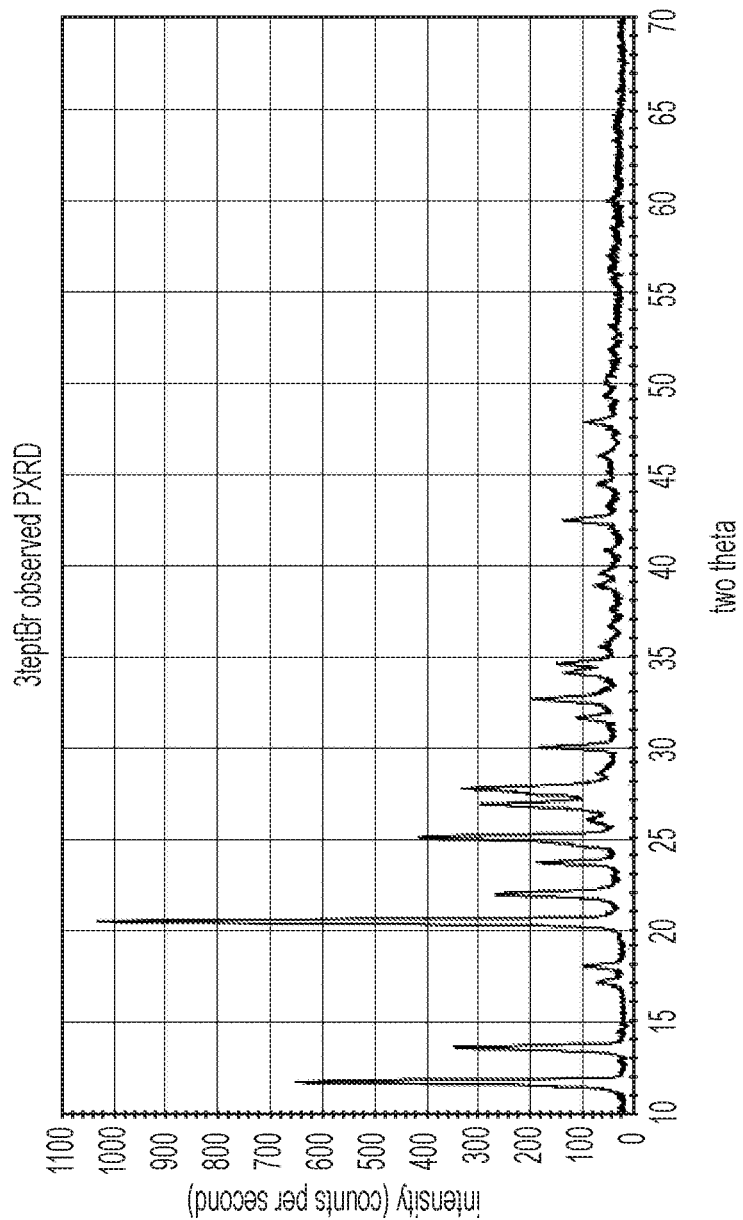
FIG. 28 shows a powder X-ray diffraction pattern of or substantially similar to that of 1,1',1"-triethyl-3,3',3"-(1,3,5-triazin-2,4,6-triyl)tripyridinium trisbromide, 3teptBr, Compound IX.

In some embodiments, other compounds and crystalline forms of compounds containing trivalent 1,3,5-triazinium cations are disclosed.
Compound VIII
In some embodiments, a crystalline form of 1,1',1"-triethyl-4,4',4"-(1,3,5-triazin-2,4,6-triyl)tripyridinium trisbromide, Compound VIII is characterized by a powder X-ray diffraction pattern substantially similar to that to depicted in FIG. 27.
Compound IX
In some embodiments, a crystalline form of 1,1',1"-triethyl-3,3',3"-(1,3,5-triazin-2,4,6-triyl)tripyridinium trisbromide, Compound IX is characterized by a powder X-ray diffraction pattern substantially similar to that to depicted in FIG. 28.
In some embodiments, a crystalline form of 1,1',1"-triethyl-3,3',3"-(1,3,5-triazin-2,4,6-triyl)tripyridinium trisbromide, Compound IX is characterized by one or more peaks in its powder X-ray diffraction pattern selected from those at about 11.78, about 13.56, about 20.56, about 22.06, about 23.76, about 25.12, about 26.94, about 27.80, about 30.08, or about 32.72 degrees 2-theta.

In some embodiments, a crystalline form of 1,1',1"-triethyl-3,3',3"-(1,3,5-triazin-2,4,6-triyl)tripyridinium trisbromide, Compound IX is characterized by one or more peaks in its Powder X-ray diffraction pattern selected from those at about 11.78, about 13.56, about 20.56, about 22.06, about 23.76, about 25.12, about 26.94, about 27.80, about 30.08, or about 32.72 degrees 2-theta.

In some embodiments, a crystalline form of 1,1',1"-triethyl-3,3',3"-(1,3,5-triazin-2,4,6-triyl)tripyridinium trisbromide, Compound IX is characterized by at least two peaks in its Powder X-ray diffraction pattern selected from those at about 11.78, about 13.56, about 20.56, about 22.06, about 23.76, about 25.12, about 26.94, about 27.80, about 30.08, or about 32.72 degrees 2-theta.

In some embodiments, a crystalline form of 1,1',1"-triethyl-3,3',3"-(1,3,5-triazin-2,4,6-triyl)tripyridinium trisbromide, Compound IX is characterized by at least three peaks in its Powder X-ray diffraction pattern selected from those at about 11.78, about 13.56, about 20.56, about 22.06, about 23.76, about 25.12, about 26.94, about 27.80, about 30.08, or about 32.72 degrees 2-theta.

In some embodiments, a crystalline form of 1,1',1"-triethyl-3,3',3"-(1,3,5-triazin-2,4,6-triyl)tripyridinium trisbromide, Compound IX is characterized by at least four peaks in its Powder X-ray diffraction pattern selected from those at about 11.78, about 13.56, about 20.56, about 22.06, about 23.76, about 25.12, about 26.94, about 27.80, about 30.08, or about 32.72 degrees 2-theta.

In some embodiments, a crystalline form of 1,1',1"-triethyl-3,3',3"-(1,3,5-triazin-2,4,6-triyl)tripyridinium trisbromide, Compound IX is characterized by at least five peaks in its Powder X-ray diffraction pattern selected from those at about 11.78, about 13.56, about 20.56, about 22.06, about 23.76, about 25.12, about 26.94, about 27.80, about 30.08, or about 32.72 degrees 2-theta.

In some embodiments, a crystalline form of 1,1',1"-triethyl-3,3',3"-(1,3,5-triazin-2,4,6-triyl)tripyridinium trisbromide, Compound IX is characterized by at least six peaks in its Powder X-ray diffraction pattern selected from those at about 11.78, about 13.56, about 20.56, about 22.06, about 23.76, about 25.12, about 26.94, about 27.80, about 30.08, or about 32.72 degrees 2-theta.

In some embodiments, a crystalline form of 1,1',1"-triethyl-3,3',3"-(1,3,5-triazin-2,4,6-triyl)tripyridinium trisbromide, Compound IX is characterized by at least seven peaks in its Powder X-ray diffraction pattern selected from those at about 11.78, about 13.56, about 20.56, about 22.06, about 23.76, about 25.12, about 26.94, about 27.80, about 30.08, or about 32.72 degrees 2-theta.

In some embodiments, a crystalline form of 1,1',1"-triethyl-3,3',3"-(1,3,5-triazin-2,4,6-triyl)tripyridinium trisbromide, Compound IX is characterized by at least eight peaks in its Powder X-ray diffraction pattern selected from those at about 11.78, about 13.56, about 20.56, about 22.06, about 23.76, about 25.12, about 26.94, about 27.80, about 30.08, or about 32.72 degrees 2-theta.

In some embodiments, a crystalline form of 1,1',1"-triethyl-3,3',3"-(1,3,5-triazin-2,4,6-triyl)tripyridinium trisbromide, Compound IX is characterized by at least nine peaks in its Powder X-ray diffraction pattern selected from those at about 11.78, about 13.56, about 20.56, about 22.06, about 23.76, about 25.12, about 26.94, about 27.80, about 30.08, or about 32.72 degrees 2-theta.

In some embodiments, a crystalline form of 1,1',1"-triethyl-3,3',3"-(1,3,5-triazin-2,4,6-triyl)tripyridinium tris-bromide, Compound IX is characterized by the following ten peaks in its Powder X-ray diffraction pattern selected from those at about 11.78, about 13.56, about 20.56, about 22.06, about 23.76, about 25.12, about 26.94, about 27.80, about 30.08, or about 32.72 degrees 2-theta.

Properties of Compounds and Crystalline Forms Thereof

In some embodiments, compounds and/or crystalline forms of compounds disclosed herein, possess unique electrical, optical, optoelectronic, and/or semiconductor properties. In some embodiments, organic salts such as those disclosed herein are generally lighter in weight, less toxic and less expensive than conventional materials that perform same or similar functions.

In some embodiments, compounds and/or crystalline forms disclosed herein are solution processable.

In some embodiments, compounds and/or crystalline forms disclosed herein have properties between molecules and bulk solid semiconductors. It is generally well known that the nanoscale systems show interesting physical properties such as increasing semiconductor band gap due to electron confinement. In some embodiments, compounds and/or crystalline forms disclosed herein behave as organic conductors or semiconductor materials.

In some embodiments, compounds and/or crystalline forms of organic salts disclosed herein possess measurable properties, for example, including band gap, charge mobility, conductivity, dielectric constant, HOMO-LUMO gap, magnetic characteristics, octapole moments, and/or resistivity. In some embodiments, such compound, forms, and/or salts are characterized by measurable properties.

In some embodiments, compounds and crystalline forms of compounds disclosed herein exhibit band gap in a range of about 0.1-6 eV.

In some embodiments, compounds and crystalline forms of compounds disclosed herein exhibit band gap in a range of about 0.1 eV, about 0.2 eV, about 0.3 eV, about 0.4 eV, about 0.5 eV, about 0.6 eV, about 0.7 eV, about 0.8 eV, about 0.9 eV, about 1.0 eV, about 1.1 eV, about 1.2 eV, about 1.3 eV, about 1.4 eV, about 1.5 eV, about 1.6 eV, about 1.7 eV, about 1.8 eV, about 1.9 eV, about 2.0 eV, about 2.1 eV, about 2.2 eV, about 2.3 eV, about 2.4 eV, about 2.5 eV, about 2.6 eV, about 2.7 eV, about 2.8 eV, about 2.9 eV, about 3.0 eV, about 3.1 eV, about 3.2 eV, about 3.3 eV, about 3.4 eV, about 3.5 eV, about 3.6 eV, about 3.7 eV, about 3.8 eV, about 3.9 eV, about 4.0 eV, about 4.1 eV, about 4.2 eV, about 4.3 eV, about 4.4 eV, about 4.5 eV, about 4.6 eV, about 4.7 eV, about 4.8 eV, about 4.9 eV, about 5.0 eV, about 5.1 eV, about 5.2 eV, about 5.3 eV, about 5.4 eV, about 5.5 eV, about 5.6 eV, about 5.7 eV, about 5.8 eV, about 5.9 eV, about 6.0 eV, or higher.

In some embodiments, compounds and crystalline forms of compounds disclosed herein exhibit band gap in a range of about 0.1-6 eV at 0 K.

In some embodiments, compounds and crystalline forms of compounds disclosed herein exhibit band gap in a range of about 0.1-6 eV at 300 K.

In some embodiments, band gap is measured via four-point probe and transport property measurements. In some embodiments, band gap is calculated based on diffuse reflectance spectrum measurements.

In some embodiments, compounds and crystalline forms of compounds disclosed herein have possible anisotropy in magnetic behavior. In some embodiments, such behavior indicates that compounds and crystalline forms of compounds disclosed herein exhibit diamagnetic properties.

In some embodiments, band gap is calculated based on a crystal diffuse reflectance or absorption spectrum. (See Ghobadi, :Band Gap Determination using Absorption Spectrum Fitting Procedure," 3 International Nano Letters 2 (2013)), explains using absorption spectrum fitting method was applied to estimate the optical band gap and width of the band tail. Ghobadi details a method for determining band gap from spectrum for films and particles by plotting (absorbance/wavelength)^2 on y vs. inverse wavelength on x. The linear portion of this plot gives a straight-line fit where the x-intercept is reciprocal wavelength of the band gap. That turns out to be 667 nm (=1.86 eV). Thus the value of band gap, in electron volt, can be calculated extrapolating the linear of the $(Abs(\lambda)/\lambda)^{1/m}$ v. $1/\lambda$, curve at $(Abs/\lambda)^{1/m}=0$. By using the least squares technique and extrapolating the straight-line portion of the plot gives the corresponding E(eV) value.

In some embodiments, using Ghobadi's method, compounds and crystalline forms of compounds disclosed herein have a calculate band gap of about 1.86 eV. In some embodiments, extrapolating to a baseline of a diffuse reflectance or absorbance spectrum results in an estimated band gap of about 1.8 eV.

In some embodiments, calculated and estimated band gap measurements correspond to an optically determined band gap of 1.86 eV, which is comparatively between that of GaAs=1.43 eV and GaP=2.26 eV).

In some embodiments, band gap from electrical transport data for compounds and crystalline form of compounds disclosed here is estimated to be about 0.55 eV. In some embodiments, resistance vs. temperature fit of band gap from electrical transport data is comparatively between that of InAs=0.36 eV and InN=0.7 eV. It is common for optical band gap measurements to be larger than those found from fits to □ vs. T. A single crystal of the compound exhibits electrical resistivity of about $6\times10^2$ $\rho(\Omega m)$ at room temperature, such values are very close to that of silicon.

In some embodiments, compounds and crystalline forms disclosed herein possess special non-linear optical properties. In some embodiments, compounds and crystalline forms are characterized by Piedfort units. In some embodiments, compounds and crystalline forms disclosed herein have a given non-zero octupolar moment. (See for example "Crystal Structures and Packing of 2,4,6-tris(4-Fluorophenoxy)-1,3,5-triazine and 2,4,6-tris(3,4-Dimethylphenoxy)-1,3,5-triazine. New Materials for Octupolar Nonlinear Optics," Roland Boese, Gautam R. Desiraju, Ram K. R. Jetti, Michael T. Kirchner, Isabelle Ledoux, Venkat R. Thalladi, and Joseph Zyss, *Structural Chemistry*, 13, 321-328 (2002)).

In some embodiments, compounds and crystalline forms disclosed herein possess cation pairs with 6 I—. In some embodiments, such structures make Piedfort units that have non-zero octupolar moments, which lead to non-linear optical properties.

In some embodiments, compounds and crystalline forms of compounds disclosed herein exhibit dielectric constant of at least 5.

In some embodiments, compounds and crystalline forms of compounds disclosed herein exhibit a resistivity in a range of about $10^{-4}$ $\Omega m$ to $10^8$ $\Omega m$.

In some embodiments, compounds and crystalline forms of compounds disclosed herein exhibit a resistivity ($\rho$) in a range of about $10^{-4}$ $\Omega m$, about $10^{-3}$ $\Omega m$, about $10^{-2}$ $\Omega m$, about $10^{-1}$ Ωm, about $10^1$ Ωm, about $10^2$ Ωm, about $10^3$ Ωm, about $10^4$ Ωm, about $10^5$ Ωm, about $10^6$ Ωm, about $10^7$ Ωm, or about $10^8$ Ωm.

In some embodiments, compounds and crystalline forms of compounds disclosed herein exhibit a conductivity (a) in a range of about $10^4$ S/cm, about $10^3$ S/cm, about $10^2$ S/cm, about $10^1$ S/cm, about $10^{-1}$ S/cm, about $10^{-2}$ S/cm, about $10^{-3}$ S/cm, about $10^{-4}$ S/cm, about $10^{-5}$ S/cm, about $10^{-6}$ S/cm, about $10^{-7}$ S/cm, or about $10^{-8}$ S/cm.

In some embodiments, compounds and crystalline forms of compounds disclosed herein exhibit conductivity (σ) in a range of about $10^4$ S/cm, about $10^3$ S/cm, about $10^2$ S/cm, about $10^1$ S/cm, about $10^{-1}$ S/cm, about $10^{-2}$ S/cm, about $10^{-3}$ S/cm, about $10^{-4}$ S/cm, about $10^{-5}$ S/cm, about $10^{-6}$ S/cm, about $10^{-7}$ S/cm, or about $10^{-8}$ S/cm.

In some embodiments, compounds and crystalline forms of compounds disclosed herein exhibit an electron mobility in a range of about 50-50,000 $\mu_e$ cm$^2$/Vs.

In some embodiments, compounds and crystalline forms of compounds disclosed herein exhibit a hole mobility in a range of about 1-5,000 $\mu_e$ cm$^2$/Vs.

In some embodiments, compounds and crystalline forms of compounds disclosed herein exhibit an emission wavelength of about 200 nm to about 3000 nm.

Applications, Devices and Methods of Making and Using the Same

Materials that conduct electricity (metals, alloys, semiconductors, superconductors) or produce non-linear optical effects (e.g. second harmonic generation) are useful in electronic and photonic devices. These are highly prized materials that make devices such as doubling crystals, field effect transistors, lasers, LEDs, liquid crystal devices, liquid crystal displays, OFETs, OLEDs (organic light-emitting diodes) for vividly colorful displays, piezoelectrics, photonic modulators, photovoltaic cells, photovoltaics, sensors, semiconductor devices, specialized solar panels, thermoelectrics, and many others.

Most current optoelectronic materials are made of metals and metalloids such as gallium, aluminum, indium and arsenic. Their properties are tuned by varying the proportions of the elements present. In some cases these elements are expensive or toxic and all are heavier than carbon, nitrogen and hydrogen on a per atom basis.

The range of known, available materials with desired properties is incomplete but growing rapidly. The search for new organic conductors is an active area of scientific inquiry and technological development. These materials are expected to be less expensive to make, less toxic, and lighter weight than current materials. Triazine-based salts are not known for this purpose.

Developing optoelectronic devices that use organic materials is highly desirable because starting materials are inexpensive and less toxic. They are usually lighter in weight as well which can be important in some applications (e.g. automobiles and spacecraft).

In some embodiments, compounds and/or crystalline forms of compounds disclosed herein, contain motifs known as Piedfort units (composed of two cations and six anions in this case) that automatically have a non-zero octupolar moment. In some embodiments, Piedfort units imbue a material with optical properties including an ability to turn two smaller photons into one bigger one, second harmonic generation. In some embodiments, for example, second harmonic generation, or doubling, is useful to make higher energy laser beams from lower energy ones.

In some embodiments, compounds and/or crystalline forms of compounds disclosed herein form or are used to form devices, materials, liquid crystal devices and displays, nanoparticles, nanotubes, nanowires, sheets, blocks, films, scaffolds, or matrices.

In some embodiments, as discussed, compounds and/or crystalline forms of compounds disclosed herein exhibit trends in color and melting point with systematic changes, for example, modification to pyridine nitrogen position from 4- to 3- to 2- or substitution of progressively larger alkyl groups from methyl to ethyl to isopropyl. In some embodiments, such trends suggest that optoelectronic properties are readily tunable by engineering positively charged organic cations.

In some embodiments, compounds and/or crystalline forms of compounds disclosed herein and that possess a range of desirable electrical, optical, optoelectronic, and/or semiconductor properties can vary by composition and crystallinity. In some embodiments, crystal growth conditions and methods can be varied. In some embodiments, compounds and/or crystalline forms of compounds disclosed herein possess properties that can be tuned by changing or mixing different proportions of these pure compounds to make solid solutions or heterogeneous mixtures.

In some embodiments, compounds and/or crystalline forms of compounds disclosed herein and that possess desirable electrical, optical, optoelectronic, and/or semiconductor properties are useful in products or devices or useful in manufacturing such products or devices such as doubling crystals, field effect transistors, lasers, liquid crystal devices, liquid crystal displays, LEDs, OFETs, OLEDs (organic light-emitting diodes) for vividly colorful displays, piezoelectrics, photonic modulators, photovoltaic cells, photovoltaics, sensors, semiconductor devices, specialized solar panels, thermoelectrics, and many others.

EXEMPLIFICATION

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

The present example describes preparation of 1,1',1''-trimethyl-4,4',4''-(1,3,5-triazin-2,4,6-triyl)tripyridinium trisiodide, Compound II by Cyclotrimerization of 4-cyano-1-methylpyridinium iodide.

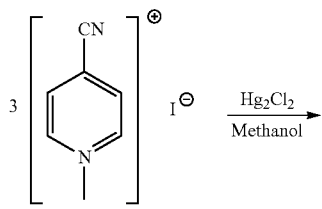

-continued

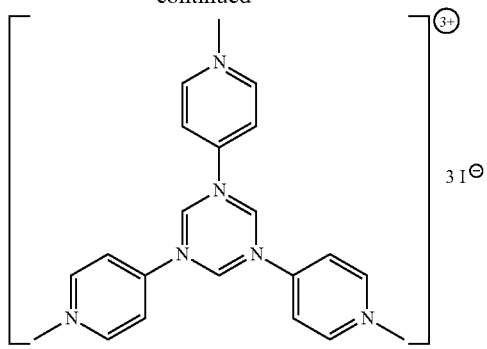

In some embodiments, synthesis of s-triazine via cyclotrimerization of nitriles is possible under mild conditions including Lewis acid catalyst and alcohol solvent.

4-cyano-1-methylpyridinium iodide (0.259 g, 1.05 mmol) was dissolved in 10 mL of pure methanol. The solution changed from yellow to dark brown color over a few minutes. Mercurous chloride $Hg_2Cl_2$ (0.290 g, 0.614 mmol) was added into solution mixture, stirred for 15 minutes to produce a maroon solution with dark olive green precipitate. Maroon solution was isolated via vacuum filtration and 0.2-micron syringe filtration. Crystals were obtained by slow evaporation for 69.32% yield.

Example 2

The present example describes analysis of Compound II.

Figure 15:
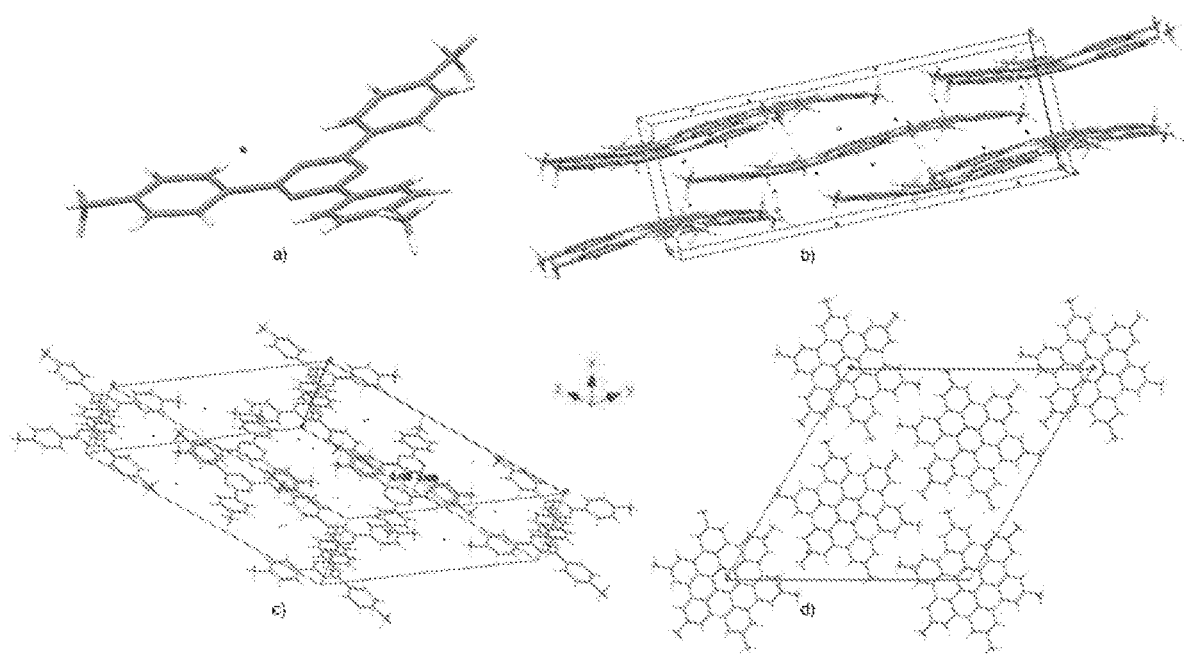
FIG. 15 shows crystal packing of 1,1',1"-trimethyl-4,4',4"-(1,3,5-triazin-2,4,6-triyl)tripyridinium trisiodide, Compound II.

X-ray crystallography was used to obtain the structural proof of formation of 1,1',1"-trimethyl-4,4',4"-(1,3,5-triazin-2,4,6-triyl)tripyridinium trisiodide. FIG. 15 shows that the crystal packing is a rhombohedral lattice. As shown in FIG. 15, at panel (a), 1,1',1"-trimethyl-4,4',4"-(1,3,5-triazin-2,4,6-triyl)tripyridinium trisiodide's cation core is bent at its central aromatic ring. Parallel overlap is observed. Such overlap is illustrated by π-π stacking between bent 1,1',1"-trimethyl-4,4',4"-(1,3,5-triazin-2,4,6-triyl)tripyridinium trisiodide molecules with an alternating rotation by 180°. FIG. 15 at panel (d) shows such a π-π stacking effect. A distance of 3.436 Å was calculated for this π-π interaction. (See FIG. 15 at panel (c)).

UV-Vis spectroscopy was used to investigate the effects of the ratio of $Hg_2Cl_2$ catalyst to 4-cyano-1-methylpyridinium iodide on the cyclotrimerization process. Gradual changes in absorption over time primarily occurred within the 450-650 nm wavelength.

Figure 16:
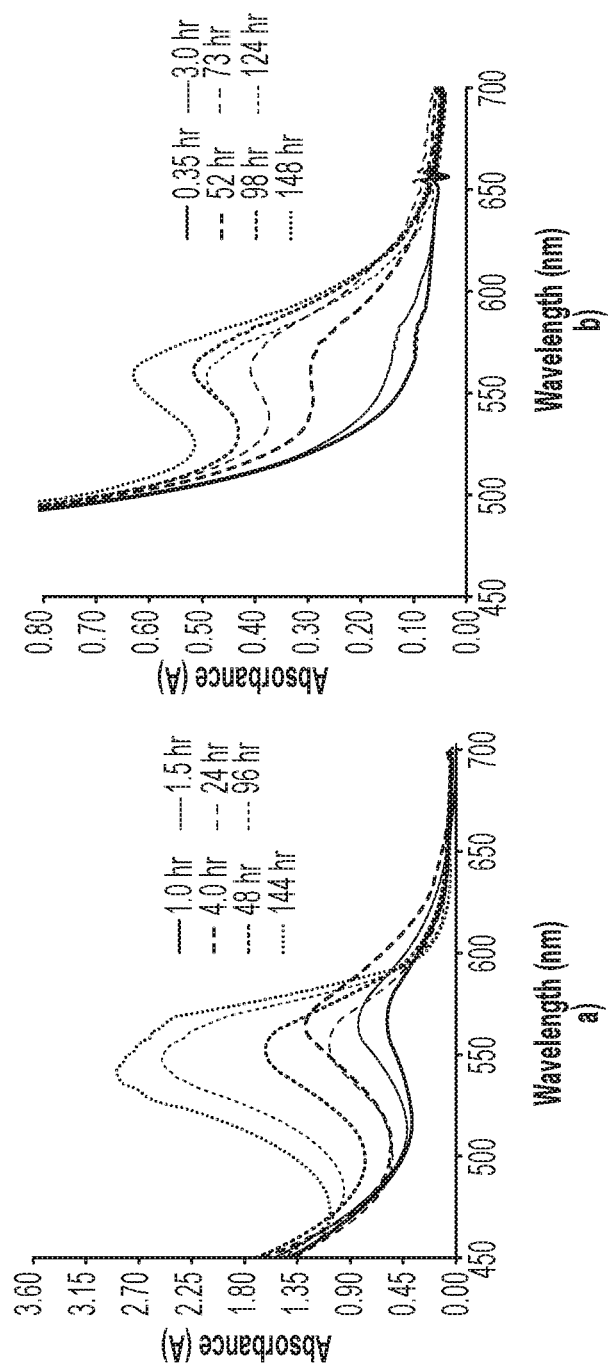
FIG. 16 shows UV-Vis absorption spectra over time of reaction mixture.

FIG. 16 at panel (a) shows absorption spectra over time of reaction mixture using equimolar amount of Lewis acid $Hg_2Cl_2$. FIG. 16 at panel (b) shows absorption spectra over time of reaction mixture using catalytic amount of Lewis acid $Hg_2Cl_2$.

FIG. 16 shows significant difference in absorbance values. Differences in absorbance data in FIG. 16 (a) and FIG. 16 (b) indicates that a cyclotrimerization reaction catalyzed using an equimolar amount of $Hg_2Cl_2$ takes place much faster compared to one using a catalytic amount of $Hg_2Cl_2$.

UV-Vis results along with NMR spectroscopic data (not shown) demonstrate that cyclotrimerization of 4-C-1-MPI could occur via a step-wise reaction.

Example 3

The present example describes a stepwise Cyclotrimerization of 4-cyano-1-methylpyridinium iodide.

Proposed Step-wise Mechanism for the Cyclotrimerization of 4-cyano-1-methylpyridinium Iodide Catalyzed by $Hg_2Cl_2$. in Methanol

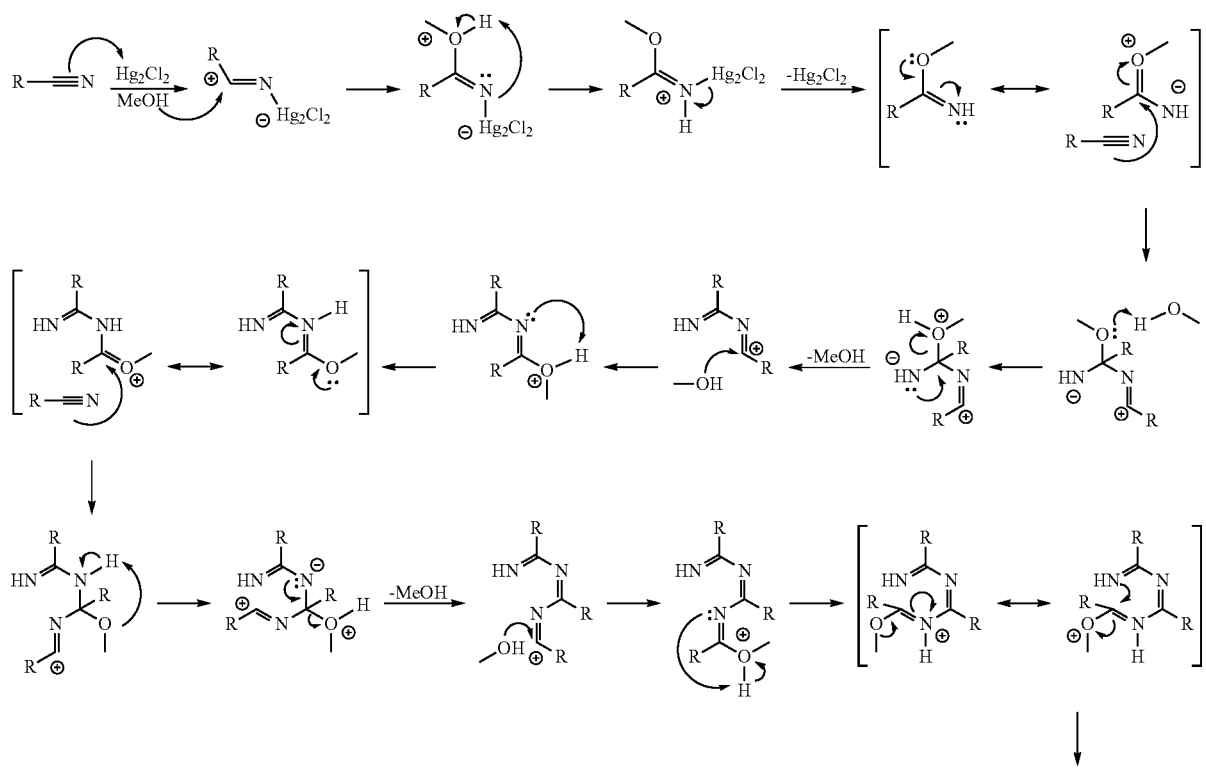

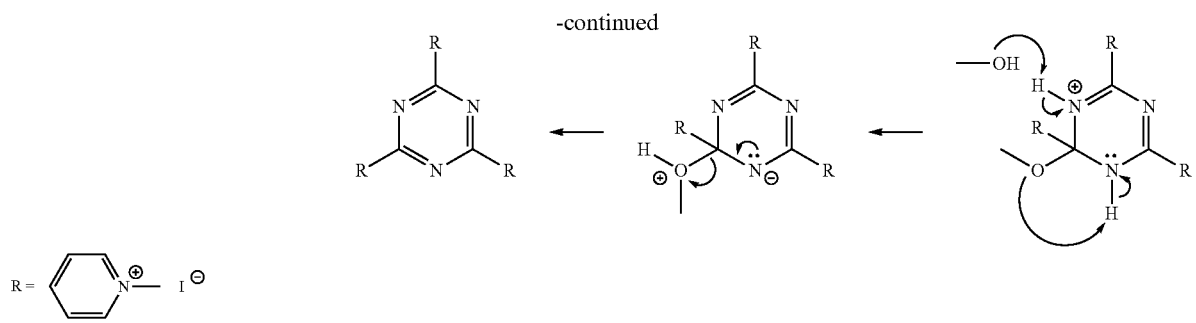

Example 4

The present example describes synthesis of 4-cyano-1-methylpyridinium triiodide, Compound I.

All solvents and reagents were purchased from commercial suppliers and used without modifications. NMR spectrum was obtained with a Varian 400 MHz NMR. Melting points were obtained using a Shimadzu DSC-60 plus differential scanning calorimeter. Crystal structures were determined using a Bruker Smart APEX CCD single crystal X-ray diffractometer.

0.5 g (2.0 mmol) of previously synthesized 4-cyano-1-methylpyridinium iodide (see Kammer, et al., E68 Acta Cryst, 2514 (2012)) was dissolved in 20 mL of deionized water and acidified with three drops of 37% HCl(aq) to avoid hydrolysis of the nitrile group. A 2.2 mmol Cl— equivalent of AgCl, $Hg_2Cl_2$ or $PbCl_2$ was added and the mixture was gently heated and stirred for 20 minutes. The cooled mixture was vacuum filtered and the precipitate discarded. The supernatant was filtered again via syringe and a 0.2 micron disc then covered loosely with Parafilm and left in the fume hood. Three weeks later black flakes were collected by vacuum filtration, air dried and analyzed by single crystal X-ray diffraction. Yield 9%, n.m.pt. 118° C.

Example 5

The present example describes an original synthesis 1,1',1"-trimethyl-4,4',4"-(1,3,5-triazin-2,4,6-triyl)tripyridinium trisiodide, Compound II (mixed product).

0.26 g (1.1 mmol) of previously synthesized 4-cyano-1-methylpyridinium iodide (see Kammer, et al., E68 Acta Cryst, 2514 (2012)) was readily dissolved in 10 mL of methanol. The yellow solution turned brownish over time.

0.29 g of $Hg_2Cl_2$ (1.2 mmol Cl—) was added and the mixture was stirred for 10 minutes, becoming almost black. The mixture was vacuum filtered and the olive precipitate was washed with a few mL of methanol and then discarded. The clear pomegranate-colored supernatant was left to evaporate in the fume hood. The same steps were carried out with 0.25 g 4-cyano-1-methylpyridinium iodide and 0.17 g $PbCl_2$ (1.2 mmol Cl—) producing a dark brown mixture that separated into a yellowish precipitate and an amber colored supernatant. AgCl was not used in this reaction. The solid product from evaporation of both supernatants appeared brick red and was found by optical microscopy to consist of clumps of red needles grown on top of clear plates. The crystal structure of the clear plates showed them to be 4-carbamido-1-methylpyridinium iodide while the red needles were found to be 1,1',1"-trimethyl-4,4',4"-(1,3,5-triazin-2,4,6-triyl)tripyridinium trisiodide, Compound II.

Example 6

The present example describes an alternative synthesis of 1,1',1"-trimethyl-4,4',4"-(1,3,5-triazin-2,4,6-triyl)tripyridinium trisiodide, Compound II.

Commercially available 2,4,6-tris-(4-pyridyl)-1,3,5-triazine (0.75 g, 2.4 mmol) was mixed with 20 mL of dimethylformamide (DMF) and briefly stirred until opaque. Methyl iodide (0.60 mL, 9.6 mmol) was added via glass syringe. The mixture turned red after 10 minutes of heating at 90° C. and was then allowed to stir for 48 h at 90° C. with a reflux condenser. The resulting red solid was collected via vacuum filtration and washed with 6 mL of diethyl ether. The dried solid was recrystallized from hot water. After slow cooling, vacuum filtration, cold water wash and air drying, 1.7 g of dark, shiny needles was obtained. This product showed two melting point peaks at 343° C. and 383° C. To purify, 1.4 g was dissolved in 20 mL of hot water and then cooled slowly. After about 1 hour, this orange solution produced long dark needles with a yellow supernatant. Vacuum filtration, cold water wash and air drying gave long shiny dark red needles (1.14 g, 81% recovery, 65% overall yield, n.m.pt. 383° C.). Slow evaporation of the combined filtrate and wash eventually grew additional needles several cm long. The NMR of the recrystallized product coincides with that reported by (see Gries et al., Ann Chem 1021-1028 (1991)) for the hexafluorophosphate salt of the same triazinium cation. 1H-NMR (400 MHz, [D6] DMSO) δ=9.48 (d, 6H, 2-H, 2'-H, 2"-H, 6-H, 6'-H, 6"-H), 9.36 (d, 6H, 3-H, 3'-H, 3"-H, 5-H, 5'-H, 5"-H), 4.50 (s, 9H, 1-H, 13'-H, 13"-H).

Alternatively, commercially available 2,4,6-Tri(3-pyridal)-1,3,5-triazine (0.75 g, 2.4 mmol) was mixed with 60 mL of DMF and heated at 90° C. until mostly dissolved. Then, methyl iodide (3 mL, 48 mmol) was added via a glass syringe, and the solution was heated at 90° C. The solution turned dark purple within two minutes and dark red and thick after 20 minutes. The reaction was run for 43 h. The product was purified as stated above (1.5301 g, 86% yield).

In order to obtain both a definitive melting point determination and a clean NMR spectrum of the red product, separation of the clear plates and red needles was attempted by physical segregation under an optical microscope. While it was possible to effect some enrichment of one over the other, complete separation of such tiny crystals was not possible by hand. Chromatographic methods were also unsuccessful.

So, in order to allow additional characterization of the pure compound, 1,1',1"-trimethyl-4,4',4"-(1,3,5-triazin-2,4,6-triyl)tripyridinium trisiodide, Compound II was synthesized by methylation of 2,4,6-tris(4-pyridyl)-1,3,5-triazine using methyl iodide in DMF (see alternative synthesis in the Experimental section). The structures of crystals grown from this reaction product matched those collected as described above. Both structures have been deposited with the CCDC (1430162,1430163).

Example 7

The present example describes X-ray crystallography of Crystals of Compound I and Compound II.

Crystals of Compound I and Compound II were mounted on Mitegen loops with a drop of Paratone oil and placed in a cold nitrogen stream on the Bruker Smart APEX diffractometer. Full spheres of data were collected under control of the APEX2 program suite with data treatment, structure solution and refinement performed as described elsewhere. (See Bhat, et al., Eur J Inorg Chem, 3949-3958 (2015)). Relevant crystallographic data are listed in Tables 1-4.

Example 8

The present example describes Computational Analysis performed on disclosed compounds and crystalline forms.

Dispersion corrected density functional theory (DFT-D) calculations were carried out at the BLYP-D/def2-SVP level of theory (see Jurečka, 28 J Comp Chem 555-569 (2007)) in order to elucidate some of the energetic aspects of the crystal structure of Compound II. Inclusion of the empirical dispersion correction term is very important for these systems as stacking interactions involving aromatic rings or iodide are likely to be largely dependent on dispersion contributions.

Here some calculations are made in gas-phase while others use the conductor-like screening model (COSMO) in order to approximate the effect of the crystal environment. (See Klamt, 2 J Chem Soc, Perkin Trans 799-805 (1993)). As the permittivity of these crystals is currently unknown, a dielectric constant of 4.0 was chosen as a generic value. In all calculations the positions of heavy (non-hydrogen) atoms are held fixed at the crystal structure geometry while hydrogen positions are optimized at the BLYP-D/def2-SVP level of theory.

Interestingly, both gas-phase and implicit solvation (COSMO) calculations indicate that a flat structure for the 1,1',1"-trimethyl-4,4',4"-(1,3,5-triazin-2,4,6-triyl)tripyridinium cation of Compound II is more stable than the bowl configuration that is adopted in the crystal with energy differences of 9.1 kcal/mol (38 kJ/mol) for the gas-phase calculation and 7.2 kcal/mol (30 kJ/mol) using COSMO. This relatively large stability difference indicates that the non-covalent interactions of these cations with the surrounding iodides, and with each other, have a marked impact on the overall crystal structure.

Not surprisingly, implicit solvation interaction energies computed for both the concave (bottom-facing, interior iodides) and convex (bowed out, exterior iodides) pairs of cations indicate repulsive interactions, with values of +118.7 kcal/mol (496.6 kJ/mol) and +138.0 kcal/mol (577.4 kJ/mol), respectively. Recall that the triazine ring centroids of the concave cation pairs are 31 pm farther away from each other than in the convex pairs (Table 4). Introduction of the six iodides most closely associated with each cation pair results in strongly attractive interactions for both "octamer" (two cations plus six anions) types. Octamer binding energies as calculated using Equation I for the concave (interior iodides) and convex (exterior iodides) structures are computed to be −298.0 kcal/mol (−1247 kJ/mol) and −295.0 kcal/mol (−1234 kJ/mol) respectively.

$$IE=E(tot)-2E(\text{trivalent cation})-6E(I-)  \quad\quad \text{Equation I}$$

It is remarkable that these two octamers, whose structures are related but quite different, exhibit almost identical amounts of stabilization. This similarity in the stabilities of the concave and convex forms may help explain the coexistence of these two structures within the crystal framework. If either of the octamers were to have a stability significantly greater than that of the other, a different crystal structure might obtain.

Example 9

The present example provides measurements of optoelectronic properties of disclosed compounds and crystalline forms.

Figure 17:
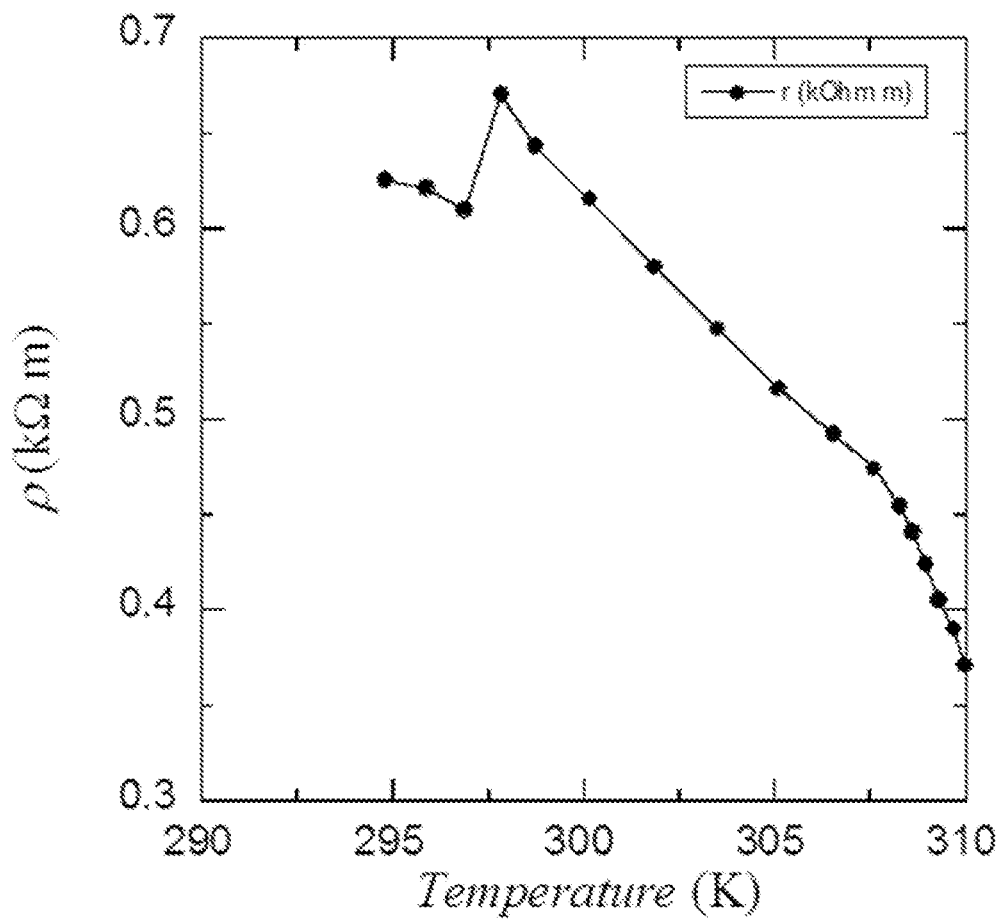
FIG. 17 shows resistivity measured on a single crystal sample of 1,1',1"-trimethyl-4,4',4"-(1,3,5-triazin-2,4,6-triyl)tripyridinium trisiodide, Compound II.

FIG. 17 shows resistivity measured on a single crystal sample of large crystals of 1,1',1"-trimethyl-4,4',4"-(1,3,5-triazin-2,4,6-triyl)tripyridinium trisiodide, Compound II. The graph depicts resistance of a sample. The calculated resistivity for samples is around 600 Ωm at room temperature. Such values indicate that crystal have semiconductor properties, comparable with pure silicon. Additionally, as temperature decrease, resistivity goes out of our measurement range for PPMS.

In some embodiments, resistivity for disclosed compounds and crystalline forms thereof is very large. In some embodiments, resistivity of disclosed compounds and crystalline forms is on an order of MΩ.

Figure 18:
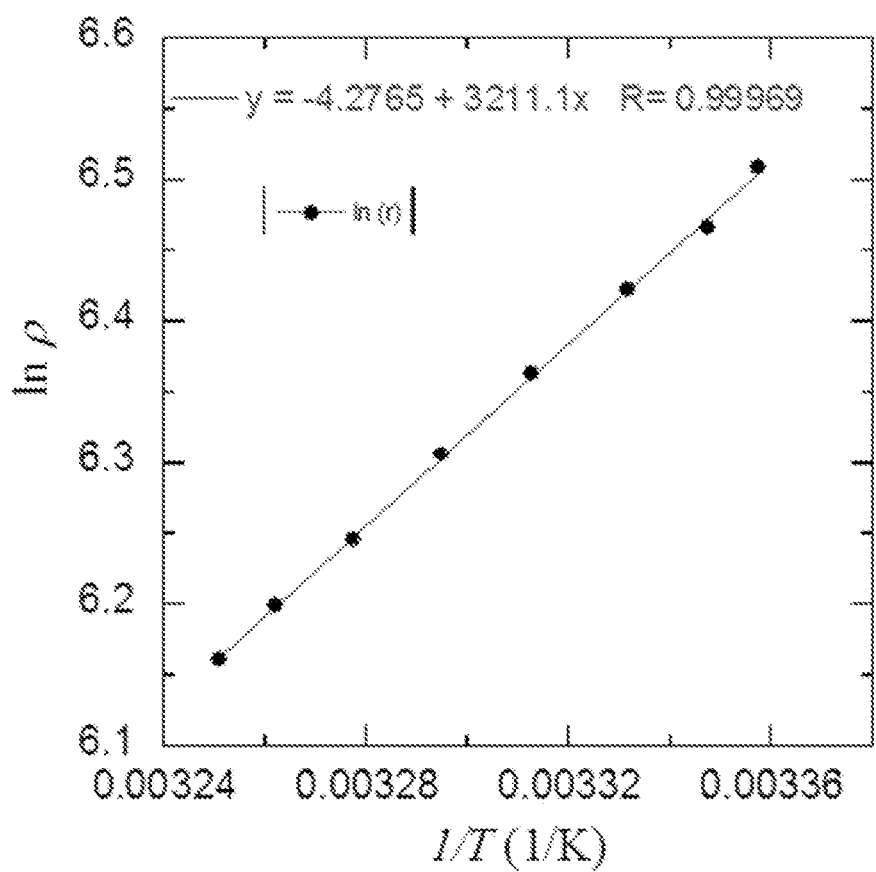
FIG. 18 shows band gap fitting from resistivity of 1,1',1"-trimethyl-4,4',4"-(1,3,5-triazin-2,4,6-triyl)tripyridinium trisiodide, Compound II.

FIG. 18 shows band gap fitting from resistivity measured on a single crystal sample. Using the Arrhenius equation:

$$\ln \rho = \ln \rho_0 + E_g/2k_BT$$

where $E_g/2k_B=3211.1$

Eg=0.55 eV. The estimated band gap from electrical transport data for a single crystal sample is around 0.55 eV.

Figure 19:
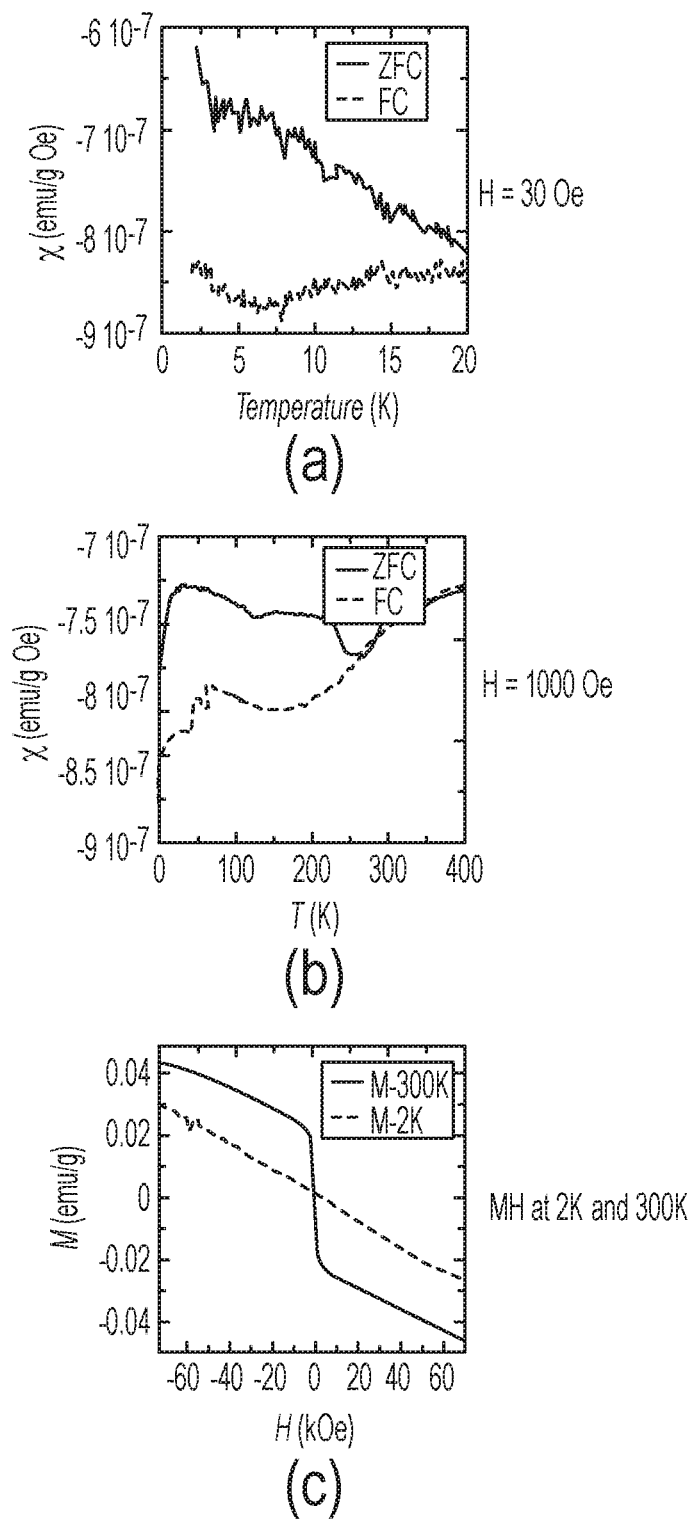
FIG. 19 shows magnetization measured by a SQUID magnetometer of 1,1',1"-trimethyl-4,4',4"-(1,3,5-triazin-2,4,6-triyl)tripyridinium trisiodide, Compound II.
Figure 20:
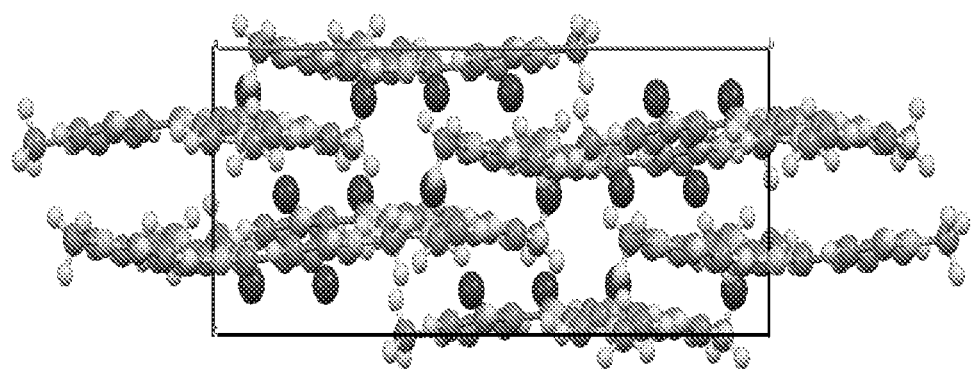
FIG. 20 shows a side view of a column of alternating convex and concave cation pairs in 1,1',1"-trimethyl-4,4',4"-(1,3,5-triazin-2,4,6-triyl)tripyridinium trisiodide, Compound II with iodide anions between concave pairs.
Figure 21:
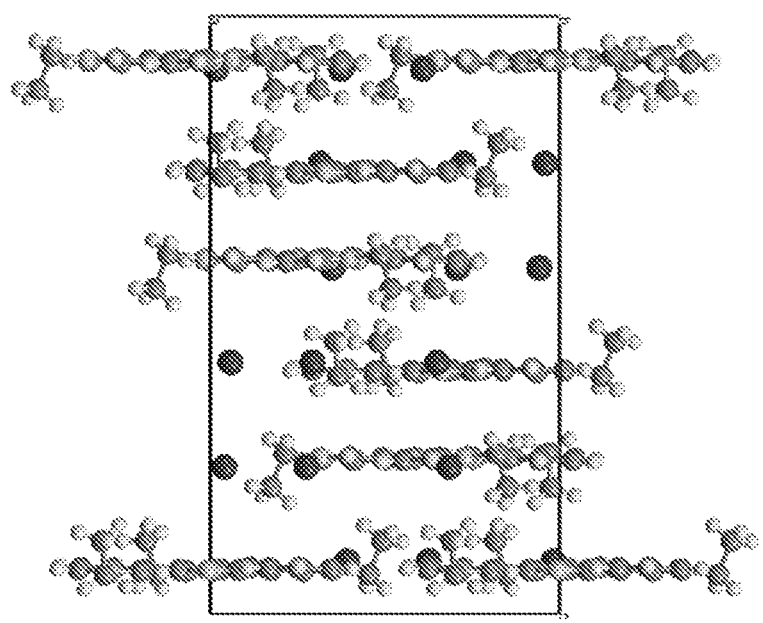
FIG. 21 shows a side view of a column of 1,1',1"-triethyl-3,3',3"-(1,3,5-triazin-2,4,6-triyl)tripyridinium trisiodide, 3-teptI, Compound III.
Figure 22:
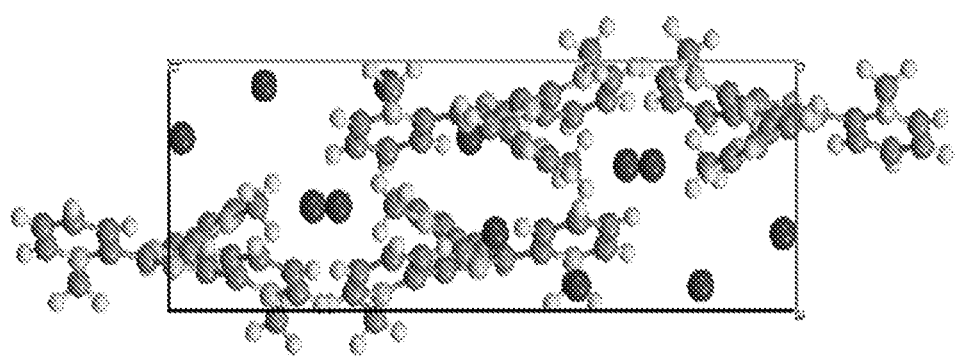
FIG. 22 shows a side view of a column of 1,1',1"-trimethyl-2,2',2"-(1,3,5-triazin-2,4,6-triyl)tripyridinium trisiodide, 2-tmptI, Compound IV.
Figure 23:
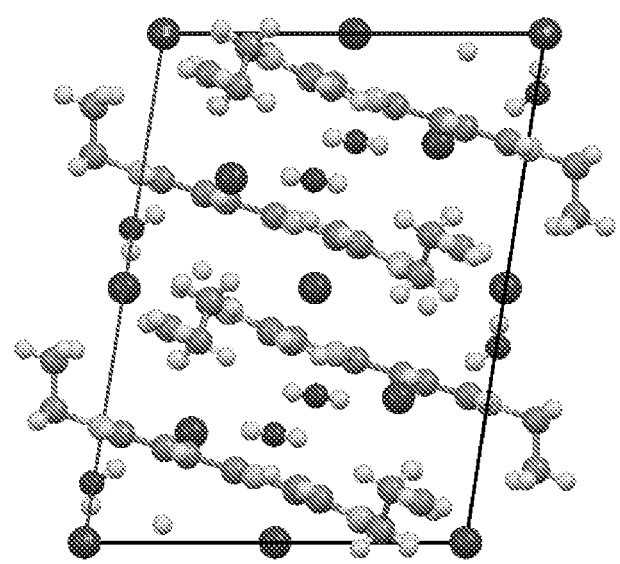
FIG. 23 shows a side view of a column of 1,1',1"-triethyl-4,4',4"-(1,3,5-triazin-2,4,6-triyl)tripyridinium trisiodide, 4-teptI, .2$H_2O$, Compound V.

FIG. 19 shows magnetization measured by a SQUID magnetometer of a single crystal sample. FIG. 19 shows that a single crystal exhibits diamagnetic property. FIG. 19 at panel (a) shows magnetic moment vs. temperature at a field of 30 Oe. FIG. 19 at panel (b) shows magnetic moment vs. temperature at a field of 1000 Oe. FIG. 19 at panel (c) shows magnetic moment v. magnetic field at 2K and 300K. It is estimated based on this data that a single crystal exhibits a phase transition near 250 K.

Example 10

The present example describes preparation of 1,1',1"-triethyl-4,4',4"-(1,3,5-triazin-2,4,6-triyl)tripyridinium trisbromide, Compound VIII.

2,4,6-tri(4-pyridyl)-1,3,5-triazine was placed in a Glass-Chem Microwave reaction vessel (105 mg, 3.34×10$^{-4}$ mols) with ethyl bromide (0.5 mL, 6.7×10$^{-3}$ mols) and 10 mL of DMF as the solvent. Three tubes were set up with the same parameters for a total of 315 mg of compound 1. Two blank tubes were run. The unreacted solution was white and turbid. Tubes were sealed and placed into a turntable inside a Mars 6 reaction microwave. The microwave was run at 600 Watts with a 20-minute ramp to 160° C. and a 20-minute hold time. The product was isolated via suction filtration and washed with cold diethyl ether. The olive green crude product was recrystallized in an azeotrope of isopropanol and water yielding a light olive green needlelike crystals. 187 mg (28% yield) of 1,1',1"-triethyl-4,4',4"-(1,3,5-triazin-2,4,6-triyl) tripyridinium trisbromide was obtained.

Example 11

The present example describes preparation of 1,1',1"-triethyl-3,3',3"-(1,3,5-triazin-2,4,6-triyl)tripyridinium trisbromide, Compound IX.

2,4,6-tri(3-pyridyl)-1,3,5-triazine was placed in a Glass-Chem Microwave reaction vessel (105 mg, 3.34×10$^{-4}$ mols)

37 with ethyl bromide (0.5 mL, 6.7×10$^{-3}$ mols) and 10 mL of DMF as the solvent. Two tubes were set up with the same parameters for a total of 210 mg of compound 1. Two blank tubes were run. The unreacted solution was white and turbid. Tubes were sealed and placed into a turntable inside a Mars 6 reaction microwave. The microwave was run at 550 Watts with a 20-minute ramp to 160° C. and 20-minute hold time. The product was isolated via suction filtration and washed with cold diethyl ether. A crude yield of yellow-green 1,1',1"-triethyl-3,3',3"-(1,3,5-triazin-2,4,6-triyl)tripyridinium trisbromide (393 mg, 92% yield) was obtained.

Example 12

The present example describes preparations of triazinium iodide compounds, crystals, forms, and/or salts including, for examples, Compounds II-VII via a microwave reaction.

2,4,6-tri(n-pyridyl)-1,3,5-triazine, where n=2, 3, or 4, is placed in a GlassChem Microwave reaction vessel with methyl iodide or ethyl iodide and 10 mL of DMF as the solvent. Two tubes are set up with the same parameters. Two blank tubes were run. Tubes are sealed and placed into a turntable inside a Mars 6 reaction microwave. The microwave was run at 550 Watts with a 20-minute ramp to 160° C. and 20-minute hold time. The product is isolated via suction filtration and washed with cold diethyl ether. Triazinium iodide compounds, crystals, forms, and/or salts are obtained.

Example 13

The present example shows a calculated HOMO-LUMO gap for compounds disclosed herein.

Table 5 shows a calculated HOMO-LUMO gap for 1,1',1"-trimethyl-4,4',4"-(1,3,5-triazin-2,4,6-triyl)tripyridinium trisiodide, Compound II; 1,1',1"-triethyl-3,3',3"-(1,3,5-triazin-2,4,6-triyl)tripyridinium trisiodide, 3-teptI, Compound III; 1,1',1"-trimethyl-2,2',2"-(1,3,5-triazin-2,4,6-triyl)tripyridinium trisiodide, 2-tmptI, Compound IV; and 1,1',1"-triethyl-4,4',4"-(1,3,5-triazin-2,4,6-triyl)tripyridinium trisiodide, 4-teptI, Compound V.

TABLE 5

Calculated HOMO-LUMO Gap

| Compound | Calculated gap (eV) | Calculated gap (nm) |
|---|---|---|
| 4-tmptI, Compound II | 0.66 | 1873 |
| 3-teptI, Compound III | 0.94 | 1315 |
| 2-tmptI, Compound IV | 0.62 | 1994 |
| 4-teptI, Compound V | 0.61 | 2026 |

Calculated HOMO-LUMO gap used density functional theory for 4tmptI neutral unit from crystal structure corresponds with lower energy thermal band gap from four-point probe measurements (0.55 eV) 298-307K while higher energy gap shown by these measurements (1.79 eV) 308-310K correlates more closely with optical measurements.

Figure 29:
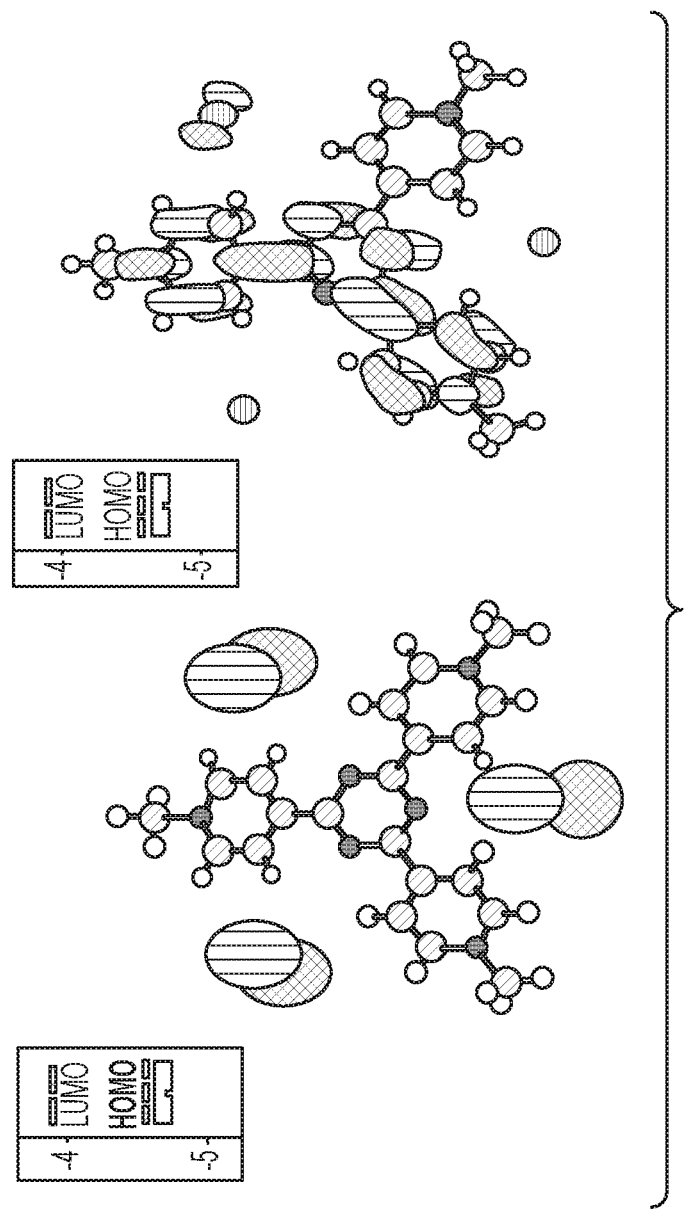
FIG. 29 shows a HOMO-LUMO gap molecular orbital diagram for 1,1',1"-trimethyl-4,4',4"-(1,3,5-triazin-2,4,6-triyl)tripyridinium trisiodide, Compound II.
Figure 30:
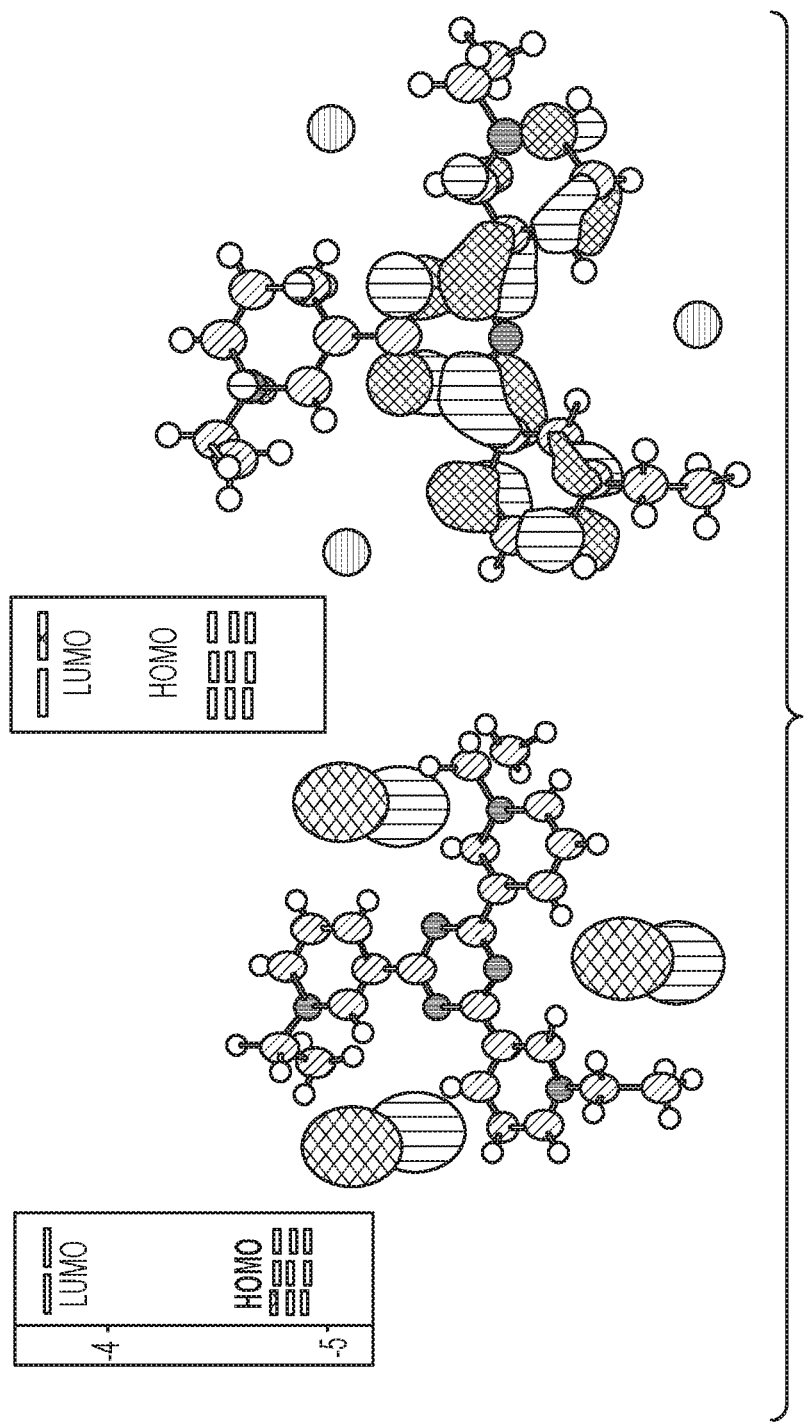
FIG. 30 shows a HOMO-LUMO gap molecular orbital diagram for 1,1',1"-triethyl-3,3',3"-(1,3,5-triazin-2,4,6-triyl)tripyridinium trisiodide, 3-teptI, Compound III.
Figure 31:
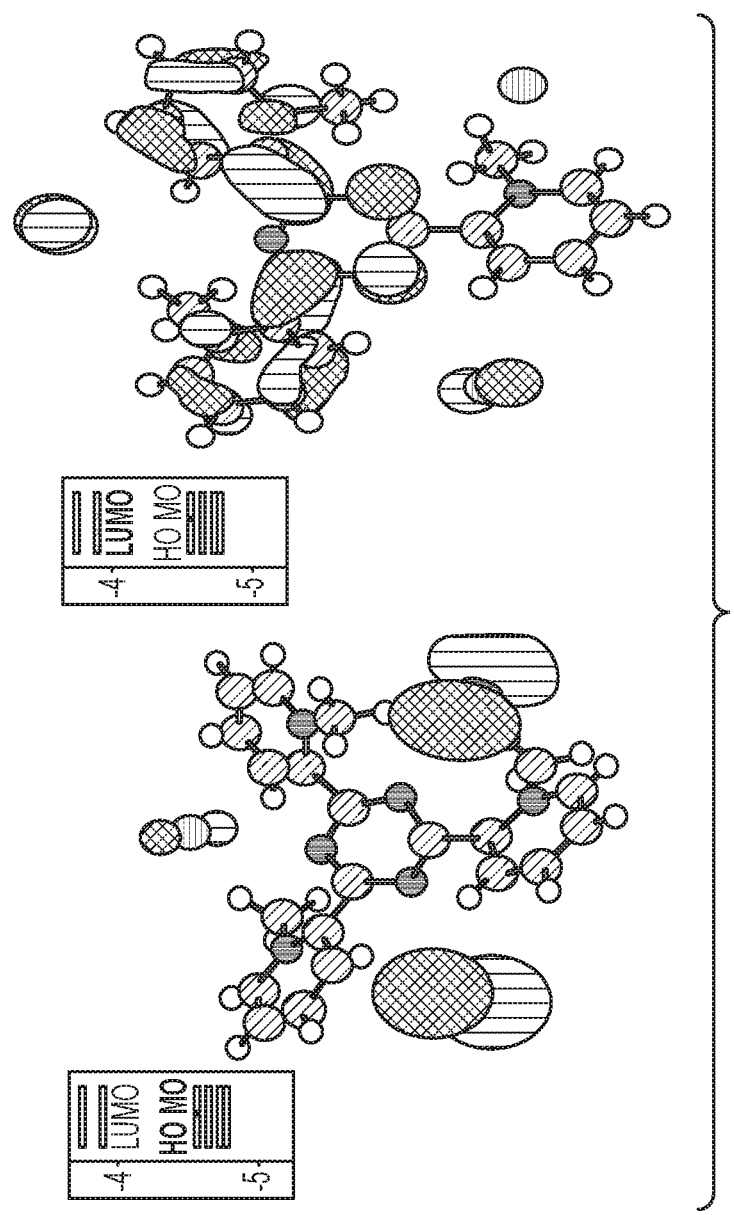
FIG. 31 shows a HOMO-LUMO gap molecular orbital diagram for 1,1',1"-trimethyl-2,2',2"-(1,3,5-triazin-2,4,6-triyl)tripyridinium trisiodide, 2-tmptI, Compound IV.
Figure 32:
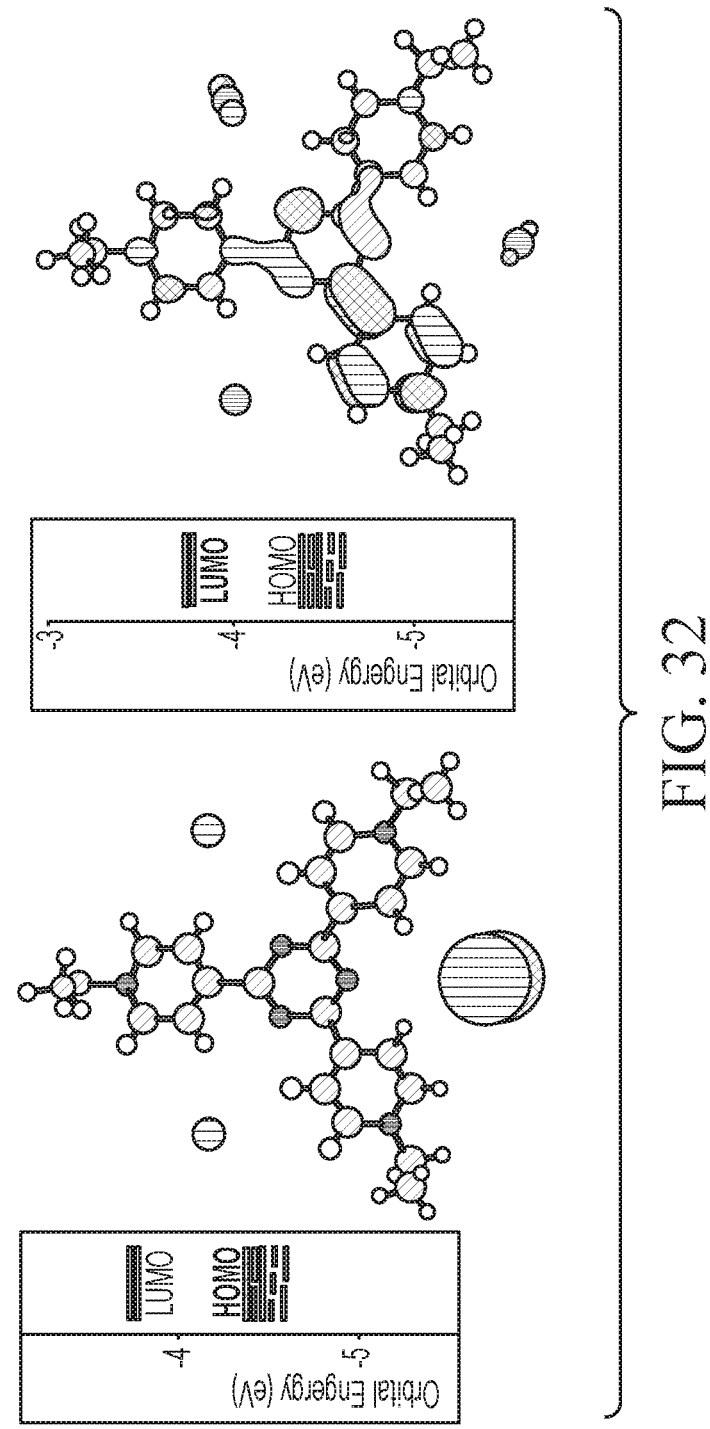
FIG. 32 shows a HOMO-LUMO gap molecular orbital diagram for 1,1',1"-triethyl-4,4',4"-(1,3,5-triazin-2,4,6-triyl)tripyridinium trisiodide, 4-teptI.2$H_2O$, Compound V.

FIG. 29 shows a HOMO-LUMO gap molecular orbital diagram for 1,1',1"-trimethyl-4,4',4"-(1,3,5-triazin-2,4,6-triyl)tripyridinium trisiodide, Compound II. FIG. 30 shows a HOMO-LUMO gap molecular orbital diagram for 1,1',1"-triethyl-3,3',3"-(1,3,5-triazin-2,4,6-triyl)tripyridinium trisiodide, 3-teptI, Compound III. FIG. 31 shows a HOMO-LUMO gap molecular orbital diagram for 1,1',1"-trimethyl-2,2',2"-(1,3,5-triazin-2,4,6-triyl)tripyridinium trisiodide, 2-tmptI, Compound IV. FIG. 32 shows a HOMO-LUMO

38 gap molecular orbital diagram for 1,1',1"-triethyl-4,4',4"-(1,3,5-triazin-2,4,6-triyl)tripyridinium trisiodide, 4-teptI, Compound V 2H$_2$O.

Example 14

The present example shows calculated band gap for compounds disclosed herein.

Table 6 shows band gap estimates from spectra (extrapolated linear portion of a slope) for 1,1',1"-trimethyl-4,4',4"-(1,3,5-triazin-2,4,6-triyl)tripyridinium trisiodide, Compound II (red powder); 1,1',1"-trimethyl-4,4',4"-(1,3,5-triazin-2,4,6-triyl)tripyridinium trisiodide, Compound II (black needles); 1,1',1"-triethyl-3,3',3"-(1,3,5-triazin-2,4,6-triyl)tripyridinium trisiodide, 3-teptI, Compound III; 1,1',1"-trimethyl-2,2',2"-(1,3,5-triazin-2,4,6-triyl)tripyridinium trisiodide, 2-tmptI, Compound IV; 1,1',1"-triethyl-4,4',4"-(1,3,5-triazin-2,4,6-triyl)tripyridinium trisiodide, 4-teptI, Compound V; 1,1',1"-trimethyl-3,3',3"-(1,3,5-triazin-2,4,6-triyl)tripyridinium trisiodide, 3-tmptI, Compound VI; 1,1',1"-triethyl-4,4',4"-(1,3,5-triazin-2,4,6-triyl)tripyridinium trisbromide, Compound VIII; and 1,1',1"-triethyl-3,3',3"-(1,3,5-triazin-2,4,6-triyl)tripyridinium trisbromide, Compound IX.

TABLE 6

Band Gap Estimates from Spectra (extrapolated linear portion of the slope)

| Compound | λ-intercept (nm +/− 5) | Band Gap (eV +/− 0.02) |
|---|---|---|
| 4-tmptI, Compound II (red powder) | 810 | 1.53 |
| 4-tmptI, Compound II (black needles) | 835 | 1.48 |
| 3-teptI, Compound III | 725 | 1.71 |
| 2-tmptI, Compound IV | 660 | 1.88 |
| 4-teptI, Compound V | 1020 | 1.22 |
| 3-tmptI, Compound VI | 740 | 1.68 |
| 4-teptBr, Compound VIII | 685 | 1.81 |
| 3-teptBr, Compound IX | 545 | 2.27 |
| Four-Point Probe (black needles) | (nm) | (eV) |
| 298-307K | 2254 | 0.55 |
| 308-310K | 693 | 1.79 |

Calculated HOMO-LUMO gap used density functional theory for 4tmptI neutral unit from crystal structure corresponds with lower energy thermal band gap from four-point probe measurements (0.55 eV) while higher energy gap shown by these measurements (1.79 eV) correlates more closely with optical measurements.

Example 15

The present example shows measured diffuse reflectance spectra for compounds disclosed herein.

Figure 33:
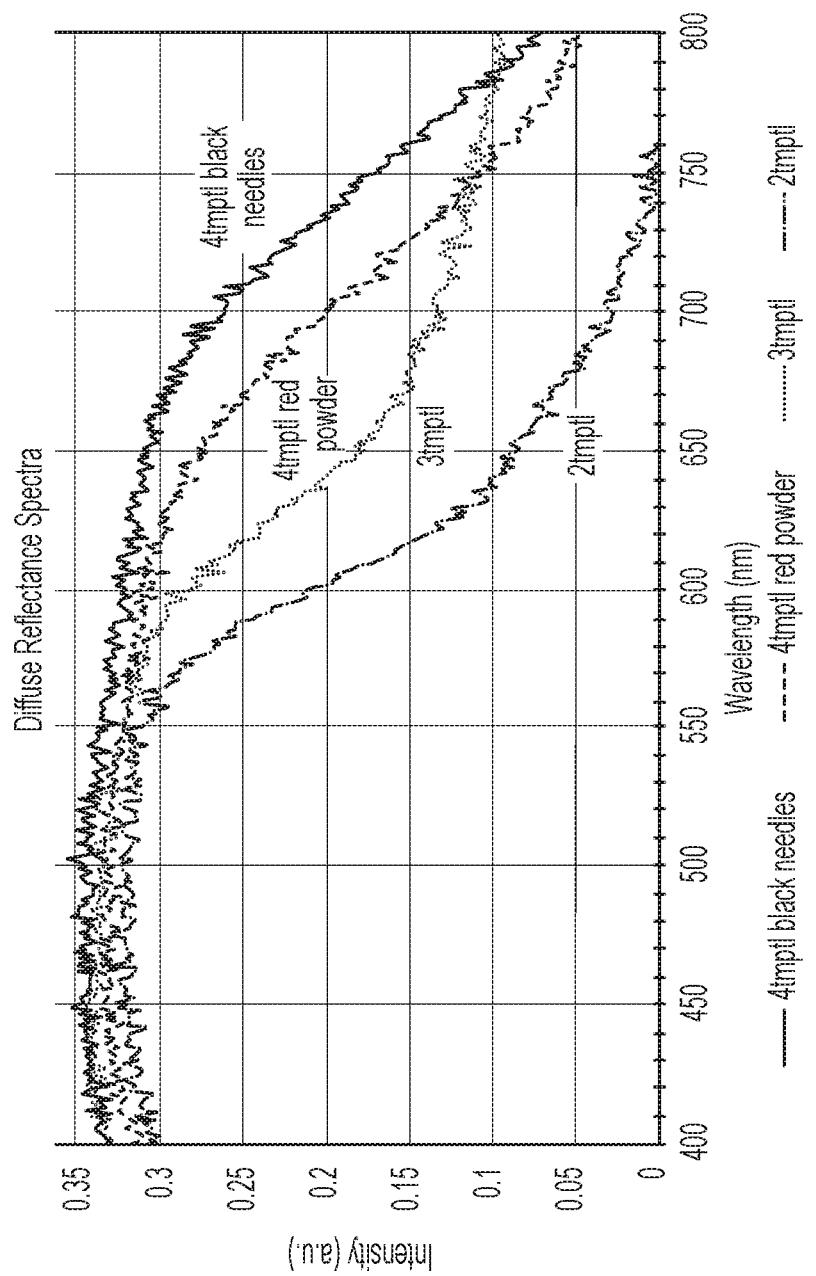
FIG. 33 shows measured diffuse reflectance spectra of Compound II (red powder); Compound II (black needles); Compound IV; and Compound VI.

FIG. 33 shows measured diffuse reflectance spectra for 1,1',1"-trimethyl-4,4',4"-(1,3,5-triazin-2,4,6-triyl)tripyridinium trisiodide, Compound II (red powder); 1,1',1"-trimethyl-4,4',4"-(1,3,5-triazin-2,4,6-triyl)tripyridinium trisiodide, Compound II (black needles); 1,1',1"-trimethyl-2,2',2"-(1,3,5-triazin-2,4,6-triyl)tripyridinium trisiodide, 2-tmptI, Compound IV; and 1,1',1"-trimethyl-3,3',3"-(1,3,5-triazin-2,4,6-triyl)tripyridinium trisiodide, 3-tmptI, Compound VI.

Diffuse reflectance spectra of N-methyl pyridyl triazinium iodides taken using OLIS Clarity diffuse reflectance spectrometer.

Figure 34:
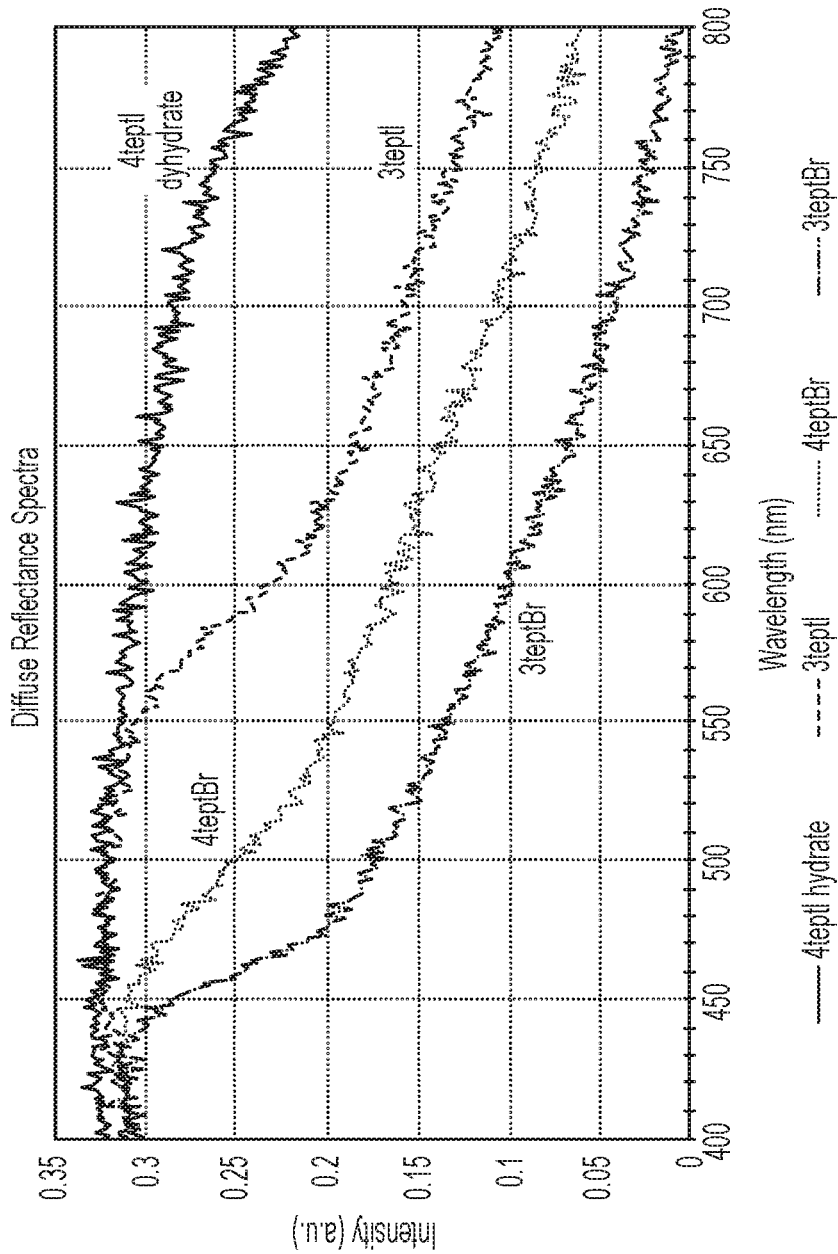
FIG. 34 shows measured diffuse reflectance spectra of Compound III; Compound V; Compound VIII; and Compound IX.

FIG. 34 shows measured diffuse reflectance spectra for 1,1',1''-triethyl-3,3',3''-(1,3,5-triazin-2,4,6-triyl)tripyridinium trisiodide, 3-teptI, Compound III; 1,1',1''-triethyl-4,4',4''-(1,3,5-triazin-2,4,6-triyl)tripyridinium trisiodide, 4-teptI hydrate, Compound V; 1,1',1''-triethyl-4,4',4''-(1,3,5-triazin-2,4,6-triyl)tripyridinium trisbromide, Compound VIII; and 1,1',1''-triethyl-3,3',3''-(1,3,5-triazin-2,4,6-triyl)tripyridinium trisbromide, Compound IX.

Diffuse reflectance spectra of N-ethyl pyridyl triazinium halides taken using OLIS Clarity diffuse reflectance spectrometer.

This data demonstrates that band gap can be tuned by (1) using different alkyl group, (2) changing position of N-alkyl substituent on pyridine rings, (3) substituting anion, and (4) controlling size of crystallites.

Example 16

The present example shows measured thermal gravimetric analysis for 1,1',1''-trimethyl-4,4',4''-(1,3,5-triazin-2,4,6-triyl)tripyridinium trisiodide, Compound II.

Figure 35:
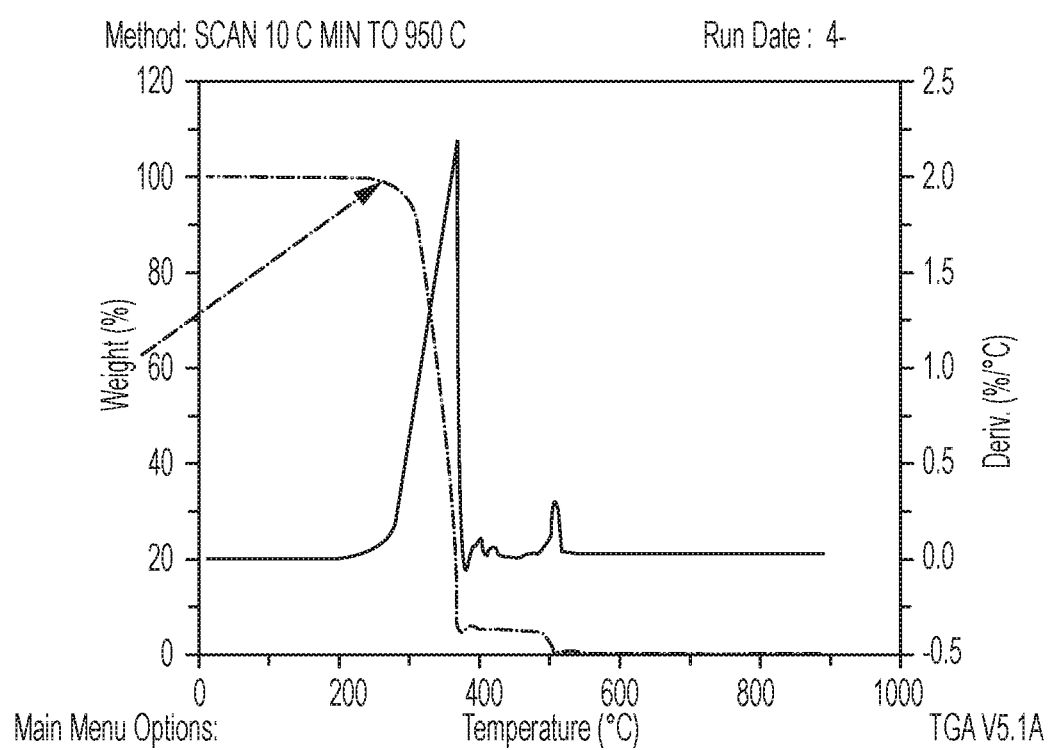
FIG. 35 shows thermal gravimetric analysis data for 1,1',1"-trimethyl-4,4',4"-(1,3,5-triazin-2,4,6-triyl)tripyridinium trisiodide, Compound II.

FIG. 35 shows thermal gravimetric analysis spectra of for 1,1',1''-trimethyl-4,4',4''-(1,3,5-triazin-2,4,6-triyl)tripyridinium trisiodide, Compound II. The graph shows a first event with onset of about 260° C. with a first derivative peak at 380° C. (midpoint of transition). A weight loss of 95% is observed after the first event and stayed the same until 500° C. A second peak can be seen at 500° C. mark, but it is not as intense as the first peak. Sample lost all weight after 500° C.

Example 17

The present example shows measured thermal gravimetric analysis for 1,1',1''-triethyl-3,3',3''-(1,3,5-triazin-2,4,6-triyl)tripyridinium trisiodide, 3-teptI, Compound III.

Figure 36:
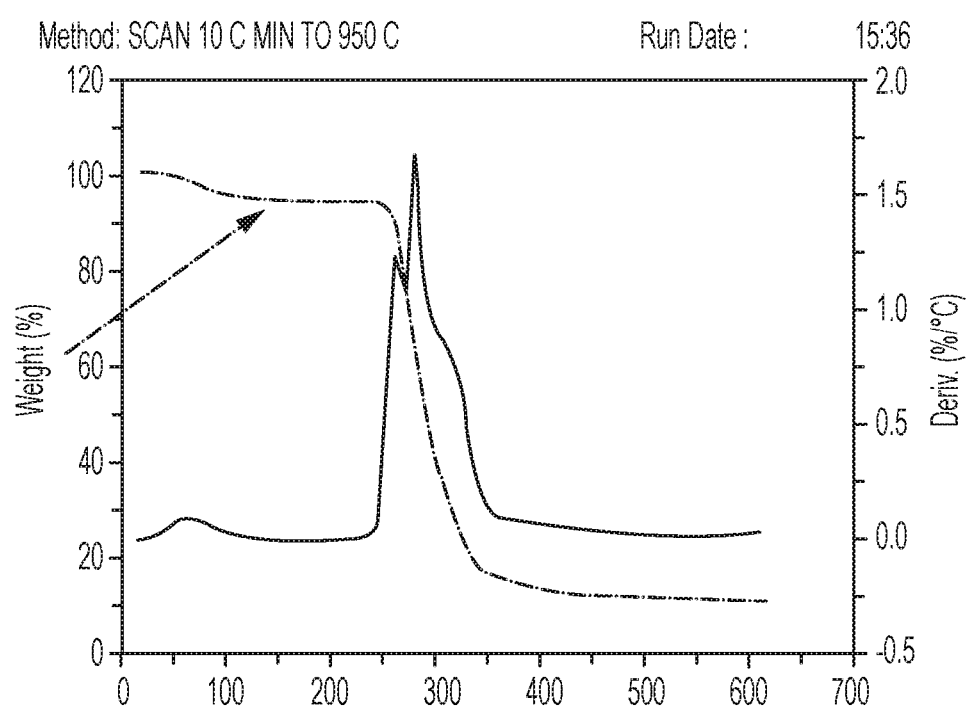
FIG. 36 shows thermal gravimetric analysis data for 1,1',1"-triethyl-3,3',3"-(1,3,5-triazin-2,4,6-triyl)tripyridinium trisiodide, 3-teptI, Compound III.

FIG. 36 shows thermal gravimetric analysis spectra of for 1,1',1''-triethyl-3,3',3''-(1,3,5-triazin-2,4,6-triyl)tripyridinium trisiodide, 3-teptI, Compound III. A 50° C. weight loss of 5% can be seen followed by a 150-300° C. plateau. A first event is shown at 300° C. A 90% weight loss is observed with this first event. Three derivatives can be seen at 80° C., 280° C., and 310° C. Note that the instrument ceased operation at 650° C.

Example 18

The present example shows measured thermal gravimetric analysis for 1,1',1''-trimethyl-2,2',2''-(1,3,5-triazin-2,4,6-triyl)tripyridinium trisiodide, 2-tmptI, Compound IV.

Figure 37:
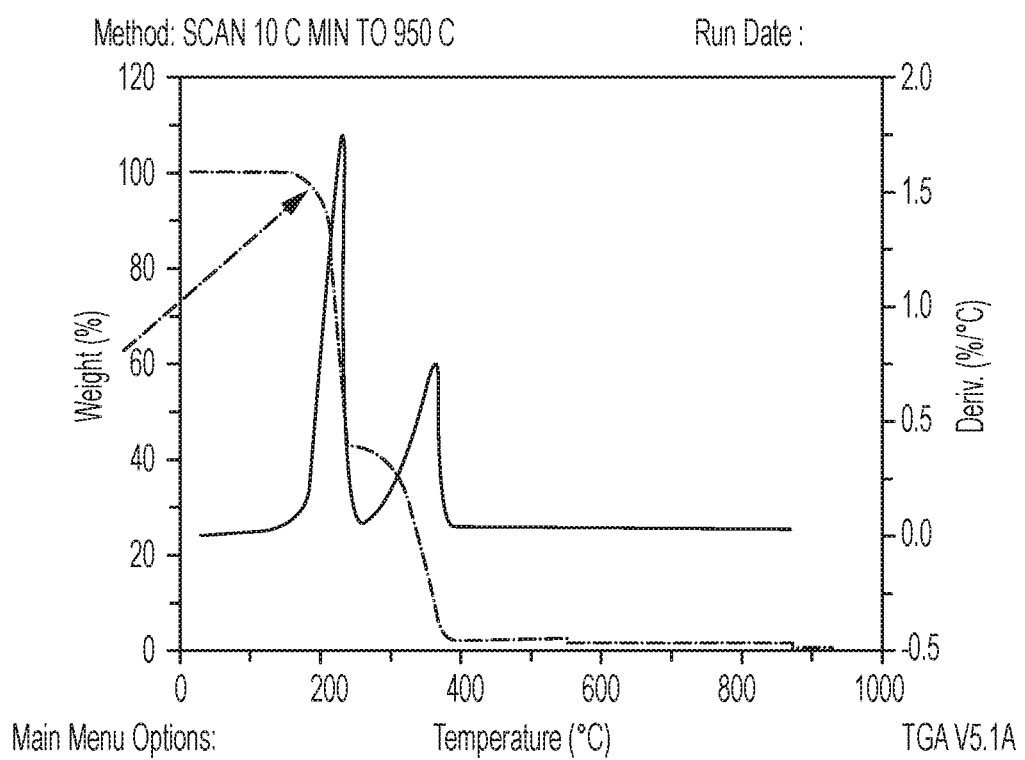
FIG. 37 shows thermal gravimetric analysis data for 1,1',1"-trimethyl-2,2',2"-(1,3,5-triazin-2,4,6-triyl)tripyridinium trisiodide, 2-tmptI, Compound IV.

FIG. 37 shows thermal gravimetric analysis spectra of for 1,1',1''-trimethyl-2,2',2''-(1,3,5-triazin-2,4,6-triyl)tripyridinium trisiodide, 2-tmptI, Compound IV. A first event is observed at 200° C. with derivative peak at 220° C. and a weight loss of 60% is seen. A second event occurred at 230° C. where more weight loss was seen 60%-95% over the 230° C.-350° C. temp range. A second peak is seen at 350° C.

Example 19

The present example shows measured thermal gravimetric analysis for 1,1',1''-triethyl-4,4',4''-(1,3,5-triazin-2,4,6-triyl)tripyridinium trisiodide, 4-teptI, .2H$_2$O, Compound V.

Figure 38:
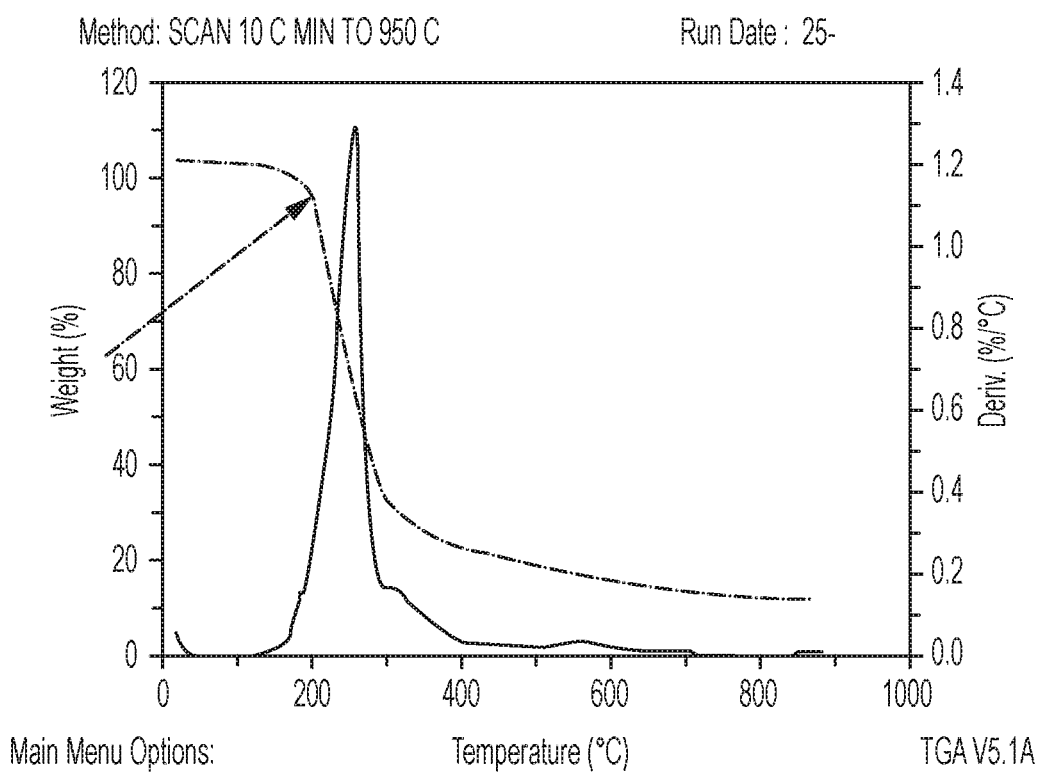
FIG. 38 shows thermal gravimetric analysis data for 1,1',1"-triethyl-4,4',4"-(1,3,5-triazin-2,4,6-triyl)tripyridinium trisiodide, 4-teptI.2$H_2O$, Compound V.

FIG. 38 shows thermal gravimetric analysis spectra of 1,1',1''-triethyl-4,4',4''-(1,3,5-triazin-2,4,6-triyl)tripyridinium trisiodide, 4-teptI, .2H$_2$O, Compound V. A first event at 200° C. with a weight loss of 80% over 200° C.-300° C. (sharp weight loss). A steady decrease until 900° C. with an additional 10% weight loss for an overall of 90% weight loss. A very big peak is seen at 250° C.

Example 20

The present example shows measured thermal gravimetric analysis for 1,1',1''-trimethyl-3,3',3''-(1,3,5-triazin-2,4,6-triyl)tripyridinium trisiodide, 3-tmptI, Compound VI.

Figure 39:
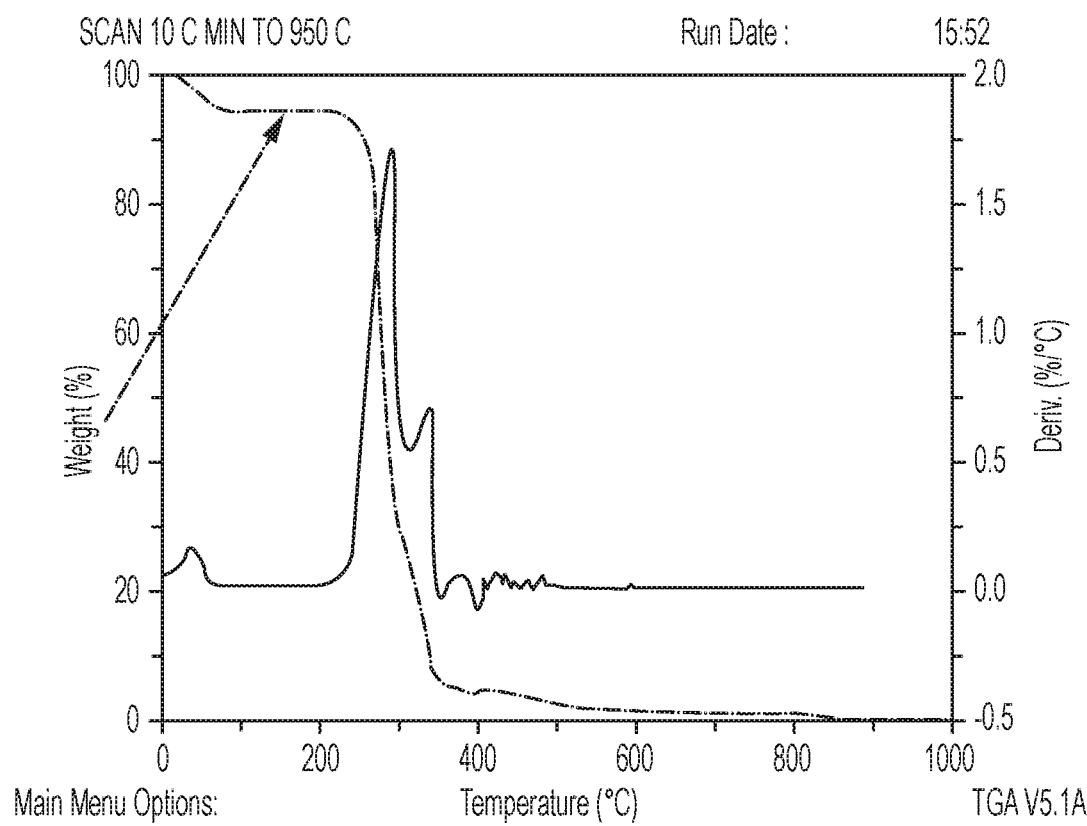
FIG. 39 shows thermal gravimetric analysis data for 1,1',1"-trimethyl-3,3',3"-(1,3,5-triazin-2,4,6-triyl)tripyridinium trisiodide, 3-tmptI, Compound VI.

FIG. 39 shows thermal gravimetric analysis spectra of for 1,1',1''-trimethyl-3,3',3''-(1,3,5-triazin-2,4,6-triyl)tripyridinium trisiodide, 3-tmptI, Compound VI. At 50° C. there is a 5% weight loss with its derivative peak to match with it. A plateau until 300° C. then weight loss of 95% overall (derivative at 320° C.). A second peak is seen at 350° C. and gradually lost weight as temp increased.

Other Embodiments and Equivalents

While the present disclosures have been described in conjunction with various embodiments, and examples, it is not intended that they be limited to such embodiments, or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments, that are functional and/or equivalents of the specific embodiments, and features that have been described and illustrated. Moreover, the features of the particular examples and embodiments, may be used in any combination. The present disclosure therefore includes variations from the various examples and embodiments, described herein, as will be apparent to one of skill in the art.

What is claimed is:
1. A crystalline form of Compound II

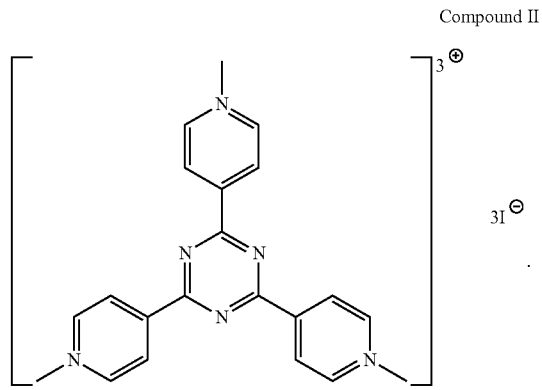

Compound II

2. The crystalline form of claim 1, characterized by one or more peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

3. The crystalline form of claim 1, characterized by at least two peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

4. The crystalline form of claim 1, characterized by at least three peaks in its Powder X-ray diffraction pattern selected from those at about 16.68, about 19.74, about 22.42, about 24.90, about 25.94, about 27.08, about 29.08, about 31.02, about 32.8, or about 33.72 degrees 2-theta.

5. The crystalline form of claim 1, having a PXRD substantially similar to that depicted in FIG. 9.

6. The crystalline form of claim 1, characterized by a trigonal unit cell.

7. The crystalline form of claim 1, wherein the crystalline solid is substantially free of amorphous Compound II.

8. The crystalline form of claim 1, wherein the crystalline solid is substantially free of impurities.

9. The crystalline form of claim 1, characterized by a band gap of about 1.8 eV.

10. The crystalline form of claim 1, characterized by an electrical resistivity of about $6\times10^2$ $\rho(\Omega\iota\eta)$ measured at about room temperature.

11. The crystalline form of claim 1, when it is placed in solution its solvated cation is characterized by three peaks in $^1$H— MR at δ ppm selected from the group consisting of about 9.48, about 9.36, and about 4.50, and combinations thereof.

12. An organic semiconductor having a formula of Compound II.

13. An electronic device comprising the organic semiconductor having the formula of Compound II of claim 12.

14. An electronic material comprising the organic semiconductor having the formula of Compound II of claim 12.

15. The crystalline form of claim 1, characterized in that it exhibits diamagnetism.

16. The crystalline form of claim 1, characterized by a Piedfort Unit having face to face π-π stacking.

17. The crystalline form of claim 1, comprising two cations and six anions so that the crystal has a non-zero octupolar moment.

18. The crystalline form of claim 1, having a decomposition temperature of 383° C.

19. A process for producing the crystal 1,1',1"-trimethyl-4,4',4"-(1,3,5-triazin-2,4,6-triyl)tripyridinium trisiodide as defined in claim 1, which comprises steps of:
    dissolving 4-cyano-1-methylpyridinium iodide in methanol to form a mixture; and
    adding $Hg_2Cl_2$, AgCl, or $PbCl_2$ to the mixture.

20. The crystalline form of claim 2, characterized by its X-ray or neutron diffraction patterns corresponding to a trigonal unit cell with parameters of about a=23.86, b=23.86, c=7.26 Angstroms and about alpha=beta=90 degrees, gamma=120 degrees, and all equivalent permutations thereof.

* * * * *